United States Patent [19]

Oku et al.

[11] Patent Number: 5,215,994

[45] Date of Patent: Jun. 1, 1993

[54] ANGIOTENIN II ANTAGONIZING HETEROCYCLIC DERIVATIVES

[75] Inventors: Teruo Oku; Hiroyuki Setoi; Hiroshi Kayakiri; Shigeki Satoh; Takayuji Inoue; Yuki Saitoh; Akio Kuroda, all of Tsukuba; Hirokazu Tanaka, Tsuchiura, all off, Japan

[73] Assignee: Fujisawa Pharmaceutical Co., Ltd., Osaka, Japan

[21] Appl. No.: 758,688

[22] Filed: Sep. 12, 1991

Related U.S. Application Data

[63] Continuation-in-part of Ser. No. 748,954, Aug. 23, 1991.

[30] Foreign Application Priority Data

Sep. 25, 1990 [GB] United Kingdom ............ 9020838
Oct. 29, 1990 [GB] United Kingdom ............ 9023467
Dec. 31, 1990 [GB] United Kingdom ............ 9028216
Feb. 25, 1991 [GB] United Kingdom ............ 9103874
Apr. 3, 1991 [GB] United Kingdom ............ 9106956
Apr. 5, 1991 [GB] United Kingdom ............ 9107231
Jun. 14, 1991 [GB] United Kingdom ............ 9112803

[51] Int. Cl.$^5$ .................. A61K 31/435; C07D 471/04
[52] U.S. Cl. ................................... 514/266; 514/303; 514/338; 514/365; 514/374; 514/381; 514/382; 544/277; 546/118; 546/270; 546/271; 548/159; 548/181; 548/217; 548/235; 548/252; 548/253; 548/254
[58] Field of Search .............. 546/118, 270, 271; 544/277; 548/159, 181, 217, 235, 252, 253, 254; 514/266, 303, 338, 365, 374, 381, 382

[56] References Cited

PUBLICATIONS

Chemical Abstracts vol. 116(9), 194338y (1992); Abstract of Ger. Offen. 4023215 (1992).

Primary Examiner—Bernard Dentz
Attorney, Agent, or Firm—Oblon, Spivak, McClelland, Maier & Neustadt

[57] ABSTRACT

The invention relates to compounds of the formula

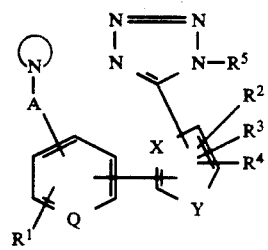

wherein

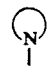

represents a condensed or uncondensed imidazolyl ring and the rest of the variables are as defined in the specification. They are angiotensin II antagonists useful for treating hypertension, etc..

10 Claims, No Drawings

ANGIOTENIN II ANTAGONIZING HETEROCYCLIC DERIVATIVES

This application is a continuation-in-part of U.S. application Ser. No. 07/748,954, filed Aug. 23, 1991.

The present invention relates to novel heterocyclic derivatives and a pharmaceutically acceptable salt thereof. More particularly, it relates to novel imidazole derivatives and a pharmaceutically acceptable salt thereof which have pharmacological activities such as angiotensin II antagonism and the like, to process for preparation thereof, to a pharmaceutical composition comprising the same and to a use of the same as a medicament.

Accordingly, one object of the present invention is to provide novel imidazole derivatives and a pharmaceutically acceptable salt thereof, which are useful as a potent and selective antagonist of angiotensin II receptor.

Another object of the present invention is to provide process for preparation of said imidazole derivatives or a salt thereof.

A further object of the present invention is to provide a pharmaceutical composition comprising, as an active ingredient, said imidazole derivatives or a pharmaceutically acceptable salt thereof.

Still further object of the present invention is to provide a use of said imidazole derivatives or a pharmaceutically acceptable salt thereof as a medicament such as angiotensin II antagonist useful for treating or preventing angiotensin II mediated diseases, for example, hypertension (e.g. essential hypertension, renal hypertension, etc.), heart failure, and the like in human being or animals.

The imidazole derivatives of the present invention are novel and can be represented by the formula (I):

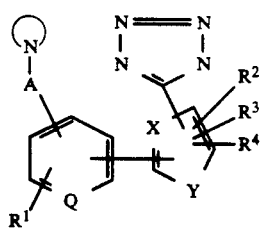

(I)

wherein
$R^1$ is hydrogen, halogen, nitro, lower alkyl, lower alkoxy, amino or acylamino,
$R^2$, $R^3$ and $R^4$ are each hydrogen, halogen, nitro, cyano, lower alkyl, lower alkenyl, lower alkylthio, more or di or trihalo(lower)alkyl, oxo(lower)alkyl, hydroxy(lower)alkyl or optionally esterified carboxy; or
$R^2$ and $R^3$ are linked together to form 1,3-butadienylene,
$R^5$ is hydrogen or imino-protective group,
A is lower alkylene,
Q is CH or N,
X is N or CH,
Y is NH, O or S, and

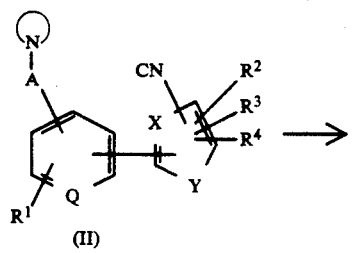

is condensed or uncondensed imidazolyl which may have suitable substituent(s).

According to the present invention, the object compound (I) can be prepared by the following processes.

Process 1

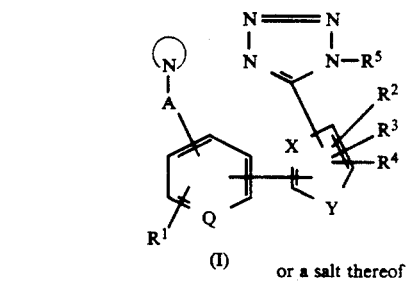

Process 2

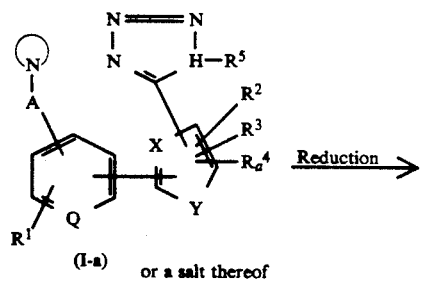

Process 3

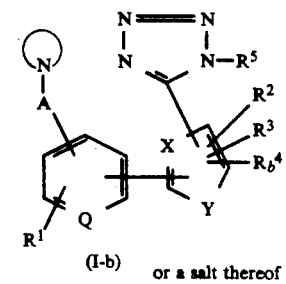

-continued

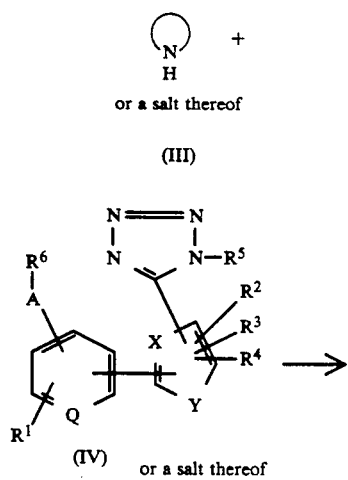

(III) or a salt thereof (IV) or a salt thereof

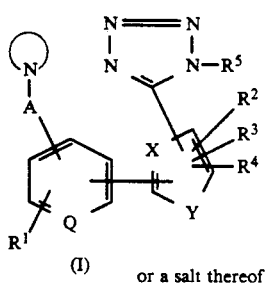

(I) or a salt thereof

Process 4

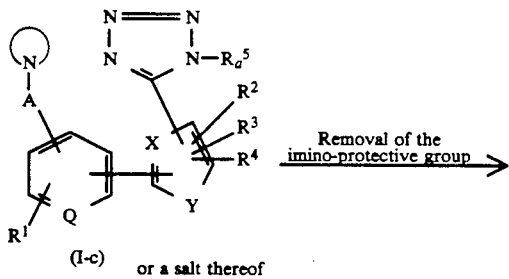

(I-c) or a salt thereof

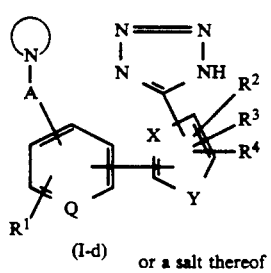

(I-d) or a salt thereof

Wherein
$R^1$, $R^2$, $R^3$, $R^4$, $R^5$, A, Q, X, Y and each as defined above,
$R_a^4$ is oxo(lower)alkyl or halogen,
$R_b^4$ is hydroxy(lower)alkyl or hydrogen,
$R_a^5$ is imino-protective group, and
$R^6$ is acid residue.

Suitable salts of the compound (I) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like, and the preferable example thereof is an acid addition salt.

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" and lower alkyl group in the term "lower alkylthio" may include straight or branched one, having 1 to 6 carbon atom(s), such as methyl, ethyl, propyl, isopropyl, butyl, t-butyl, pentyl, hexyl, preferably one having 1 to 5 carbon atoms, and the like.

Suitable "lower alkenyl" may include vinyl, 1-propenyl, allyl, 1-butenyl, 2-butenyl, 2-pentenyl, and the like, preferably one having 2 to 4 carbon atoms, in which the most preferred one is vinyl.

Suitable "lower alkylene" is one having 1 to 6 carbon atom(s) and may include methylene, ethylene, trimethylene, propylene, tetramethylene, methyltrimethylene, dimethylethylene, hexamethylene, and the like, in which the preferred one is methylene.

Suitable "halogen" means fluoro, chloro, bromo and iodo.

Suitable "lower alkoxy" may include straight or branched one such as methoxy, ethoxy, propoxy, isopropoxy, butoxy, isobutoxy, tert-butoxy, pentyloxy, hexyloxy or the like, in which the preferable one is $C_1$-$C_4$ alkoxy.

Suitable acyl group in the term "acylamino" may include carbamoyl, thiocarbamoyl, sulfamoyl, aliphatic acyl, aromatic acyl, heterocyclic acyl, in which the preferable one is aliphatic acyl such as lower alkanoyl (e.g. formyl, acetyl, propionyl, butyryl, hexanoyl, etc.).

Suitable "mono or di or trihalo(lower)alkyl" may include chloromethyl, fluoromethyl, difluoromethyl, dichloromethyl, trifluoromethyl, trifluoromethylpropyl, and the like.

Suitable "hydroxy(lower)alkyl" may include hydroxymethyl, hydroxyetyl, and the like.

Suitable "oxo(lower)alkyl" may include formyl, formylmethyl, formylethyl, and the like.

Suitable "esterified carboxy" may include lower alkoxycarbonyl (e.g. methoxycarbonyl, ethoxycarbonyl, etc.), and the like.

Suitable "imino-protective group" may include conventional one, and the preferable example thereof is ar(lower)alkyl such as mono-(or di- or tri-)phenyl(lower)alkyl (e.g. benzyl, benzhydryl, trityl, etc.), acyl such as lower alkoxycarbonyl (e.g. tert-butoxycarbonyl, etc.), lower alkanesulfonyl (e.g. mesyl, etc.), arenesulfonyl (e.g. tosyl, etc.), and the like, in which the most preferred one is trityl.

The term "condensed on uncondensed imidazolyl" means 1H-imidazol-1-yl which may be condensed with aromatic or heterocyclic ring, and such group may include benzene, naphthalene, 5 or 6- membered aromatic heteromonocyclic group such as 5 or 6- membered aromatic heteromonocyclic group containing 1 to 2- nitrogen atom(s) (e.g. pyrrole, imidazole, pyrazole, pyridine, pyrimidine, etc.), 5 or 6-membered aromatic heteromonocyclic group containing 1 oxygen atom (e.g. furan, etc.), 5 or 6- membered aromatic heteromonocyclic group containing 1 sulfur atom (e.g. thiophene, etc.), and the like.

Suitable substituent in the term "condensed or uncondensed imidazolyl which may have suitable substituent(s)" is conventional one used in a pharmaceutical field and may include lower alkyl, halogen, lower alkoxy, hydroxy(lower)alkyl as mentioned above, respectively; optionally esterified carboxy such as carboxy, lower alkoxycarbonyl (e.g. ethoxycarbonyl, etc.); and the like.

Particularly, the preferred embodiment of

N
| is as follows. 2-lower alkyl-3H-imidazo[4,5-b]pyridin-3-yl (e.g. 2-ethyl-3H-imidazo[4,5-b]pyridin-3-yl, 2-propyl-3H-imidazo[4,5-b]pyridin-3-yl, 2-butyl-3H-imidazo[4,5-b]pyridin-3-yl, etc.); lower)alkyl-3H-imidazo[4,5-b]pyridin-3-yl e.g. 2-ethyl-7-methyl-3H-imidazo[4,5-b]pyridin-3-yl, -methyl-2-propyl-3H-imidazo[4,5-b]pyridin-3-yl, -butyl-7-methyl-3H-imidazo[4,5-b]pyridin-3-yl, etc.), 2,5,7-tri(lower)alkyl-3H-imidazo[4,5-b]pyridin-3-yl (e.g. -ethyl-5,7-dimethyl-3H-imidazo[4,5-b]pyridin-3-yl, 5,7-dimethyl-2-propyl-3H-imidazo[4,5-b]pyridin-3-yl, etc.); 5-halo-2-lower alkyl-3H-imidazo[4,5-b]pyridin-3-yl (e.g. 2-butyl-5-chloro-3H-imidazo[4,5-b]pyridin-3-yl, etc.), 5-lower alkoxy-2-lower alkyl-3H-imidazo[4,5-b]pyridin-3-yl (e.g. -butyl-5-methoxy-3H-imidazo[4,5-b]pyridin-3-yl, etc.), -lower alkoxycarbonyl-2-lower alkyl-1H-benzimidazol-1-yl (e.g. 2-butyl-6-ethoxycarbonyl-1H-benzimidazol-1-yl, etc.), 2-lower alkyl-3H-imidazo[4,5-d]pyrimidin-3-yl (e.g. -butyl-3H-imidazo[4,5-d]pyrimidin-3-yl, etc.), 2-lower alkyl-1H-thieno[3,4-d]imidazol-1-yl (e.g. 2-butyl-1H-thieno[3,4-d]imidazol-1-yl, etc.), 2-lower alkyl-4-halo-5-hydroxy(lower)alkyl-1H-imidazol-1-yl (e.g. 2-butyl-4-chloro-5-hydroxymethyl-1H-imidazol-1-yl, etc.) and more preferably 2-lower alkyl-3H-imidazo[4,5-b]pyridin-3-yl, 2,7-di(lower)alkyl-3H-imidazo[4,5-b]pyridin-3-yl and 2,5,7-tri(lower)alkyl-3H-imidazo[4,5-b]pyridin-3-yl.

Suitable "acid residue" may include halogen (e.g. fluoro, chloro, bromo, iodo),acyloxy (e.g. acetoxy, tosyloxy, mesyloxy, etc.) and the like.

The preferred embodiment of the heterocyclic derivatives (I) of the present invention can be represented by the following chemical formula:

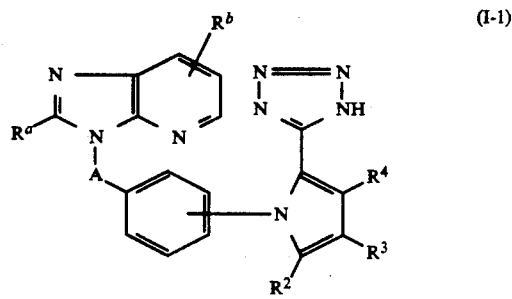

(I-1)

wherein
$R^a$ is lower alkyl,
$R^b$ is hydrogen or lower alkyl,
A is lower alkylene, and
$R^2$, $R^3$ and $R^4$ are each hydrogen, halogen or nitro; or $R^2$ and $R^3$ are linked together to form 1,3-butadienylene, in which lower alkyl, lower alkylene and halogen are each the same as those mentioned above.

Also, the preferred embodiment of the compound (I) can be represented by the following formula.

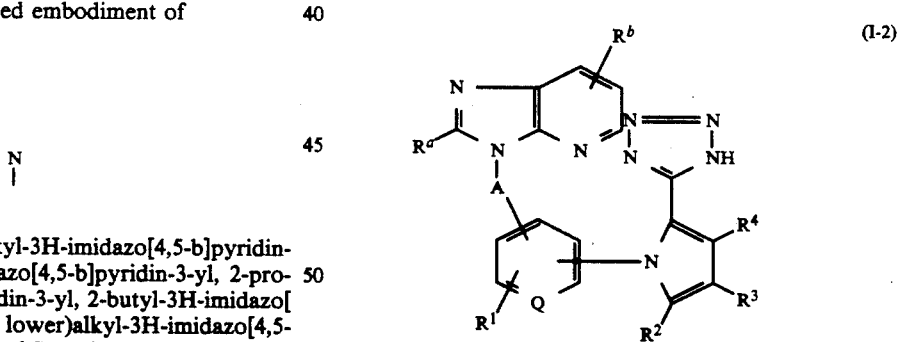

(I-2)

wherein
$R^a$ is lower alkyl,
$R^b$ is hydrogen or lower alkyl,
$R^1$ is hydrogen, halogen, nitro, lower alkoxy, amino or acylamino,
A is lower alkylene,
Q is CH or N, and
$R^2$, $R^3$ and $R^4$ are each hydrogen, halogen or nitro; or $R^2$ and $R^3$ are linked together to form 1,3-butadienylene, in which lower alkyl, halogen, lower alkoxy, acylamino and lower alkylene are each the same as those mentioned above.

Also, the preferred embodiment of the compound (I) can be represented by the following formula.

(I-3)

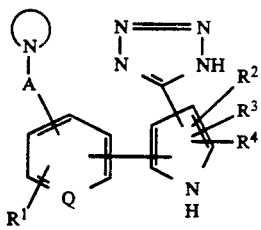

wherein
R[1] is hydrogen, halogen, nitro, lower alkyl, lower alkoxy, amino or acylamino,
R[2], R[3] and R[4] are each hydrogen, halogen, nitro, cyano, lower alkyl or lower alkenyl; or
R[2] and R[3] are linked together to form 1,3-butadienylene,
A is lower alkylene,
Q is CH or N, and

is condensed or uncondensed imidazolyl which may have suitable substituent(s),
in which each of these definitions is the same as those mentioned above, and more preferred example of

may be: 2-lower alkyl-3H-imidazo[4,5-b]pyridin-3-yl (e.g. 2-propyl-3H-imidazo[4,5-b]pyridin-3-yl, 2-butyl-3H-imidazo[4,5-b]pyridin-3-yl, etc.); 2,7-di(lower)alkyl-3H-imidazo[4,5-b]pyridin-3-yl (e.g. 7-methyl-2-propyl-3H-imidazo[4,5-b]pyridin-3-yl, 2-butyl-7-methyl-3H-imidazo[4,5-b]pyridin-3-yl, etc.), 5-halo-2-lower alkyl-3H-imidazo[4,5-b]pyridin-3-yl (e.g. 2-butyl-5-chloro-3H-imidazo[4,5-b]pyridin-3-yl, etc.), 5-lower alkyl-2-lower alkyl-3H-imidazo[4,5-b]pyridin-3-yl (e.g. 2-butyl-5-methoxy-3H-imidazo[4,5-b]pyridin-3-yl, etc.), 6-lower alkoxycarbonyl-2-lower alkyl-1H-benzimidazol-1-yl (e.g. 2-butyl-6-ethoxycarbonyl-1H-benzimidazol-1-yl, etc.), 2-lower alkyl-3H-imidazo[4,5-d]pyrimidin-3-yl (e.g. 2-butyl-3H-imidazo[4,5-d]pyrimidin-3-yl, etc.), 2-lower alkyl-1H-thieno[3,4-d]imidazol-1-yl (e.g. 2-butyl-1H-thieno[3,4-d]imidazol-1-yl, etc.), 2-lower alkyl-4-halo-5-hydroxy(lower)alkyl-1H-imidazol-1-yl (e.g. 2-butyl-4-chloro-5-hydroxymethyl-1H-imidazol-1-yl, etc.); and more preferred example of its substituent may be: lower alkyl, halogen, lower alkoxy, optionally esterified carboxy as explained above, respectively.

Also, the preferred embodiment of the compound (I) can be represented by the following formula.

(I-4)

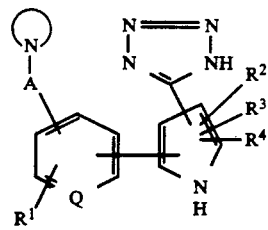

wherein
R[1] is hydrogen, halogen, nitro, lower alkyl, lower alkoxy, amino or acylamino,
R[2], R[3] and R[4] are each hydrogen, halogen, nitro, cyano, lower alkyl, lower alkenyl, lower alkylthio, dihalo(lower)alkyl, oxo(lower)alkyl or hydroxy(lower)alkyl; or
R[2] and R[3] are linked together to form 1,3-butadienylene,
A is lower alkylene,
Q is CH or N, and

is condensed or uncondensed imidazolyl which may have suitable substituent(s), in which each of these definitions is the same as those mentioned above, and more preferred example of

may be: 2-lower alkyl-3H-imidazo[4,5-b]pyridin-3-yl (e.g. 2-propyl-3H-imidazo[4,5-b]pyridin-3-yl, 2-butyl-3H-imidazo[4,5-b]pyridin-3-yl, etc.); 2,7-di(lower)alkyl-3H-imidazo[4,5-b]pyridin-3-yl (e.g. 7-methyl-2-propyl-3H-imidazo[4,5-b]pyridin-3-yl, 2-butyl-7-methyl-3H-imidazo[4,5-b]pyridin-3-yl, etc.), 2,5,7-tri(lower)alkyl-3H-imidazo[4,5-b]pyridin-3-yl (e.g. 2-ethyl-5,7-dimethyl-3H-imidazo[4,5-b]pyridin-3-yl, etc.); 5-halo-2-lower alkyl-3H-imidazo[4,5-b]pyridin-3-yl (e.g. 2-butyl-5-chloro-3H-imidazo[4,5-b]pyridin-3-yl, etc.), 5-lower alkoxy-2-lower alkyl-3H-imidazo[4,5-b]pyridin-3-yl (e.g. 2-butyl-5-methoxy-3H-imidazo[4,5-b]pyridin-3-yl, etc.), 6-lower alkoxycarbonyl-2-lower alkyl-1H-benzimidazol-1-yl (e.g. 2-butyl-6-ethoxycarbonyl-1H-benzimidazol-1-yl, etc.), 2-lower alkyl-3H-imidazo[4,5-d]pyrimidin-3-yl (e.g. 2-butyl-3H-imidazo[4,5-d]pyrimidin-3-yl, etc.), 2-lower alkyl-1H-thieno[3,4-d]imidazol-1-yl (e.g. 2-butyl-1H-thieno[3,4-d]imidazol-1-yl, etc.), 2-lower alkyl-4-halo-5-hydroxy(lower)alkyl-1H-imidazol-1-yl (e.g. 2-butyl-4-chloro-5-hydroxymethyl-1H-imidazol-1-yl, etc.); and more preferred example of its substituent may be: lower alkyl, halogen, lower alkoxy, optionally esterified carboxy as mentioned above, respectively.

Further, the preferred embodiment of the compound (I) can be represented by the following formula.

(I-5)

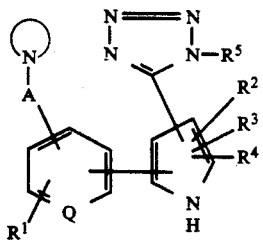

wherein
R¹ is hydrogen, halogen, nitro, lower alkyl, lower alkoxy, amino or acylamino,
R², R³ and R⁴ are each hydrogen, halogen, nitro, cyano, lower alkyl, lower alkenyl, lower alkylthio, mono or di or trihalo(lower)alkyl, oxo(lower)alkyl, hydroxy(lower)alkyl or optionally esterified carboxy; or
R² and R³ are linked together to form 5 1,3-butadienylene,
R⁵ is hydrogen or imino-protective group,
A is lower alkylene,
Q is CH or N, and

is condensed or uncondensed imidazolyl which may have suitable substituent(s),
in which each of these definitions is the same as those mentioned above, and more preferred example of

may be: 2-lower alkyl-3H-imidazo[4,5-b]pyridin-3-yl (e.g. 2-propyl-3H-imidazo[4,5-b]pyridin-3-yl, 2-butyl-3H-imidazo[4,5-b]pyridin-3-yl, etc.); 2,7-di(lower)alkyl-3H-imidazo[4,5-b]pyridin-3-yl (e.g. 7-methyl-2-propyl-3H-imidazo[4,5-b]pyridin-3-yl, 2-butyl-7-methyl-3H-imidazo[4,5-b]pyridin-3-yl, etc.), 2,5,7-tri(lower)alkyl-3H-imidazo[4,5-b]pyridin-3-yl (e.g. 2-ethyl-5,7-dimethyl-3H-imidazo[4,5-b]pyridin-3-yl, etc.); 5-halo-2-lower alkyl-3H-imidazo[4,5-b]pyridin-3-yl (e.g. 2-butyl-5-chloro-3H-imidazo[4,5-b]pyridin-3-yl, etc.), 5-lower alkoxy-2-lower alkyl-3H-imidazo[4,5-b]pyridin-3-yl (e.g. 2-butyl-5-methoxy-3H-imidazo[4,5-b]pyridin-3-yl, etc.), 6-lower alkoxycarbonyl-2-lower alkyl-1H-benzimidazol-1-yl (e.g. 2-butyl-6-ethoxycarbonyl-1H-benzimidazol-1-yl, etc.), 2-lower alkyl-3H-imidazo[4,5-d]pyrimidin-3-yl (e.g. 2-butyl-3H-imidazo[4,5-d]pyrimidin-3-yl, etc.), 2-lower alkyl-1H-thieno[3,4-d]imidazol-1-yl (e.g. 2-butyl-1H-thieno[3,4-d]imidazol-1-yl, etc.), 2-lower alkyl-4-halo-5-hydroxy(lower)alkyl-1H-imidazol-1-yl (e.g. 2-butyl-4-chloro-5-hydroxymethyl-1H-imidazol-1-yl, etc.); and more preferred example of its substituent may be: lower alkyl, halogen, lower alkoxy optionally esterified carboxy as mentioned above, respectively.

Still further, the preferred embodiment of the compound (I) can be represented by the following formula.

(I-6)

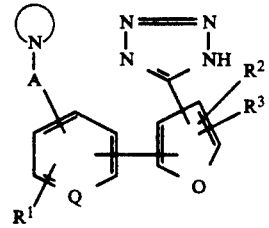

wherein
R¹ is hydrogen, halogen, nitro, lower alkyl, lower alkoxy, amino or acylamino,
R² and R³ are each hydrogen, halogen, nitro, cyano, lower alkyl or lower alkenyl; or
R² and R³ are linked together to form 1,3-butadienylene,
A is lower alkylene,
Q is CH or N, and

is condensed or uncondensed imidazolyl which may have suitable substituent(s), in which each of these definitions is the same as those mentioned above, and more preferred example of

may be: 2-lower alkyl-3H-imidazo[4,5-b]pyridin-3-yl (e.g. 2-propyl-3H-imidazo[4,5-b]pyridin-3-yl, 2-butyl-3H-imidazo[4,5-b]pyridin-3-yl, etc.); 2,7-di(lower)alkyl-3H-imidazo[4,5-b]pyridin-3-yl (e.g. 7-methyl-2-propyl-3H-imidazo[4,5-b]pyridin-3-yl, 2-butyl-7-methyl-3H-imidazo[4,5-b]pyridin-3-yl, etc.), 5-halo-2-lower alkyl-3H-imidazo[4,5-b]pyridin-3-yl (e.g. 2-butyl-5-chloro-3H-imidazo[4,5-b]pyridin-3-yl, etc.), 5-lower alkyl-2-lower alkyl-3H-imidazo[4,5-b]pyridin-3-yl e.g. 2-butyl-5-methoxy-3H-imidazo[4,5-b]pyridin-3-yl, etc.), 6-lower alkoxycarbonyl-2-lower alkyl-1H-benzimidazol-1-yl (e.g. 2-butyl-6-ethoxycarbonyl-1H-benzimidazol-1-yl, etc.), 2-lower alkyl-3H-imidazo[4,5-d]pyrimidin-3-yl (e.g. 2-butyl-3H-imidazo[4,5-d]pyrimidin-3-yl, etc.), 2-lower alkyl-1H-thieno[3,4-d]imidazol-1-yl (e.g. 2-butyl-1H-thieno[3,4-d]imidazol-1-yl, etc.), 2-lower alkyl-4-halo-5-hydroxy(lower)alkyl-1H-imidazol-1-yl (e.g. 2-butyl-4-chloro-5-hydroxymethyl-1H-imidazol-1-yl, etc.); and more preferred example of its substituent may be: lower alkyl, halogen, lower alkoxy, optionally esterified carboxy as mentioned above, respectively.

Particularly, the preferred compound (I) of the present invention is represented by the following formula:

(I-7)

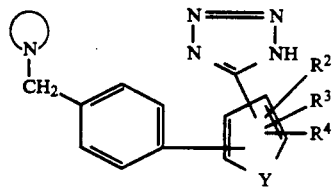

wherein
R², R³ and R⁴ are each hydrogen, halogen, nitro, cyano, lower alkyl, lower alkenyl, lower alkylthio, mono or di or trihalo(lower)alkyl, oxo(lower)alkyl, hydroxy(lower)alkyl or optionally esterified carboxy (more preferably carboxy or lower alkoxycarbonyl); or R² and R³ are linked together to form 1,3-butadienylene, Y is NH, O or S and

is 2-lower alkyl-3H-imidazo[4,5-b]pyridin-3-yl, 2,7-di(lower)alkyl-3H-imidazo[4,5-b]pyridin-3-yl, 2,5,7-tri(lower)alkyl-3H-imidazo[4,5-b]pyridin-3-yl, 5-halo-2-lower alkyl-3H-imidazo[4,5-b]pyridin-3-yl, 5-lower alkoxy-2-lower alkyl-3H-imidazo[4,5-b]pyridin-3-yl, 6-lower alkoxycarbonyl-2-lower alkyl-1H-benzimidazol-1-yl, 2-lower alkyl-3H-imidazo[4,5-d]pyrimidin-3-yl, 2-lower alkyl-1H-thieno[3,4-d]imidazol-1-yl or 2-lower alkyl-4-halo-5-hydroxy(lower)alkyl-1H-imidazol-1-yl (more preferably, 2-lower alkyl-3H-imidazo[4,5-b]pyridin-3-yl, 2,7-di(lower)alkyl-3H-imidazo[4,5-b]pyridin-3-yl or 2,5,7-tri(lower)alkyl-3H-imidazo[4,5-b]pyridin-3-yl), and further, more preferred embodiment of a group of the formula.

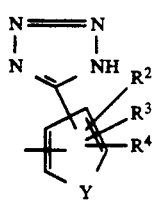

is represented by the following formula:

1)

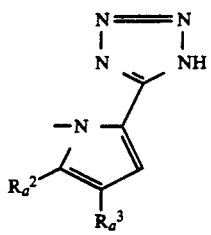

wherein $R_a^2$ is hydrogen, halogen, cyano, lower alkyl or lower alkylthio, and $R_a^3$ is hydrogen, halogen, nitro, lower alkyl, lower alkenyl, trihalo(lower)alkyl, oxo(lower)alkyl, hydroxy(lower)alkyl or lower alkoxycarbonyl;

2)

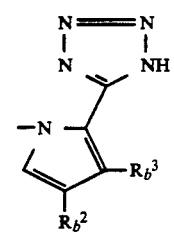

wherein $R_b^2$ and $R_b^3$ are each halogen;

3)

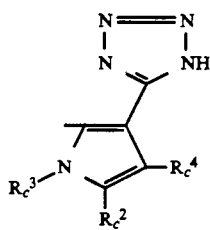

wherein $R_c^2$ is hydrogen, halogen or lower alkyl, $R_c^3$ is lower alkyl, and $R_c^4$ is hydrogen or halogen;

4)

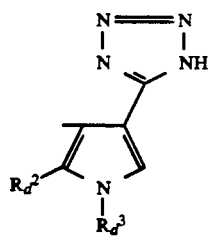

wherein $R_d^2$ is hydrogne, halogen or lower akyl, and $R_d^3$ is lower alkyl;

5)

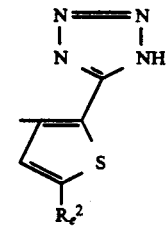

wherein $R_e^2$ is hydrogen or halogen; or

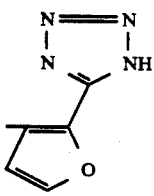

and the most preferred one is:

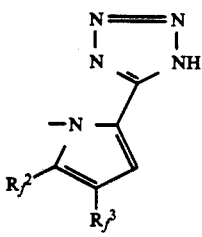

wherein $R_f^2$ and $R_f^3$ are each hydrogen, lower alkyl or halogen.

The processes for preparing the object compound (I) of the present invention are explained in detail in the following.

Process 1

The object compound (I) or a salt thereof can be prepared by subjecting the compound (II) to the formation reaction of a tetrazole group.

The agent to be used in the present reaction may include conventional ones which is capable of converting a cyano group to a tetrazolyl group such as metal azide, for example, alkali metal azide (e.g., potassium azide, sodium azide etc.), tri(lower)alkyltin azide (e.g. trimethyltin azide, etc.), triaryltin azide (e.g. triphenyltin azide, etc.), or the like.

The present reaction is usually carried out in the presence of a base such as tri(lower)alkylamine (e.g. triethylamine, etc.), and the like, or 1,3-dimethyl-2-imidazolidinone, and the like.

The present reaction is usually carried out in a solvent such as xylene, dioxane, chloroform, methylene chloride, 1,2-dichloroethane, tetrahydrofuran, pyridine, acetonitrile, dimethylformamide or any other solvent which does not adversely affect the reaction.

The reaction temperature is not critical and the reaction is usually carried out under warming or heating, preferably under heating.

Further, the compound (I) wherein $R^1$ is amino can be prepared by reducing the corresponding nitro compound in a conventional manner, and the compound (I) wherein $R^1$ is acylamino can be prepared by acylating the amino compound obtained above in a conventional manner.

And further, the present reaction includes, within its scope, the case that the dihalo(lower)alkyl group on $R^2$, $R^3$ or $R^4$ is transformed to the oxo(lower)alkyl group during the reaction or at the post-treating step of the present process.

Process 2

The object compound (I-b) or a salt thereof can be prepared by subjecting the compound (I-a) or a salt thereof to reduction.

The reduction may include, for example, chemical reduction with an alkali metal borohydride (e.g. sodium borohydride, etc.), and catalytic reduction with palladium catalysts (e.g. palladium on carbon, etc.), and the like.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out under cooling to heating.

Process 3

The object compound (I) or a salt thereof can be prepared by reacting the compound (III) or a salt thereof with the compound (IV) or a salt thereof.

The present reaction is usually carried out in the presence of a base such as alkyl lithium (e.g. n-butyl lithium, etc.), alkali metal hydride (e.g. sodium hydride, potassium hydride, etc.), di(lower)alkylamine (e.g. diisopropylamine, etc.), tri(lower)alkylamine (e.g. trimethylamine, triethylamine, etc.), pyridine or its derivative (e.g. picoline, lutidine, 4-dimethylaminopyridine, etc.), or the like.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

The reaction temperature is not critical and the reaction is usually carried out under cooling, at ambient temperature or under heating.

Process 4

The object compound (I-d) or a salt thereof can be prepared by subjecting the compound (I-c) or a salt thereof to removal reaction of the imino-protective group.

Suitable method for this removal may include conventional one which is capable of removing an imino-protective group on a tetrazolyl group such as hydrolysis, reduction, or the like. The hydrolysis is preferably carried out in the presence of the base or an acid.

Suitable base may include, for example, an inorganic base such as alkali metal hydride (e.g. sodium hydroxide, potassium hydroxide, etc.), alkaline earth metal hydroxide (e.g. magnesium hydroxide, calcium hydroxide, etc.), alkali metal carbonate, (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate [e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,-2]octane, 1,5-diazabicyclo[5,4,0]undecene-5 or the like. The hydrolysis using a base is often carried out in water or a hydrophilic organic solvent or a mixed solvent thereof.

Suitable acid may include an organic acid (e.g. formic acid acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and the reaction is usually carried out at ambient temperature or under warming or heating.

The starting compounds (II), (III) and (IV) are new and can be prepared by the methods of Preparations mentioned below or a similar manner thereto or a conventional manner.

The object compound (I) of the present invention can be isolated and purified in a conventional manner, for example, extraction precipitation, fractional crystallization, recrystallization, chromtography, and the like.

The object compound (I) thus obtained can be converted to its salt by a conventional method.

The object compound (I) of the present invention exhibits angiotensin antagonism such as vasodilating activity and is useful as an angiotensin II antagonist and effective to various angiotensin II mediated diseases such as hypertension (e.g. essential hypertension, renal hypertension, etc.), heart failure, and the like.

Further, it is expected that the object compounds of the present invention are useful as therapeutical and/or preventive agents for cardiopathy (e.g. angina pectoris, arrhythmia, myocardial infarction, etc.), hyperaldosteronism, cerebral vascular diseases, senile dementia, ophthalimic diseases (e.g. glaucoma, etc.), and the like; and diagnostic agents to test the renin angiotensin system.

In order to illustrate the usefulness of the object compounds (I), pharmacological activity of representative compounds of the present invention is shown below.

[1] Test Compound

① 3-[4-[4-Bromo-2-(1H-tetrazol-5-yl)-1-pyrrolyl]benzyl]-2-butyl-7-methyl-3H-imidazo[4,5-b]pyridine (hereinafter referred to as Compound ①)

[2] Inhibition by the antagonist of contractile response to angiotensin II in excised guinea pig ileum Test Method Male guinea pigs weighing 300 g to 500 g were sacrificed by decapitation and the ileum were excised. Longitudial strips of the ileum (length: 2 cm) were placed in a 25 ml organ bath containing Tyrode's solution of the following composition (mM): NaCl, 137; KCl, 2.7; $CaCl_2$, 1.8; $MgCl_2$, 1.1; $NaH_2PO_4$, 0.4; $NaHCO_3$, 12; Glucose, 5.6.

The bath was maintained at 37° C. and bubbled with 95% $O_2$+5% $CO_2$. The strips was stretched with a resting force of 0.5 g, and the isometric contraction were recorded via force development transducer on an ink-writing recorder. The preparation was equilibrated in Tyrode's solution mentioned above for 30 minutes, and then exposed to atropine ($3.2 \times 10^{-7}$ g/ml) Five minutes later, the response for angiotensin II ($1 \times 10^{-8}$ g/ml) was obtained and the preparation was washed a few times. This procedure was repeated twice. After the last response for angiotensin II was obtained (control response), the preparation was washed, and the response for angiotensin II ($10^{-8}$ g/ml) was obtained in the presence of the test compound The concentration of the test compound were $10^{-7}$, $10^{-8}$, $10^{-9}$, $10^{-10}$ M. The test compound were added 3 minutes prior to adding angiotensin II. Atropine was also added 5 minutes prior to adding angiotensin II. The inhibition of the test compound for angiotensin II contraction were expressed as a percentage change to control response, and $IC_{50}$ (M) was calculated.

[3] Test Result

| Compound | $IC_{50}$ (M) |
| --- | --- |
| ① | $1.70 \times 10^{-9}$ |

For therapeutic or preventive administration, the object compound (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical prepartion may be in solid form such as tablet, granule, powder, capsule, or liquid form such as solution, suspension, syrup, emulsion lemonade and the like.

If needed, there may be included in the above preparations auxiliary substances, stabilizing agents, wetting agents and other commonly used additives such as lactose, citric acid, tartaric acid, stearic acid, magnesium stearate, terrra alba, sucrose, corn starch, talc, gelatin, agar, pectin, peanut oil, olive oil, cacao butter, ethylene glycol, and the like.

While the dosage of the comound (I) may vary from and also depend uon the age, conditions of the patient, a kind of diseases or conditions, a king of the compound (I) to be applied, etc. In general amounts between 0.01 mg of about 500 mg or even more per day may be administered to a patient. An average single dose of about 0.05 mg, 0.1 mg, 0.25 mg, 0.5 mg, 1mg, 20 mg, 50 mg, 100 mg of the object comopund (I) of the present invention may be used in treating diseases.

The following Preparations and Examples are given for the purpose of illustrating the present invention.

Preparation 1

To a solution of 1-(4-methylphenyl)pyrrole-2-carbonitrile (1.274 g) in tetrahydrofuran (25 ml) was added N-bromosuccinimide (1.776 g) in several portions at ambient temperature. After being stirred for 3 hours at the same temperature, the mixture was concentrated in vacuo. The residue was treated with diethyl ether. The precipitates were removed by filtration and washed with a small amounts of diethyl ether. The filtrates were concentrated in vacuo to give an oily residue, which was purified by silica gel column chromatography (elution by 40% dichloromethane in n-hexane) to yield 4-bromo-1-(4-methylphenyl)pyrrole-2-carbonitrile (1.78 g) as a solid.

mp: 55°–59.5° C.

NMR ($CDCl_3$, δ): 2.42 (3H, s), 6.93 (1H, d, J=2.3 Hz), 7.04 (1H, d, J=2.3 Hz), 7.29 (5H, s)

Preparation 2

To a solution of 1-(4-methylphenyl)pyrrole (1 g) in tetrahydrofuran (50 ml) was added N-chlorosuccinimide (850 mg) in one portion at −78° C. under nitrogen atmosphere. The mixture was warmed to 10° C., stirred for one hour, and then concentrated in vacuo. The residue was purified by flash column chromatography on silica gel to yield 2-chloro-1-(4-methylphenyl)pyrrole (1.2 g) as an oil. (This product was a mixture of the starting material and the desired product and used to the next reaction furthermore without purification.)

Preparation 3

Phosphoryl chloride (747 μl) was added dropwise to N,N-dimethylformamide (7 ml) at 5° C. The mixture was stirred at 5° C. for 15 minutes and at ambient temperature for 15 minutes. To the mixture was added a solution of 2-chloro-1-(4-methylphenyl)pyrrole (1.2 g) in N,N-dimethylformamide (7 ml) at ambient temperature. The mixture was stirred at the same temperature for one hour and at 50° C. for 2.5 hours. After cooled to ambient temperature, the mixture was treated with saturated aqueous sodium bicarbonate solution. The separated oil was extracted with ethyl acetate. The organic layer was washed with water, dried, and concentrated in vacuo. The residue was column chromatographed on silica gel to yield 5-chloro-1-(4-methylphenyl)pyrrole-2-carbaldehyde (377 mg) as a solid.

NMR (CDCl$_3$, δ): 2.44 (3H, s), 6.33 (1H, d, J=4.5 Hz), 7.09 (1H, d, J=4.5 Hz), 7.18 (2H, d, J=8.0 Hz), 7.31 (2H, d, J=8.0 Hz), 9.32 (1H, s)

Preparation 4

A mixture of 5-chloro-1-(4-methylphenyl)pyrrole-2-carbaldehyde (365 mg), hydroxylamine hydrochloride (173 mg), and sodium acetate (204 mg) in 60% aqueous ethanol (6 ml) was stirred at 60° C. for one hour. The mixture was concentrated in vacuo. The residue was dissolved in ethyl acetate. The mixture was washed with water, dried, and concentrated in vacuo to give a residue (450 mg) of 5-chloro-1-(4-methylphenyl)pyrrole-2-carbaldehyde oxime. A mixture of the residue and sodium acetate (30 mg) in acetic anhydride (5 ml) was stirred at 160° C. for one and half hours under nitrogen atmosphere. The reaction mixture was concentrated in vacuo. The residue was purified by silica gel column chromatography (eluted by ethyl acetate:n-hexane =1/15) to yield 5-chloro-1-(4-methylphenyl)pyrrole-2-carbonitrile (325 mg) as an oil.

NMR (CDCl$_3$, δ): 2.45 (3H, s), 6.25 (1H, d, J=4.5 Hz), 6.90 (1H, d, J=4.5 Hz), 7.23 (2H, d, J=8.0 Hz), 7.34 (2H, d, J=8 Hz)

Preparation 5

To a solution of 1-(4-methylphenyl)pyrrole-2-carbonitrile (1.092 g) in a mixture of ethanol (10 ml) and 1,4-dioxane (10 ml) was added N-chlorosuccinimide (1.862 g) in one portion at ambient temperature. The mixture was stirred for 2.5 hours at the same temperature and then water (30 ml) was added therein. The separated oil was extracted with diethyl ether. The extract was washed with water, dried, and concentrated in vacuo. The yellow residue was crystallized from n-hexane to yield 3,4-dichloro-1-(4-methylphenyl)pyrrole-2-carbonitrile (1.28 g).

mp: 85°-86° C.

NMR (CDCl$_3$, δ): 2.45 (3H, s), 6.91 (1H, s), 7.23 and 7.34 (4H, ABq, J=7.5 Hz)

Preparation 6

To a solution of 1-(4-methylphenyl)pyrrole-2-carbonitrile (1.0 g) in acetic anhydride (4 ml) was added nitric acid (231 μl, 94%) dropwise at 5° C. The mixture was stirred at the same temperature for 3 hours and then poured into ice water. The pH was adjusted to 5-7 by the addition of saturated aqueous sodium bicarbonate solution. The separated oil was extracted with ethyl acetate. The organic layer was washed with saturated aqueous sodium bicarbonate solution, water and brine, dried, and evaporated under reduced pressure. The residue was purified by silica gel column chromatography to yield 1-(4-methylphenyl)-4-nitropyrrole-2-carbonitrile (471 mg) as a solid.

NMR (CDCl$_3$, δ): 2.47 (3H, s), 7.36 (4H, s), 7.49 (1H, d, J=1.5 Hz), 7.83 (1H, d, J=1.5 Hz)

Preparation 7

A mixture of 3,4-dichloro-1-(4-methylphenyl)pyrrole-2-carbonitrile (1.25 g), 2,2'-azobisisobutyronitrile (10 mg) and N-bromosuccinimide (1.068 g) in carbon tetrachloride (25 ml) was refluxed for 3 hours, cooled to ambient temperature, and filtered. The filtrate was concentrated in vacuo. The residue was crystallized from 10% ethyl acetate in n-hexane to yield 1-(4-bromomethylphenyl)-3,4-dichloropyrrole-2-carbonitrile (1.01 g).

NMR (CDCl$_3$, δ): 4.53 (2H, s), 6.94 (1H, s), 7.46 and 7.58 (4H, ABq, J=7.5 Hz)

Preparation 8

The following compounds were obtained according to a similar manner to that of Preparation 7.

(1)

4-Bromo-1-(4-bromomethylphenyl)pyrrole-2-carbonitrile mp: 105°-116° C.

NMR (CDCl$_3$, δ): 4.54 (2H, s), 7.00 (1H, d, J=2.3 Hz), 7.10 (1H, d, J=2.3 Hz), 7.41 (2H, d, J=8.5 Hz), 7.55 (2H, d, J=8.5 Hz)

(2)

1-(4-Bromomethylphenyl)-5-chloropyrrole-2-carbonitrile

NMR (CDCl$_3$, δ): 4.53 (2H, s), 6.30 (1H, d, J=4.5 Hz), 6.94 (1H, d, J=4.5 Hz), 7.37 (2H, d, J=8.0 Hz), 7.57 (2H, d, J=8.0 Hz)

(3)

1-(4-Bromomethylphenyl)-4-nitropyrrole-2-carbonitrile

NMR (CDCl$_3$, δ): 4.54 (2H, s), 7.48 (2H, d, J=8.5 Hz), 7.52 (1H, d, J=1.5 Hz), 7.62 (2H, d, J=8.5 Hz), 7.88 (1H, d, J=1.5 Hz)

(4) 1-(4-Bromomethylphenyl)pyrrole-2-carbonitrile

NMR (CDCl$_3$, δ): 4.55 (2H, s), 6.37 (1H, dd, J=4.5 Hz and 3.0 Hz), 7.01 (1H, dd, J=4.5 Hz and 2.5 Hz), 7.09 (1H, dd, J=3 Hz and 2.5 Hz), 7.43 (2H, d, J=9 Hz), 7.52 (2H, d, J=9 Hz)

(5) 1-(4-Bromomethylphenyl)indole-2-carbonitrile

This compound was used to the next reaction without furthermore purification.

Preparation 9

To a solution of 2-butyl-7-methyl-3H-imidazo[4,5-b]pyridine (568 mg) in dimethyl sulfoxide (7 ml) was added sodium hydride (132 mg, 60% oil dispersion) at ambient temperature. The mixture was stirred for 40 minutes at the same temperature. To the mixture was added dropwise a solution of 1-(4-bromomethylphenyl)-3,4-dichloropyrrole-2-carbonitrile (990 mg) in dimethyl sulfoxide (3 ml). The mixture was stirred for 2 hours at ambient temperature and ice water (30 ml) was added therein. The separated oil was extracted twice with ethyl acetate. The extracts were washed with water, dried, and evaporated under reduced pressure. The residue was purified by silica gel column chromatography eluted by 50% ethyl acetate in n-hexane to give 2-butyl-3-[4-(2-cyano-3,4-dichloro-1-pyrrolyl)benzyl]-7-methyl-3H-imidazo[4,5-b]pyridine (546 mg) as an oil.

NMR (CDCl$_3$, δ): 0.91 (3H, t, J=7.5 Hz), 1.42 (2H, m), 1.76 (2H, m), 2.73 (3H, s), 2.90 (2H, t, J=7.5 Hz), 5.60 (2H, s), 6.94 (1H, s), 7.09 (1H, d, J=5 Hz), 7.31 (4H, s), 8.25 (1H, d, J=5 Hz)

Preparation 10

The following compounds were obtained according to a similar manner to that of Preparation 9.

(1)
3-[4-(4-Bromo-2-cyano-1-pyrrolyl)benzyl]-2-butyl-7-methyl-3H-imidazo[4,5-b]pyridine NMR (CDCl$_3$, δ): 0.92 (3H, t, J=7.5 Hz), 1.42 (2H, m), 1.77 (2H, m), 2.72 (3H, s), 2.88 (2H, t, J=7.5 Hz), 5.57 (2H, s), 6.97 (1H, d, J=2.3 Hz), 7.03 (1H, d, J=2.3 Hz), 7.08 (1H, d, J=5 Hz), 7.38 (2H, d, J=8.5 Hz), 7.48 (2H, d, J=8.5 Hz), 8.24 (1H, d, J=5 Hz)

(2)
2-Butyl-3-[4-(5-chloro-2-cyano-1-pyrrolyl)benzyl]-3H-imidazo[4,5-b]pyridine

NMR (CDCl, δ): 0.92 (3H, t, J=7.5 Hz), 1.32-1.52 (2H, m), 1.72-1.91 (2H, m), 2.87 (2H, t, J=7.5 Hz), 5.59 (2H, s), 6.27 (1H, d, J=4.5 Hz), 6.91 (1H, d, J=4.5 Hz), 7.28 (1H, dd, J=8.5 Hz and 5.0 Hz), 7.32 (4H, s), 8.07 (1H, dd, J=8.5 Hz and 1.0 Hz), 8.38 (1H, dd, J=5.0 Hz and 1.0 Hz)

(3)
2-Butyl-3-[4-(2-cyano-4-nitro-1-pyrrolyl)benzyl]-3H-imidazo[4,5-b]pyridine

NMR (CDCl$_3$, δ): 0.94 (3H, t, J=7.5 Hz), 1.33-1.56 (2H, m), 1.77-1.97 (2H, m), 2.90 (2H, t, J=7.5 Hz), 5.61 (2H, s), 7.31 (1H, dd, J=7.5 Hz and 4.5 Hz), 7.37 (2H, d, J=8.5 Hz), 7.45 (2H, d, J=8.5 Hz), 7.49 (1H, d, J=1.5 Hz), 7.82 (1H, d, J=1.5 Hz), 8.09 (1H, dd, J=7.5 Hz and 1Hz), 8.39 (1H, dd, J=4.5 Hz and 1.0 Hz)

(4)
2-Butyl-3-[4-(2-cyano-1-pyrrolyl)benzyl]-3H-imidazo[4,5-b]pyridine

NMR (CDCl$_3$, δ): 0.93 (3H, t, J=7.5 Hz), 1.45 (2H, m), 1.87 (2H, m), 2.88 (2H, dd, J=8 Hz and 8 Hz), 5.56 (2H, s), 6.33 (1H, dd, J=4 Hz and 3 Hz), 6.98 (1H, dd, J=4 Hz and 1Hz), 7.03 (1H, dd, J=3 Hz and 1Hz), 7.28 (1H, m), 7.29 (2H, d, J=8 Hz), 7.41 (2H, d, J=8 Hz), 8.07 (1H, dd, J=7.5 Hz and 1.5 Hz), 8.38 (1H, dd, J=4 Hz and 1.5 Hz)

(5)
2-Butyl-3-[4-(2-cyano-1-indolyl)benzyl]-3H-imidazo[4,5-b]pyridine

NMR (CDCl$_3$, δ): 0.93 (3H, t, J=7.5 Hz), 1.46 (2H, m), 1.88 (2H, m), 2.98 (2H, t, J=8 Hz), 5.66 (2H, s), 7.21-7.45 (4H, m), 7.32 (2H, d, J=8 Hz), 7.40 (1H, s), 7.48 (2H, d, J=8 Hz), 7.72 (1H, m), 8.13 (1H, dd, J=8 Hz and 1Hz), 8.46 (1H, dd, J=4.5 Hz and 1Hz)

(6)
2-Butyl-3-[4-(5-chloro-2-cyano-1-pyrrolyl)benzyl]-7-methyl-3H-imidazo[4,5-b]pyridine NMR (CDCl$_3$, δ): 0.90 (3H, t, J=6.5 Hz), 1.40 (2H, m), 1.73 (2H, m), 2.72 (3H, s), 2.87 (2H, t, J=7.5 Hz), 5.58 (2H, s), 6.24 (1H, d, J=4 Hz), 6.90 (1H, d, J=4 Hz), 7.08 (1H, d, J=5 Hz), 7.30 (4H, s), 8.25 (1H, d, J=5 Hz)

Preparation 11

A mixture of 2-amino-4-methyl-3-nitropyridine (5.0 g) and N,N-dimethylaniline (8.5 ml) was heated at 100° C. under nitrogen atmosphere. To the solution was added butyryl chloride (3.5 ml) and the mixture was stirred at 100° C. for 5 hours. After being cooled to room temperature, ethyl acetate was added to the reaction mixture. The organic layer was separated and washed successively with water and brine. The solution was dried over magnesium sulfate and the solvent was evaporated in vacuo. The residue was washed with n-hexane to give 2-butyrylamino-4-methyl-3-nitropyridine (7.0 g).

mp: 92.5°-99° C.

NMR (CDCl$_3$, δ): 1.01 (3H, t, J=7.5 Hz), 1.64-1.85 (2H, m), 2.43 (2H, t, J=7.5 Hz), 2.48 (3H, s), 7.10 (1H, d, J=5.0 Hz), 8.26 (1H, br s), 8.35 (1H, d, J=5.0 Hz)

Preparation 12

A solution of 2-butyrylamino-4-methyl-3-nitropyridine (7.0 g) and iron powder (17.5 g) in a mixture of acetic acid (14 ml) and ethanol (100 ml) was stirred at 90° C. for 3 hours under nitrogen atmosphere. After being cooled to room temperature, the reaction mixture was filtered through Celite and the filtrate was evaporated in vacuo. Ethyl acetate and saturated aqueous sodium hydrogencarbonate were added to the residue until pH 7~8 and the resulting suspension was filtered through Celite. The organic layer of the filtrate was separated, washed with brine and dried over magnesium sulfate. The solvent was evaporated in vacuo and the residue was purified with silica gel column chromatography (eluent: ethyl acetate) to give 7-methyl-2-propyl-3H-imidazo[4,5-b]pyridine (3.6 g).

mp: 108°-111° C.

NMR (CDCl$_3$, δ): 1.09 (3H, t, J=7.5 Hz), 1.90-2.12 (2H, m), 2.72 (3H, s), 3.06 (2H, t, J=7.5 Hz), 7.07 (1H, d, J=5.0 Hz), 8.19 (1H, d, J=5.0 Hz)

Preparation 13

2-Bromo-4-methylaniline (15.0 g), 2,5-dimethoxytetrahydrofuran (10.7 g) and acetic acid (81 ml) were combined under nitrogen atmosphere. The reaction mixture was stirred at 90° C. for 1.5 hours. After being cooled to room temperature, the reaction mixture was concentrated in vacuo with toluene. n-Hexane (300 ml) was added to the residue, and the suspension was filtered through Celite. Then silica gel was added to the filtrate with stirring until the colour of the solution disappeared. The suspension was filtered and the filtrate was concentrated in vacuo to give 1-(2-bromo-4-methylphenyl)pyrrole (16.1 g).

NMR (CDCl$_3$, δ): 2.38 (3H, s), 6.31 (2H, t, J=3.0 Hz), 6.83 (2H, t, J=3.0 Hz), 7.12-7.22 (2H, m), 7.51 (1H, d, J=1.0 Hz)

Preparation 14

The following compounds were obtained according to a similar manner to that of Preparation 13.

(1) 1-(3-Fluoro-4-methylphenyl)pyrrole

NMR (CDCl$_3$, δ): 2.39 (3H, d, J=2.5 Hz), 6.32 (2H, m), 7.02-7.26 (5H, m)

(2) 5-Methyl-2-(1-pyrrolyl)pyridine mp: 54.5°-62° C.
NMR (CDCl$_3$, δ): 2.33 (3H, s), 6.35 (2H, t, J=2.0 Hz), 7.22 (1H, d, J=8.5 Hz), 7.48 (2H, t, J=2.0 Hz), 7.56 (1H, dd, J=8.5 Hz, 1.5 Hz), 8.25 (1H, d, J=1.5 Hz)

(3) 1-(3-Chloro-4-methylphenyl)pyrrole mp: 48°-50° C.
NMR (CDCl$_3$, δ): 2.39 (3H, s), 6.34 (2H, dd, J=4 Hz, 4 Hz), 7.05 (2H, dd, J=4 Hz, 4 Hz), 7.19 (1H, dd, J=8 Hz, 2 Hz), 7.26 (1H, d, J=8 Hz), 7.40 (1H, d, J=2 Hz)

(4) 1-(3-Methoxy-4-methylphenyl)pyrrole

NMR (CDCl$_3$, δ): 2.23 (3H, s), 3.87 (3H, s), 6.33 (2H, t, J=2 Hz), 6.84 (1H, d, J=2 Hz), 6.88 (1H, dd, J=8 Hz, 2 Hz), 7.06 (2H, t, J=2 Hz), 7.16 (1H, d, J=8 Hz)

(5) 1-(4-Methyl-2-nitrophenyl)pyrrole

NMR (CDCl$_3$, δ): 2.48 (3H, s), 6.35 (2H, t, J=2 Hz), 6.78 (2H, t, J=2 Hz), 7.35 (1H, d, J=8 Hz), 7.46 (1H, dd, J=8 Hz, 1Hz), 7.67 (1H, d, J=1Hz)

(6) 1-(2-Chloro-4-methylphenyl)pyrrole

NMR (CDCl$_3$, δ): 2.48 (3H, s), 6.34 (2H, t, J=2.5 Hz), 6.89 (2H, t, J=2.5 Hz), 7.12 (1H, dd, J=9 Hz, 1Hz), 7.24 (1H, d, J=9 Hz), 7.33 (1H, br s)

Preparation 15

The following compounds were obtained according to a similar manner to that of Preparation 3.

(1)
1-(5-Methyl-2-pyridyl)pyrrole-2-carbaldehyde

NMR (CDCl$_3$, δ): 2.40 (3H, s), 6.42 (1H, dd, J=4.0 Hz, 3.5 Hz), 7.19 (1H, dd, J=4.0 Hz, 1.5 Hz), 7.33 (1H, d, J=8.5 Hz), 7.41 (1H, dd, J=3.5 Hz, 1.5 Hz), 7.64 (1H, dd, J=8.5 Hz, 2.0 Hz), 8.33 (1H, d, J=2.0 Hz), 9.75 (1H, s)

(2)
1-(3-Chloro-4-methylphenyl)pyrrole-2-carbaldehyde

NMR (CDCl$_3$, δ): 2.44 (3H, s), 6.41 (1H, dd, J=4 Hz, 3 Hz), 7.04 (1H, m), 7.15 (1H, m), 7.17 (1H, dd, J=7 Hz, 2 Hz), 7.32 (1H, d, J=7 Hz), 7.37 (1H, d, J=2 Hz), 9.48 (1H, s)

(3)
1-(3-Methoxy-4-methylphenyl)pyrrole-2-carbaldehyde

NMR (CDCl$_3$, δ): 2.27 (3H, s), 3.85 (3H, s), 6.40 (1H, dd, J=4 Hz, 3 Hz), 6.82 (1H, d, J=2 Hz), 6.87 (1H, dd, J=7 Hz, 2 Hz), 7.08 (1H, dd, J=3 Hz, 2 Hz), 7.17 (1H, dd, J=4 Hz, 2 Hz), 7.20 (1H, d, J=7 Hz), 9.59 (1H, s)

(4)
1-(2-Chloro-4-methylphenyl)pyrrole-2-carbaldehyde mp: 109°-110° C.
NMR (CDCl, δ): 2.42 (3H, s), 6.43 (1H, dd, J=4 Hz, 3 Hz), 6.95 (1H, m), 7.11 (1H, dd, J=4 Hz, 1Hz), 7.19 (1H, d, J=9 Hz), 7.15 (1H, d, J=9 Hz), 7.32 (1H, br s), 9.50 (1H, s)

Preparation 16

1-(4-Methylphenyl)pyrrole-2-carbaldehyde (1.45 g) was dissolved in chloroform (20 ml), and pyridinium hydrobromide perbromide (2.62 g) was added to the solution at 0° C. under nitrogen atmosphere. The reaction mixture was stirred at the same temperature for 30 minutes. Methylene chloride was added to the mixture, and then saturated sodium thiosulfate was added until excess reagent was decomposed. The organic solution was washed with saturated sodium hydrogencarbonate and brine, and dried over magnesium sulfate. The obtained residue was purified by isopropyl ether to give 1-bromo-1-(4-methylphenyl)pyrrole-2-carbaldehyde (1.65 g).

NMR (CDCl$_3$, δ): 2.47 (3H, s), 6.46 (1H, d, J=4 Hz), 7.09 (1H, d, J=4 Hz), 7.17 (2H, d, J=8 Hz), 7.30 (2H, d, J=8 Hz)

Preparation 17

The following compounds were obtained according to a similar manner to that of Preparation 16.

(1)
5-Bromo-1-(5-methyl-2-pyridyl)pyrrole-2-carbaldehyde mp: 65.5°-73° C.
NMR (CDCl$_3$, δ): 2.45 (3H, s), 6.47 (1H, d, J=4.5 Hz), 7.07 (1H, d, J=4.5 Hz), 7.24 (1H, d, J=7.0 Hz), 7.71 (1H, dd, J=7.0 Hz, 1.5 Hz), 8.04 (1H, d, J=1.5 Hz), 9.37 (1H, s)

(2)
5-Bromo-1-(2-chloro-4-methylphenyl)pyrrole-2-carbaldehyde

NMR (CDCl$_3$, δ): 2.44 (3H, s), 6.50 (1H, d, J=4 Hz), 7.06 (1H, d, J=4 Hz), 7.20 (2H, s), 7.36 (1H, br s), 9.29 (1H, s)

(3)
5.Bromo-1-(3-methoxy-4-methylphenyl)pyrrole-2-carbaldehyde

NMR (CDCl$_3$, δ): 2.30 (3H, s), 3.33 (3H, s), 6.47 (1H, d, J=4 Hz), 6.71 (1H, d, J=2 Hz), 6.80 (1H, dd, J=8, 2 Hz), 7.10 (1H, d, J=4 Hz), 7.24 (1H, d, J=8 Hz), 9.31 (1H, s)

Preparation 18

The following compounds were obtained according to a similar manner to that of Preparation 4.

(1)
5-Bromo-1-(4-methylphenyl)pyrrole-2-carbonitrile

NMR (CDCl$_3$, δ): 2.44 (3H, s), 6.37 (1H, d, J=4 Hz), 6.92 (1H, d, J=4 Hz), 7.23 (2H, d, J=8 Hz), 7.32 (2H, d, J=8 Hz)

(2)
1-(5-Mehyl-2pyridyl)pyrrole-2-carbonitrile

NMR (CDCl$_3$, δ): 2.39 (3H, s), 6.37 (1H, t, J=4.5 Hz), 7.04 (1H, dd, J=4.5 Hz, 1.0 Hz), 7.52 (1H, d, J=9.0 Hz), 7.56 (1H, dd, J=4.5 Hz, 1.0 Hz), 7.69 (1H, dd, J=9.0 Hz, 1.5 Hz), 8.39 (1H, d, J=1.5 Hz)

(3)
5-Bromo-1-(5-methyl-2-pyridyl)pyrrole-2-carbonitrile mp: 95°-100.5° C.
NMR (CDCl$_3$, δ): 2.45 (3H, s), 6.40 (1H, d, J=4.0 Hz), 6.95 (1H, d, J=4.0 Hz), 7.37 (1H, d, J=8.5 Hz), 7.73 (1H, dd, J=8.5 Hz, 1.5 Hz), 8.48 (1H, d, J=1.5 Hz)

(4)
5-Bromo-1-(2-chloro-4-methylphenyl)pyrrole-2-carbonitrile

NMR (CDCl$_3$, δ): 2.46 (3H, s), 6.40 (1H, d, J=4 Hz), 6.94 (1H, d, J=4 Hz), 7.20-7.94 (2H, m), 7.41 (1H, br s)

(5)

1-(3-Chloro-4-methylphenyl)pyrrole-2-carbonitrile

NMR (CDCl$_3$, δ): 2.42 (3H, s), 6.35 (1H, dd, J=4 Hz, 2.5 Hz), 6.99 (1H, dd, J=4 Hz, 1Hz), 7.05 (1H, dd, J=2.5 Hz, 1Hz), 7.28 (1H, dd, J=8 Hz, 1.5 Hz), 7.36 (1H, d, J=8 Hz), 7.45 (1H, d, J=1.5 Hz)

(6)

5-Bromo-1-(3-methoxy-4-methylphenyl)pyrrole-2-carbonitrile

NMR (CDCl$_3$, δ): 2.30 (3H, s), 3.89 (3H, s), 6.40 (1H, d, J=4 Hz), 6.78 (1H, d, J=2 Hz), 6.88 (1H, dd, J=8, 2 Hz), 6.94 (1H, d, J=4 Hz), 7.38 (1H, d, J=8 Hz)

(7)

1-(2-Chloro-4-methylphenyl)pyrrole-2-carbonitrile

NMR (CDCl$_3$, δ): 2.42 (3H, s), 6.35 (1H, dd, J=4 Hz, 3 Hz), 6.89-7.02 (2H, m), 7.18 (1H, dd, J=8 Hz, 1Hz), 7.28 (1H, d, J=8 Hz), 7.36 (1H, br s)

Preparation 19

Chlorosulfonyl isocyanate (1.2 ml) in methylene chloride (12 ml) was added dropwise to a stirred solution of 1-(2-bromo-4-methylphenyl)pyrrole (2.5 g) in methylene chloride (25 ml) kept about −20° C. under nitrogen atmosphere. The reaction mixture was stirred at −20° C. for 30 minutes and at room temperature for 1.5 hours, and then was added dropwise dimethylformamide (1.7 ml) keeping at about −20° C. The reaction mixture was stirred at −20° C. for 30 minutes and at room temperature for an hour. To the reaction mixture was added 4N-hydrochloric acid at 0° C., and stirred at 0° C. for 30 minutes. The organic layer was washed with water and saturated sodium hydrogencarbonate solution, and dried over magnesium sulfate, and evaporated in vacuo. The residue was purified by silica gel column chromatography with a mixture of ethyl acetate and n-hexane (1:10) as eluent to give 1-(2-bromo-4-methylphenyl)pyrrole-2-carbonitrile (2.4 g).

NMR (CDCl$_3$, δ): 2.42 (3H, s), 6.36 (1H, dd, J=4.0, 3.0 Hz), 6.93 (1H, dd, J=3.0 Hz, 1.0 Hz), 6.97 (1H, dd, J=4.0 Hz, 1.0 Hz), 7.22-7.29 (2H, m), 7.55 (1H, d, J=1.0 Hz)

Preparation 20

The following compounds were obtained according to a similar manner to that of Preparation 19.

(1) 1-(3-Fluoro-4-methylphenyl)pyrrole-2-carbonitrile

NMR (CDCl$_3$, δ): 2.35 (3H, d, J=2.5 Hz), 6.37 (1H, m), 6.99-7.48 (5H, m)

(2) 1-(4-Methyl-2-nitrophenyl)pyrrole-2-carbonitrile

NMR (CDCl$_3$, ε): 2.56 (3H, s), 6.48 (1H, dd, J=4 Hz, 3 Hz), 6.90 (1H, dd, J=3 Hz, 2 Hz), 7.01 (1H, dd, J=4 Hz, 2 Hz), 7.41 (1H, d, J=8 Hz), 7.57 (1H, dd, J=8 Hz, 1Hz), 7.92 (1H, d, J=1Hz)

Preparation 21

The following compounds were obtained according to a similar manner to that of Preparation 2.

(1)

4-Bromo-3-chloro-1-(4-methylphenyl)pyrrole-2-carbonitrile

NMR (CDCl$_3$, δ): 2.47 (3H, s), 6.97 (1H, s), 7.23 (2H, d, J=9 Hz), 7.35 (2H, d, J=9 Hz)

(2)

4-Bromo-1-(3-fluoro-4-methylphenyl)pyrrole-2-carbonitrile

NMR (CDCl$_3$, δ): 2.35 (3H, d, J=2.5 Hz), 6.88 (1H, d, J=2 Hz), 7.07 (1H, d, J=2 Hz), 7.09-7.49 (4H, m)

(3)

4-Bromo-1-(2-bromo-4-methylphenyl)pyrrole-2-carbonitrile

NMR (CDCl$_3$, δ): 2.41 (3H, s), 6.93 (2H, s), 7.23-7.28 (2H, m), 7.56 (1H, s)

(4)

4-Bromo-1-(2-chloro-4-methylphenyl)pyrrole-2-carbonitrile mp: 92°-94° C.

NMR (CDCl$_3$, δ): 2.42 (3H, s), 6.94 (2H, s), 7.19 (1H, dd, J=7.5 Hz, 0.8 Hz), 7.27 (1H, d, J=7.5 Hz), 7.36 (1H, m)

(5)

4-Bromo-1-(3-chloro-4-methylphenyl)pyrrole-2-carbonitrile

NMR (CDCl$_3$, δ): 2.43 (3H, s), 6.96 (1H, d, J=2 Hz), 7.06 (1H, d, J=2 Hz), 7.26 (1H, dd, J=8 Hz, 2 Hz), 7.35 (1H, d, J=8 Hz), 7.42 (1H, d, J=2 Hz)

Preparation 22

The following compounds were obtained according to a similar manner to that of Preparation 7.

(1)

4-Bromo-1-(4-bromomethylphenyl)-3-chloropyrrole-2-carbonitrile

NMR (CDCl$_3$, δ): 4.55 (2H, s), 7.00 (1H, s), 7.34 (2H, d, J=9 Hz), 7.59 (2H, d, J=9 Hz)

(2)

5-Bromo-1-(4-bromomethylphenyl)pyrrole-2-carbonitrile

NMR (CDCl$_3$, δ): 4.55 (2H, s), 6.40 (1H, d, J=4 Hz), 6.93 (1H, d, J=4 Hz), 7.33 (2H, d, J=8 Hz), 7.55 (1H, d, J=8 Hz)

(3)

4-Bromo-1-(4-bromomethyl-3-fluorophenyl)pyrrole-2-carbonitrile

NMR (CDCl$_3$, δ): 4.54 (2H, s), 7.01 (1H, d, J=2.5 Hz), 7.10 (1H, d, J=2.5 Hz), 7.19-7.62 (3H, m)

(4) 1-(5-Bromomethyl-2-pyridyl)pyrrole-2-carbonitrile

NMR (CDCl$_3$, δ): 4.52 (2H, s), 6.40 (1H, t, J=4.0 Hz), 7.08 (1H, dd, J=4.0 Hz, 1.0 Hz), 7.61 (1H, dd, J=4.0 Hz, 1.0 Hz), 7.65 (1H, d, J=9.0 Hz), 7.92 (1H, dd, J=9.0 Hz, 2.0 Hz), 8.54 (1H, d, J=2.0 Hz)

(5)

5-Bromo-1-(5-bromomethyl-2-pyridyl)pyrrole-2-carbonitrile

NMR (CDCl$_3$, δ): 4.54 (2H, s), 6.42 (1H, d, J=4.5 Hz), 6.97 (1H, d, J=4.5 Hz), 7.49 (1H, d, J=8.5 Hz), 7.98 (1H, dd, J=8.5 Hz, 1.5 Hz), 8.68 (1H, d, J=1.5 Hz)

(6)
1-(2-Bromo-4-bromomethylphenyl)pyrrole-2-carbonitrile

NMR (CDCl$_3$, δ): 4.49 (2H, s), 6.38 (1H, dd, J=4.0 Hz, 3.0 Hz), 6.93-7.03 (2H, m), 7.39 (1H, d, J=8.0 Hz), 7.49 (1H, dd, J=8.0 Hz, 1.0 Hz), 7.77 (1H, d, J=1.0 Hz)

(7)
4-Bromo-1-(2-bromo-4-bromomethylphenyl)pyrrole-2-carbonitrile

NMR (CDCl$_3$, δ): 4.48 (2H, s), 6.97 (2H, s), 7.35 (1H, d, J=8.0 Hz), 7.49 (1H, dd, J=8.0 Hz, 1.0 Hz), 7.79 (1H, d, J=1.0 Hz)

(8)
5-Bromo-1-(4-bromomethyl-2-chlorophenyl)pyrrole-2-carbonitrile

NMR (CDCl$_3$, δ): 4.50 (2H, s), 6.42 (1H, d, J=4 Hz), 6.95 (1H, d, J=4 Hz), 7.36 (1H, d, J=8 Hz), 7.47 (1H, d, J=8 Hz, 1Hz), 7.62 (1H, d, J=1Hz)

(9)
4-Bromo-1-(4-bromomethyl-2-chlorophenyl)pyrrole-2-carbonitrile (This product was a mixture of the starting material and the desired product and used to the next reaction furthermore without purification.)

(10)
4-Bromo-1-(4-bromomethyl-3-chlorophenyl)pyrrole-2-carbonitrile

NMR (CDCl$_3$, δ): 4.61 (2H, s), 6.99 (1H, d, J=1.5 Hz), 7.19 (1H, d, J=1.5 Hz), 7.36 (1H, dd, J=8 Hz and 2 Hz), 7.50 (1H, d, J=2 Hz), 7.61 (1H, d, J=8 Hz)

(11)
5-Bromo-1-(4-bromomethyl-3-methoxyphenyl)pyrrole-2-carbonitrile

NMR (CDCl$_3$, δ): 3.94 (3H, s), 4.58 (2H, s), 6.49 (1H, d, J=4 Hz), 6.85 (1H, d, J=2 Hz), 6.90-6.99 (2H, m), 7.48 (1H, d, J=8 Hz)

(12)
1-(4-Bromomethyl-2-nitrophenyl)pyrrole-2-carbonitrile

NMR (CDCl$_3$, δ): 4.57 (2H, s), 6.41 (1H, dd, J=4.3 Hz), 6.91 (1H, dd, J=3, 2 Hz), 7.03 (1H, dd, J=4 Hz, 2 Hz), 7.53 (1H, d, J=8 Hz), 7.80 (1H, dd, J=8 Hz, 2 Hz), 8.14 (1H, d, J=2 Hz)

(13)
1-(4-Bromomethyl-2-chlorophenyl)pyrrole-2-carbonitrile (This product was a mixture of the starting material and the desired product and used to the next reaction furthermore without purification.)

Preparation 23

The following compounds were obtained according to a similar manner to that of Preparation 9.

(1)
3-[4-(4-Bromo-3-chloro-2-cyano-1-pyrrolyl)benzyl]-2-butyl-7-methyl-3H-imidazo[4,5-b]pyridine NMR (CDCl$_3$, δ): 0.90 (3H, t, J=7 Hz), 1.40 (2H, m), 1.74 (2H, m), 2.71 (3H, s), 2.86 (2H, t, J=8 Hz), 5.59 (2H, s), 6.96 (1H, s), 7.07 (1H, d, J=5 Hz), 7.30 (4H, s), 8.23 (1H, d, J=5 Hz)

(2)
3-[4-(2-Bromo-5-cyano-1-pyrrolyl)benzyl]-2-butyl-7-methyl-3H-imidazo[4,5-b]pyridine NMR (CDCl$_3$, δ): 0.90 (3H, t, J=7.5 Hz), 1.41 (2H, m), 1.74 (2H, m), 2.70 (3H, s), 2.88 (2H, t, J=8 Hz), 5.60 (2H, s), 6.37 (1H, d, J=4 Hz), 6.91 (1H, d, J=4 Hz), 7.07 (1H, d, J=5 Hz), 7.31 (4H, s), 8.24 (1H, d, J=5 Hz)

(3)
3-[4-(4-Bromo-2-cyano-1-pyrrolyl)]-2-fluorobenzyl]-2-butyl-7-methyl-3H-imidazo[4,5-b]pyridine NMR (CDCl$_3$, δ): 0.92 (3H, t, J=7.5 Hz), 1.33-1.56 (2H, m), 1.68-1.87 (2H, m), 2.70 (3H, s), 2.89 (2H, t, J=7.5 Hz), 5.58 (2H, s), 6.97 (1H, d, J=1 0 Hz), 7.01-7.30 (5H, m), 8.21 (1H, d, J=5.0 Hz)

(4)
3-[4-(4-Bromo-2-cyano-1-pyrrolyl)benzyl]-7-methyl-2-propyl-3H-imidazo[4,5-b]pyridine mp: 115°-118° C.

NMR (CDCl$_3$, δ): 1.01 (3H, t, J=7.5 Hz), 1.71-1.93 (2H, m), 2.71 (3H, s), 2.85 (2H, t, J=7.5 Hz), 5.57 (2H, s), 6.96 (1H, d, J=1.5 Hz), 7.03 (1H, d, J=1.5 Hz), 7.07 (1H, d, J=5.0 Hz), 7.28 (2H, d, J=9.5 Hz), 7.38 (2H, d, J=9.5 Hz), 8.22 (1H, d, J=5.0 Hz)

(5)
2-Butyl-3-[2-(2-cyano-1-pyrrolyl)-5-pyridylmethyl]-7-methyl-3H-imidazo[4,5-b]pyridine mp: 104°-108.5° C.

NMR (CDCl$_3$, δ): 0.93 (3H, t, J=7.5 Hz), 1.34-1.55 (2H, m), 1.69-1.89 (2H, m), 2.70 (3H, s), 2.89 (2H, t, J=7.5 Hz), 5.53 (2H, s), 6.37 (1H, dd, J=4.5 Hz, 3.0 Hz), 7.01-7.11 (2H, m), 7.54 (1H, dd, J=3.0 Hz, 1.0 Hz), 7.56 (1H, d, J=8.0 Hz), 7.70 (1H, dd, J=8.0 Hz, 1.5 Hz), 8.22 (1H, d, J=5.0 Hz), 8.46 (1H, d, J=1.5 Hz)

(6)
3-[2-(5-Bromo-2-cyano-1-pyrrolyl)-5-pyridylmethyl]-2-butyl-7-methyl-3H-imidazo[4,5-b]pyridine NMR (CDCl$_3$, δ): 0.92 (3H, t, J=7.5 Hz), 3.33-1.54 (2H, m), 1.68-1.86 (2H, m), 2.70 (3H, s), 2.89 (2H, t, J=7.5 Hz), 5.60 (2H, s), 6.40 (1H, d, J=4.0 Hz), 6.95 (1H, d, J=4.0 Hz), 7.07 (1H, d, J=5.0 Hz), 7.39 (1H, d, J=8.5 Hz), 7.71 (1H, dd, J=8.5 Hz, 1.5 Hz), 8.23 (1H, d, J=5.0 Hz), 8.61 (1H, d, J=1.5 Hz)

(7)
3-[3-Bromo-4-(2-cyano-1-pyrrolyl)benzyl]-2-butyl-7-methyl-3H-imidazo[4,5-b]pyridine mp 162°-167° C.

NMR (CDCl$_3$, δ): 0.94 (3H, t, J=7.5 Hz), 1.35-1.56 (2H, m), 1.70-1.88 (2H, m), 2.71 (3H, s), 2.89 (2H, t, J=7.5 Hz), 5.53 (2H, s), 6.35 (1H, dd, J=3.5 Hz, 3.0 Hz), 6.90 (1H, dd, J=3.0 Hz, 1.0 Hz), 6.98 (1H, dd, J=3.5 Hz, 1.0 Hz), 7.08 (1H, d, J=5.0 Hz), 7.18 (1H, dd, J=8.0 Hz, 1.0 Hz), 7.35 (1H, d, J=8.0 Hz), 7.53 (1H, d, J=1.0 Hz), 8.22 (1H, d, J=5.0 Hz)

(8)
3-[3-Bromo-4-(4-bromo-2-cyano-1-pyrrolyl)benzyl]-2-butyl-7-methyl-3H-imidazo[4,5-b]pyridine NMR (CDCl$_3$, δ): 0.93 (3H, t, J=7.5 Hz), 1.34-1.55 (2H, m), 1.70-1.91 (2H, m), 2.73 (3H, s), 2.93 (2H, t, J=7.5 Hz), 5.54 (2H, s), 6.90 (1H, d, J=1.0 Hz), 6.94 (1H, d, J=1.0 Hz), 7.10 (1H, d, J=5.0 Hz), 7.18 (1H, dd, J=8.0 Hz, 1.0 Hz), 7.32 (1H, d, J=8.0 Hz), 7.56 (1H, d, J=1.0 Hz), 8.23 (1H, d, J=5.0 Hz)

(9)

3-[4-(2-Bromo-5-cyano-1-pyrrolyl)-3-chlorobenzyl]-2-butyl-7-methyl-3H-imidazo[4,5-b]pyridine NMR (CDCl$_3$, δ): 0.91 (3H, t, J=7 Hz), 1.42 (2H, m), 1.75 (2H, m), 2.73 (3H, s), 2.88 (2H, t, J=8 Hz), 5.58 (2H, s), 6.40 (1H, d, J=4 Hz), 6.92 (1H, d, J=4 Hz), 7.09 (1H, d, J=5 Hz), 7.19 (1H, dd, J=8 Hz, 1Hz), 7.31 (1H, d, J=8 Hz), 7.39 (1H, d, J=1Hz), 8.25 (1H, d, J=5 Hz)

(10)

3-[4-(4-Bromo-2-cyano-1-pyrrolyl)-3-chlorobenzyl]-2-butyl-7-methyl-3H-imidazo[4,5-b]pyridine NMR (CDCl$_3$, δ): 0.92 (3H, t, J=8 Hz), 1.45 (2H, m), 1.79 (2H, m), 2.73 (3H, s), 2.89 (2H, t, J=8 Hz), 5.55 (2H, s), 6.92 (1H, d, J=1Hz), 6.95 (1H, d, J=1Hz), 7.07 (1H, d, J=5 Hz), 7.15 (1H, dd, J=7.5 Hz, 1Hz), 7.34 (1H, d, J=7.5 Hz), 7.36 (1H, s), 8.22 (1H, d, J=5 Hz)

(11)

3-[4-(4-Bromo-2-cyano-1-pyrrolyl)-2-chlorobenzyl]-2-butyl-7-methyl-3H-imidazo[4,5-b]pyridine NMR (CDCl$_3$, δ): 0.92 (3H, t, J=8 Hz), 1.49 (2H, m), 1.78 (2H, m), 2.80 (3H, s), 3.00 (2H, m), 5.70 (2H, s), 6.77 (1H, d, J=8 Hz), 6.99 (1H, d, J=2 Hz), 7.04 (1H, d, J=2 Hz), 7.20 (1H, dd, J=8 Hz, 2 Hz), 7.25 (1H, d, J=8 Hz), 7.58 (1H, d, J=2 Hz), 8.30 (1H, d, J=8 Hz)

(12)

3-[4-(2-Bromo-5-cyano-1-pyrrolyl)benzyl]-7-methyl-2-propyl-3H-imidazo[4,5-b]pyridine NMR (CDCl$_3$, δ): 0.99 (3H, t, J=7 Hz), 1.80 (2H, m), 2.70 (3H, s), 2.84 (2H, t, J=8 Hz), 5.60 (2H, s), 6.36 (1H, d, J=4.5 Hz), 6.91 (1H, d, J=4.5 Hz), 7.05 (1H, d, J=5 Hz), 7.30 (4H, s), 8.23 (1H, d, J=5 Hz)

(13)

3-[4-(2-Bromo-5-cyano-1-pyrrolyl)-2-methoxy]benzyl]-2-butyl-7-methyl-3H-imidazo[4,5-b]pyridine NMR (CDCl$_3$, δ): 0.92 (3H, t, J=7 Hz), 1.43 (2H, m), 1.77 (2H, m), 2.73 (3H, s), 2.93 (2H, t, J=7 Hz), 3.96 (3H, s), 5.56 (2H, s), 6.37 (1H, d, J=4 Hz), 6.71-6.89 (3H, m), 6.92 (1H, d, J=4 Hz), 7.07 (1H, d, J=5 Hz), 8.23 (1H, d, J=5 Hz)

(14)

2-Butyl-3-[4-(2-cyano-1-pyrrolyl)-3-nitrobenzyl]-7-methyl-3H-imidazo[4,5-b]pyridine NMR (CDCl$_3$, δ): 0.96 (3H, t, J=7 Hz), 1.48 (3H, m), 1.83 (2H, m), 2.98 (2H, t, J=7 Hz), 5.64 (2H, s), 6.39 (1H, dd, J=4 Hz, 3 Hz), 6.88 (1H, dd, J=3 Hz, 2 Hz), 7.01 (1H, dd, J=4 Hz, 2 Hz), 7.12 (1H, d, J=4 Hz), 7.44-7.56 (2H, m), 7.98 (1H, s), 8.25 (1H, d, J=4 Hz)

(15)

2-Butyl-3-[3-chloro-4-(2-cyano-1-pyrrolyl)benzyl]-7-methyl-3H-imidazo[4,5-b]pyridine NMR (CDCl$_3$, δ): 0.95 (3H, t, J=7 Hz), 1.46 (2H, m), 1.80 (2H, m), 2.73 (3H, s), 2.90 (2H, t, J=7.5 Hz), 5.56 (2H, s), 6.36 (1H, dd, J=4 Hz, 3 Hz), 6.93 (1H, dd, J=3 Hz, 1Hz), 6.99 (1H, dd, J=4 Hz, 1Hz), 7.08 (1H, d, J=5 Hz), 7.15 (1H, dd, J=8 Hz, 1Hz), 7.34 (1H, d, J=8 Hz), 7.35 (1H, d, J=1Hz), 8.23 (1H, d, J=5 Hz)

Preparation 24

To a stirred mixture of 1-(4-methylphenyl)pyrrole-2-carbonitrile (10 g), silica gel (46 g) and carbon tetrachloride (150 ml) was added dropwise a solution of tertbutyl hypochlorite (8.1 g) in carbon tetrachloride (15 ml). After stirring for 1 hour at ambient temperature, the precipitate was filtered off and the filtrate was evaporated in vacuo to give an oily residue which was crystalized from n-hexane. The crystals were further purified by silica gel column chromatography (SiO$_2$ 100 g, n-hexane-toluene=1:1) and subsequent crystallization from n-hexane to give colorless crystals (3.92 g) of 4-chloro-1-(4-methylphenyl)pyrrole-2-carbonitrile.

mp: 72°-74° C.

NMR (CDCl$_3$, δ): 2.43 (3H, s), 6.89 (1H, d, J=2 Hz), 7.02 (1H, d, J=2 Hz), 7.33 (4H, s)

Preparation 25

The following compound was obtained according to a similar manner to that of Preparation 7.

1-(4-Bromomethylphenyl)-4-chloropyrrole-2-carbonitrile mp: 95°-97° C.

NMR (CDCl$_3$, δ): 4.52 (2H, s), 6.92 (1H, d, J=1Hz), 7.03 (1H, d, J=1Hz), 7.41 (2H, d, J=8 Hz), 7.54 (2H, d, J=8 Hz)

Preparation 26

The following compound was obtained according to a similar manner to that of Preparation 9.

2-Butyl-3-[4-(4-chloro-2-cyano-1-pyrrolyl)benzyl]-7-methyl-3H-imidazo[4,5-b]pyridine mp: 112°-113° C.

NMR (CDCl$_3$, δ): 0.92 (3H, t, J=7.5 Hz), 1.32-1.53 (2H, m), 1.66-1.87 (2H, m), 2.72 (3H, s), 2.90 (2H, t, J=7.5 Hz), 5.57 (2H, s), 6.89 (1H, d, J=1.5 Hz), 6.99 (1H, d, J=1.5 Hz), 7.09 (1H, d, J=5.0 Hz), 7.28 (2H, d, J=9.0 Hz), 7.39 (2H, d, J=9.0 Hz), 8.24 (1H, d, J=5.0 Hz)

Preparation 27

To a suspension of sodium hydride (114 mg, 60% oil dispersion) in dimethyl sulfoxide (5 ml) was added dropwise a solution of 2-butyrylamino-4-methyl-3-nitropyridine (605 mg) in dimethyl sulfoxide (10 ml) at ambient temperature under nitrogen atmosphere. The mixture was stirred at the same temperature for one hour and a solution of 1-(4-bromomethylphenyl)-4-chloropyrrole-2-carbonitrile (800 ml) in dimethyl sulfoxide (10 ml) was added therein. The reaction mixture was stirred at ambient temperature for 2 hours and quenched with ice water. The separated oil was extracted twice with ethyl acetate. The combined extracts were washed with water, dried, and concentrated in vacuo. The residue was purified by column chromatography on silica gel eluted by n-hexane/ethylacetate (2/1-1/1) to yield 2-[N-butyryl-N-[4-(4-chloro-2-cyano-1-pyrrolyl)benzyl]amino]-4-methyl-3-nitropyridine (723 mg).

mp: 139°-141° C.

NMR (CDCl$_3$, δ): 0.90 (3H, t, J=7.5 Hz), 1.57-1.80 (2H, m), 1.98-2.20 (2H, broad peak), 2.42 (3H, s), 4.40-5.35 (2H, broad peak), 6.91 (1H, d, J=1Hz), 7.04 (1H, d, J=1Hz), 7.10-7.65 (5H, m), 8.40-8.58 (1H, m)

Preparation 28

A mixture of 2-[N-butyryl-N-[4-(4-chloro-2-cyano-1-pyrrolyl)benzyl]amino]-4-methyl-3-nitropyridine (700 mg), iron powder (894 mg), acetic acid (1.8 ml) and ethanol (15 ml) was stirred under reflux for 15 hours. After being cooled to room temperature, the reaction mixture was filtered and the filtrate was evaporated in vacuo. The residue was partitioned into ethyl acetate (100 ml) and saturated aqueous sodium hydrogencarbonate solution. The organic layer was washed with water, dried over magnesium sulfate and evaporated in vacuo. The residue was purified by a silica gel column chromatography (n-hexane-ethyl acetate =1:1) to give 3-[4-(4-chloro-2-cyano-1-pyrrolyl)benzyl]-7-methyl-2-propyl-3H-imidazo[4,5-b]pyridine (565 mg) as a pale yellow powder.

NMR (CDCl$_3$, $\delta$): 1.01 (3H, t, J=7.5 Hz), 1.70–1.94 (2H, m), 2.71 (3H, s), 2.33 (2H, t, J=7.5 Hz), 5.56 (2H, s), 6.89 (1H, d, J=1Hz), 7.00 (1H, d, J=1Hz), 7.07 (1H, d, J=5 Hz), 7.25 (2H, d, J=8 Hz), 7.38 (2H, d, J=8 Hz), 8.22 (1H, d, J=5 Hz)

Preparation 29

The following compounds were obtained according to a similar manner to that of Preparation 13.

(1) 1-(2-Fluoro-4-methylphenyl)pyrrole

NMR (CDCl$_3$, $\delta$): 2.38 (3H, s), 6.33 (2H, t, J=2.5 Hz), 6.96–7.08 (4H, m), 7.28 (1H, t, J=8.0 Hz)

(2) 1-(3-Fluoro-4-methylphenyl)pyrrole mp: 64°–67.5° C.

NMR (CDCl$_3$, $\delta$): 2.28 (3H, d, J=1.0 Hz), 6.32 (2H, t, J=2.5 Hz), 7.04 (2H, t, J=2.5 Hz), 7.01–7.12 (2H, m), 7.21 (1H, t, J=8.0 Hz)

(3) Ethyl 3-methyl-4-(1-pyrrolyl)benzoate

NMR (CDCl$_3$, $\delta$): 1.40 (3H, t, J=7.5 Hz), 2.30 (3H, s), 4.40 (2H, q, J=7.5 Hz), 6.30–6.38 (2H, m), 6.77–6.85 (2H, m), 7.30 (1H, d, J=8 Hz), 7.93 (1H, dd), 8.00 (1H, d)

Preparation 30

The following compounds were obtained according to a similar manner to that of Preparation 3.

(1) 1-(3-Fluoro-4-methylphenyl)pyrrole-2-carbaldehyde

NMR (CDCl$_3$, $\delta$): 2.32 (3H, d, J=1.0 Hz), 6.40 (1H, dd, J=4.5 Hz, 3.0 Hz), 6.99–7.11 (3H, m), 7.15 (1H, dd, J=4.5 Hz, 1.0 Hz), 7.26 (1H, t, J=8.0 Hz), 9.57 (1H, s)

(2) 1-(2-Bromo-4-methylphenyl)pyrrole-2-carbaldehyde mp: 116°–119° C.

NMR (CDCl$_3$, $\delta$): 2.42 (3H, s), 6.42 (1H, dd, J=4.0 Hz, 3.0 Hz), 6.91–6.97 (1H, m), 7.12 (1H, dd, J=4.0 Hz, 1.0 Hz), 7.19–7.24 (2H, m), 7.52 (1H, s), 9.49 (1H, s)

Preparation 31

The following compounds were obtained according to a similar manner to that of Preparation 16.

(1) 5-Bromo-1-(3-fluoro-4-methylphenyl)pyrrole-2-carbaldehyde mp: 126°–138.5° C.

NMR (CDCl$_3$, $\delta$): 2.38 (3H, d, J=1.5 Hz), 6.47 (1H, d, J=4.5 Hz), 6.97 (2H, d, J=8.0 Hz), 7.08 (1H, d, J=4.5 Hz), 7.31 (1H, t, J=8.0 Hz), 9.32 (1H, s)

(2) 5-Bromo-1-(2-bromo-4-methylphenyl)pyrrole-2-carbaldehyde mp: 110.5°–113.5° C.

NMR (CDCl$_3$, $\delta$): 2.44 (3H, s), 6.51 (1H, d, J=4.5 Hz), 7.08 (1H, d, J=4.5 Hz), 7.20–7.30 (2H, m), 7.54 (1H, d, J=0.5 Hz), 9.29 (1H, s)

Preparation 32

The following compounds were obtained according to a similar manner to that of Preparation 19.

(1) 1-(4-Ethoxycarbonyl-2-methylphenyl)pyrrole-2-carbonitrile

NMR (CDCl$_3$, $\delta$): 1.44 (3H, t, J=7.5 Hz), 2.20 (3H, s), 4.42 (2H, q, J=7.5 Hz), 6.35–6.43 (1H, m), 6.88–6.98 (1H, m), 6.98–7.04 (1H, m), 7.38 (1H, d, J=9 Hz), 8.00 (1H, dd, J=9 Hz, 1Hz), 8.07 (1H, d, J=1Hz)

(2) 1-(2-Fluoro-4-methylphenyl)pyrrole-2-carbonitrile mp: 47°–52° C.

NMR (CDCl$_3$, $\epsilon$): 2.41 (3H, s), 6.35 (1H, dd, J=4.5 Hz, 3.5 Hz), 6.94–7.15 (4H, m), 7.31 (1H, t, J=8.0 Hz)

(3) 1-(4-Ethoxycarbonylphenyl)pyrrole-2-carbonitrile mp: 110°–112° C.

NMR (CDCl$_3$, $\delta$): 1.43 (3H, t, J=7.5 Hz), 4.43 (2H, q, J=7.5 Hz), 6.40 (1H, q, J=4 Hz & 3 Hz), 7.05 (1H, q, J=4 Hz & 2 Hz), 7.16 (1H, q, J=3 Hz & 2 Hz), 7.57 (2H, d, J=10 Hz), 8.21 (2H, d, J=10 Hz)

Preparation 33

The following compounds were obtained according to a similar manner to that of Preparation 4.

(1) 5-Bromo-1-(3-fluoro-4-methylphenyl)pyrrole-2-carbonitrile mp: 56.5°–58° C.

NMR (CDCl$_3$, $\delta$): 2.37 (3H, d, J=1.0 Hz), 6.38 (1H, d, J=4.5 Hz), 6.92 (1H, d, J=4.5 Hz), 7.02–7.11 (2H, m), 7.35 (1H, t, J=8.0 Hz)

(2) 5-Bromo-1-(2-bromo-4-methylphenyl)pyrrole-2-carbonitrile

NMR (CDCl$_3$, $\delta$): 2.45 (3H, s), 6.39 (1H, d, J=4.5 Hz), 6.95 (1H, d, J=4.5 Hz), 7.27 (2H, s), 7.59 (1H, s)

Preparation 34

The following compound was obtained according to a similar manner to that of Preparation 2.

4-Bromo-1-(5-methyl-2-pyridyl)pyrrole-2-carbonitrile mp: 97.5°–109.5° C.

NMR (CDCl$_3$, $\delta$): 2.41 (3H, s), 7.01 (1H, d, J=1.5 Hz), 7.50 (1H, d, J=8.0 Hz), 7.57 (1H, d, J=1.5 Hz), 7.70 (1H, dd, J=8.0 Hz, 1.0 Hz), 8.38 (1H, d, J=1.0 Hz)

Preparation 35

To a mixture of 1-(4-ethoxycarbonylphenyl)pyrrole-2-carbonitrile (5.16 g) and aluminum chloride (5.72 g) in 1,2-dichloroethane (51 ml) was added a solution of dichloromethylmethyl ether (2.97 g) in 1,2-dichloroethane (5 ml) in one portion at -15° C. The mixture was stirred for one hour at the same temperature and then dichloromethylmethyl ether (0.6 g) was added therein. After stirring for 3 hours at 5° C., the reaction mixture was quenched with 10% hydrochloric acid. The separated organic layer was washed with 10% hydrochloric acid three times, dried, and concentrated in vacuo. The residue was purified by flash column chromatography on silica gel eluted by 1% methanol in dichloromethane to yield 1-(4-ethoxycarbonylphenyl)-4-formylpyrrole-2-carbonitrile (2.96 g) as a pale yellow solid.

mp: 28°-129.5° C.

NMR (CDCl$_3$, δ): 1.46 (3H, t, J=7.5 Hz), 4.44 (2H, q, J=7.5 Hz), 7.48 (1H, d, J=2 Hz), 7.59 (2H, d, J=10 Hz), 7.73 (1H, d, J=2 Hz), 8.27 (2H, t, J=10 Hz), 9.89 (1H, s)

Preparation 36

To a solution of dimethylsulfoxide (64 ml) was added sodium hydride (480 mg, 60% oil dispersion) at ambient temperature. The suspension was stirred at 60° C. for 50 minutes to give a clear solution. To the cooled solution was added methyltriphenylphosphonium bromide (4.29 g) at ambient temperature in one portion. The mixture was stirred at ambient temperature for half an hour and at 50° C. for half an hour. The yellow mixture was cooled to ambient temperature and therein 1-(4-ethoxycarbonylphenyl)-4-formylpyrrole-2-carbonitrile (2.68 g) was added in one portion. After stirring at ambient temperature for one and half hours, the mixture was quenched with aqueous hydrochloric acid and extracted with dichloromethane. The organic layer was washed with aqueous hydrochloric acid three times, dried, and concentrated in vacuo. The residue was purified by flash column chromatography on silica gel eluted by 20% n-hexane in dichloromethane to yield 1-(4-ethoxycarbonylphenyl)-4-vinylpyrrole-2-carbonitrile (1.80 g) as a white solid.

mp: 118.5°-120° C.

NMR (CDCl$_3$, δ): 1.43 (3H, t, J=7.5 Hz), 4.42 (2H, q, J=7.5 Hz), 5.18 (1H, d, J=10 Hz), 5.56 (1H, d, J=17.5 Hz), 6.56 (1H, q, J=10 Hz & 17.5 Hz), 7.14 (2H, s), 7.56 (2H, d, J=7.5 Hz), 8.21 (2H, d, J=7.5 Hz)

Preparation 37

A mixture of 1-(4-ethoxycarbonylphenyl)-4-vinylpyrrole-2-carbonitrile (1.59 g) and lithium borohydride (78.4 mg) in tetrahydrofuran (30 ml) was refluxed for 3 hours. To the pale green solution was added lithium borohydride (78.4 mg) and the mixture was refluxed for 3 hours. The cooled mixture was quenched with saturated aqueous ammonium chloride solution and diethyl ether was added. The separated organic layer was washed with saturated aqueous ammonium chloride solution, dried, and concentrated in vacuo. The residue was purified by flash column chromatography on silica gel eluted by 2% methanol in dichloromethane to yield 1-(4-hydroxymethylphenyl)-4-vinylpyrrole-2-carbonitrile (910 mg) as a white solid.

mp: 77°-79° C.

NMR (CDCl$_3$, δ): 4.79 (2H, s), 5.16 (1H, d, J=10 Hz), 5.54 (1H, d, J=17.5 Hz), 6.55 (1H, q, J=10 Hz & 17.5 Hz), 7.10 (2H, s), 7.43 (2H, d, J=10 Hz), 7.52 (2H, d, J=10 Hz)

Preparation 38

The following compound was obtained according to a similar manner to that of Preparation 37.

1-(4-Hydroxymethyl-2-methylphenyl)pyrrole-2-carbonitrile

NMR (CDCl$_3$, δ): 1.82 (1H, br), 2.14 (3H, s), 4.74 (2H, s), 6.30-6.40 (1H, m), 6.85-6.93 (1H, m), 6 93-7.00 (1H, m), 7.22-7.40 (3H, m)

Preparation 39

To a mixture of 1-(4-methylphenyl)pyrrole-2-carbonitrile (546 mg) and aluminum chloride (532 mg) in dichloromethane (10 ml) was added t-butyl chloride (368 mg) in dichloromethane (10 ml) in one portion at 5° C. The mixture was stirred at the same temperature for 20 minutes. The reaction mixture was quenched with 10% hydrochloric acid. The separated organic layer was washed with 10% hydrochloric acid and water, successively, dried, and concentrated in vacuo. The residue was purified by flash column chromatography on silica gel eluted by a mixture of ethyl acetate and n-hexane (1:6) to yield 4-t-butyl-1-(4-methylphenyl)pyrrole-2-carbonitrile (660 mg).

mp: 77°-78° C.

NMR (CDCl$_3$, δ): 1.28 (9H, s), 2.40 (3H, s), 6.87 (1H, d, J=2 Hz), 6.90 (1H, d, J=2 Hz), 7.27 (2H, d, J=10 Hz), 7.32 (2H, d, J=10 Hz)

Preparation 40

The following compounds were obtained according to a similar manner to that of Preparation 7.

(1)

1-(4-Bromomethyl-2-fluorophenyl)pyrrole-2-carbonitrile mp: 67°-69° C.

NMR (CDCl$_3$, δ): 4.50 (2H, s), 6.40 (1H, dd, J=4.5 Hz, 3.5 Hz), 6.99-7.10 (2H, m), 7.28-7.51 (3H, m)

(2)

5-Bromo-1-(4-bromomethyl-3-fluorophenyl)pyrrole-2-carbonitrile mp: 70.5°-73° C.

NMR (CDCl$_3$, δ): 4.57 (2H, s), 6.41 (1H, d, J=4.5 Hz), 6.95 (1H, d, J=4.5 Hz), 7.15 (1H, dd, J=8.0 Hz, 1.0 Hz), 7.19 (1H, dd, J=8.0 Hz, 1.0 Hz), 7.59 (1H, t, J=8.0 Hz)

(3)

4-Bromo-1-(5-bromomethyl-2-pyridyl)pyrrole-2-carbonitrile mp: 107.5°-115° C.

NMR (CDCl$_3$, δ): 4.51 (2H, s), 7.03 (1H, d, J=1.0 Hz), 7.62 (1H, d, J=8.5 Hz), 7.63 (1H, d, J=1.0 Hz), 7.93 (1H, dd, J=8.5 Hz, 1.5 Hz), 8.53 (1H, d, J=1.5 Hz)

(4)

5-Bromo-1-(2-bromo-4-bromomethylphenyl)pyrrole-2-carbonitrile

NMR (CDCl$_3$, δ): 4.49 (2H, s), 6.42 (1H, d, J=4.0 Hz), 6.96 (1H, d, J=4.0 Hz), 7.37 (1H, d, J=8.0 Hz), 7.53 (1H, dd, J=8.0 Hz, 1.5 Hz), 7.80 (1H, d, J=1.5 Hz)

(5) 1-(4-Bromomethylphenyl)pyrrole-2,5-dicarbonitrile mp: 123°-138° C.

NMR (CDCl$_3$, δ): 4.53 (2H, s), 6.99 (2H, s), 7.46 (2H, d, J=8 Hz), 7.62 (2H, d, J=8 Hz)

(6)
1-(4-Bromomethylphenyl)-4-tert-butylpyrrole-2-carbonitrile mp: 108°-109° C.

NMR (CDCl₃, δ): 1.25 (9H, s), 4.52 (2H, s), 6.88 (1H, d, J=1Hz), 6.91 (1H, d, J=1Hz), 7.36-7.56 (4H, m)

Preparation 41

To a solution of 1-(4-hydroxymethylphenyl)-4-vinylpyrrole-2-carbonitrile (910 mg) in dichloromethane (15 ml) was added pyridine (385 mg), 4-dimethylaminopyridine (20 mg), methanesulfonyl chloride (560 mg) successively at 5° C. The mixture was stirred at ambient temperature for 4 hours and then pyridine (385 mg) and methanesulfonyl chloride (560 mg) was added therein. The mixture was stirred at the same temperature overnight, washed with aqueous hydrochloric acid, dried, and concentrated in vacuo. The residue was purified by flash column chromatography on silica gel eluted by dichloromethane to yield 1-(4-chloromethylphenyl)-4-vinylpyrrole-2-carbonitrile (831 mg) as a colorless oil.

NMR (CDCl₃, δ): 4.64 (2H, s), 5.17 (1H, dd, J=1Hz & 10 Hz), 5.54 (1H, dd, J=1Hz & 17.5 Hz), 6.56 (1H, dd, J=10 Hz & 17.5 Hz), 7.10 (1H, d, J=1.5 Hz), 7.08 (1H, d, J=1.5 Hz), 7.44 (2H, d, J=7.5 Hz), 7.54 (2H, d, J=7.5 Hz)

Preparation 42

The following compound was obtained according to a similar manner to that of Preparation 41.

1-(4-Chloromethyl-2-methylphenyl)pyrrole-2-carbonitrile

NMR (CDCl₃, δ): 2.15 (3H, s), 4.60 (2H, s), 6.32-6.40 (1H, m), 6.85-6.93 (1H, m), 6.93-7.01 (1H, m), 7.23-7.44 (3H, m)

Preparation 43

A mixture of ethyl 4-amino-3-nitrobenzoate (49.5 g) and N,N-dimethylaniline (90 ml) was heated at 110° C. under nitrogen atmosphere. To the solution was added valeryl chloride (29 ml) and the mixture was stirred at 110° C. for 1.5 hours. After being cooled to room temperature, 1N hydrochloric acid was added until pH 2~3 to the reaction mixture. The aqueous solution was extracted with ethyl acetate. The organic layer was separated and washed successively with water and brine. The solution was dried over magnesium sulfate and the solvent was evaporated in vacuo. The residue was purified with silica gel column chromatography (ethyl acetate: n-hexane =1:5) to give ethyl 3-nitro-4-valerylaminobenzoate (67.5 g).

NMR (CDCl₃, δ): 0.98 (3H, t, J=7.5 Hz), 1.35-1.56 (2H, m), 1.43 (3H, t, J=7.5 Hz), 1.67-1.85 (2H, m), 2.52 (2H, t, J=7.5 Hz), 4.43 (2H, q, J=7.5 Hz), 7.82 (1H, dd, J=9.0 Hz, 1.0 Hz), 8.28 (1H, d, J=9.0 Hz), 9.41 (1H, d, J=1.0 Hz)

Preparation 44

The following compounds were obtained according to a similar manner to that of Preparation 43.

(1)
6-Chloro-3-nitro-2-valerylaminopyridine mp: 101°-102° C.

NMR (CDCl₃, δ): 0.96 (3H, t, J=7.5 Hz), 1.47 (2H, m), 1.72 (2H, m), 2.72 (2H, t, J=7.5 Hz), 7.18 (1H, d, J=9 Hz), 8.43 (1H, d, J=9 Hz)

(2)
6-Methoxy-3-Nitro-2-valerylaminopyridine mp: 62°-64° C.

NMR (CDCl₃, δ): 0.97 (3H, t, J=7.5 Hz), 1.43 (2H, m), 1.76 (2H, m), 2.79 (2H, t, J=7.5 Hz), 4.06 (3H, s), 6.51 (1H, d, J=9 Hz), 8.42 (1H, d, J=9 Hz)

Preparation 45

The following compounds were obtained according to a similar manner to that of Preparation 27.

(1)
4-Bromo-1-[4-[N-(5-ethoxycarbonyl-2-nitrophenyl)-N-valerylamino]methylphenyl]pyrrole-2-carbonitrile NMR (CDCl₃, δ): 0.87 (3H, t, J=7.5 Hz), 1.15-1.50 (5H, m), 1.54-1.80 (2H, m), 1.99-2.18 (2H, m), 4.43 (2H, q, J=7.5 Hz), 4.63 (1H, d, J=15 Hz), 5.20 (1H, d, J=15 Hz), 7.00 (1H, d, J=1Hz), 7.10 (1H, d, J=1Hz), 7.30-7.40 (4H, m), 7.73 (1H, d, J=1Hz), 7.98 (1H, d, J=10 Hz), 8.21 (1H, dd, J=10 Hz, 1Hz)

(2)
4-Bromo-1-[4-[N-(6-chloro-3-nitropyridin-2-yl)-N-valerylamino]methylphenyl}pyrrole-2-carbonitrile NMR (CDCl₃, δ): 0.87 (3H, t, J=7.5 Hz), 1.18-1.40 (2H, m), 1.52-1.76 (2H, m), 2.28-2.55 (2H, m), 5.20-5.45 (2H, br), 6.98 (1H, d, J=1Hz), 7.08 (1H, d, J=1Hz), 7.30-7.72 (5H, m), 8.23 (1H, d, J=8 Hz)

(3)
4-Bromo-1-[4-[N-(6-methoxy-3-nitropyridin-2-yl)-N-valerylamino]methylphenyl]pyrrole-2-carbonitrile NMR (CDCl₃, δ): 0.85 (3H, t, J=7.5 Hz), 1.18-1.41 (2H, m), 1.50-1.75 (4H, m), 2.05-2.48 (1H, br s), 5.10-5.45 (1H, br s), 6.65-6.86 (1H, m), 6.95 (1H, d, J=1Hz), 7.06 (1H, d, J=1Hz), 7.20-7.60 (4H, m), 8.20-8.35 (1H, m)

Preparation 46

To a solution of 3,4-diaminothiophene (156 mg) in ethanol (10 ml) was added trimethyl orthovalerate (0.29 ml) and pyridinium p-toluenesulfonate (4 mg). The mixture was refluxed for one hour and concentrated in vacuo. The residue was purified by preparative thin layer chromatography on silica gel developed by ethyl acetate to give 2-butyl-1H-thieno[3,4-d]imidazole (155 mg) as crystals.

mp: 112°-114° C.

NMR (CDCl₃, δ): 0.92 (3H, t, J=7 Hz), 1.32-1.5 (2H, m), 1.7-1.9 (2H, m), 2.79 (2H, t, J=7 Hz), 6.0-6.6 (1H, br s), 6.73 (2H, s)

Preparation 47

The following compounds were obtained according to a similar manner to that of Preparation 9.

(1)
2-Butyl-3-[4-(2-cyano-1-pyrrolyl)-3-fluorobenzyl]-7-methyl- 3H-imidazo[4,5-b]pyridine mp: 119°-122° C.

NMR (CDCl₃, δ): 0.92 (3H, t, J=7.5 Hz), 1.34-1.56 (2H, m), 1.70-1.89 (2H, m), 2.72 (3H, s), 2.89 (2H, t, J=7.5 Hz), 5.54 (2H, s), 6.37 (1H, dd, J=4.5 Hz, 3.5 Hz), 6.95-7.14 (5H, m), 7.40 (1H, t, J=6.5 Hz), 8.23 (1H, d, J=5 Hz)

(2)
2-Butyl-3-[4-(5-bromo-2-cyano-1-pyrrolyl)-2-fluorobenzyl]-7-methyl-3H-imidazo[4,5-b]pyridine NMR (CDCl$_3$, δ): 0.93 (3H, t, J=7.5 Hz), 1.33-1.56 (2H, m), 1.69-1.87 (2H, m), 2.72 (3H, s), 2.93 (2H, t, J=7.5 Hz), 5.62 (2H, s), 6.39 (1H, d, J=4.5 Hz), 6.93 (1H, d, J=4.5 Hz), 7.01-7.17 (3H, m), 7.20 (1H, dd, J=10.0 Hz, 1.5 Hz), 8.26 (1H, d, J=5.0 Hz)

(3)
3-[[2-(4-Bromo-2-cyano-1-pyrrolyl)pyridin-5-yl]methyl]-2-butyl-7-methyl-3H-imidazo[4,5-b]pyridine mp: 135°-138.5° C.

NMR (CDCl$_3$, δ) 0.94 (3H, t, J=7.5 Hz), 1.33-1.55 (2H, m), 1.69-1.88 (2H, m), 2.70 (3H, s), 2.89 (2H, t, J=7.5 Hz), 5.53 (2H, s), 7.01 (1H, d, J=1.5 Hz), 7.08 (1H, d, J=5.0 Hz), 7.54 (1H, d, J=8.0 Hz), 7.56 (1H, d, J=1.5 Hz), 7.70 (1H, dd, J=8.0 Hz, 2.0 Hz), 8.22 (1H, d, J=5.0 Hz), 8.46 (1H, d, J=2.0 Hz)

(4)
3-[3-Bromo-4-(5-bromo-2-cyano-1-pyrrolyl)benzyl]-2-butyl-7-methyl-3H-imidazo[4,5-b]pyridine mp: 139°-145.5° C.

NMR (CDCl$_3$, δ): 0.92 (3H, t, J=7.5 Hz), 1.31-1.54 (2H, m), 1.67-1.85 (2H, m), 2.71 (3H, s), 2.89 (2H, t, J=7.5 Hz), 5.56 (2H, s), 6.39 (1H, d, J=4.0 Hz), 6.93 (1H, d, J=4.0 Hz), 7.09 (1H, d, J=5.0 Hz), 7.21 (1H, dd, J=7.5 Hz, 1.5 Hz), 7.31 (1H, d, J=7.5 Hz), 7.57 (1H, d, J=1.5 Hz), 8.23 (1H, d, J=5.0 Hz)

(5)
2-Butyl-3-[4-(2,5-dicyano-1-pyrrolyl)benzyl]-7-methyl-3H-imidazo[4,5-b]pyridine mp: 159°-161° C.

NMR (CDCl$_3$, δ): 0.90 (3H, t, J=7.5 Hz), 1.28-1.52 (2H, m), 1.63-1.86 (2H, m), 2.70 (3H, s), 2.86 (2H, t, J=7.5 Hz), 5.59 (2H, s), 6.96 (2H, s), 7.08 (1H, d, J=5 Hz), 7.33 (2H, d, J=8 Hz), 7.41 (2H, d, J=8 Hz), 8.21 (1H, d, J=5 Hz)

(6)
3-[4-(2-Cyano-1-pyrrolyl)-3-methylbenzyl]-7-methyl-3-propyl-3H-imidazo[4,5-b]pyridine mp: 127°-128° C.

NMR (CDCl$_3$, δ): 1.03 (3H, t, J=7.5 Hz), 1.72-1.94 (2H, m), 2.08 (3H, s), 2.72 (3H, s), 2.85 (3H, t, J=7.5 Hz), 5.52 (2H, s), 6.28-6.38 (1H, m), 6.80-6.88 (1H, m), 6.91-6.99 (1H, m), 6.99-7.14 (3H, m), 7.20 (1H, d, J=8 Hz), 8.21 (1H, d, J=5 Hz)

(7)
3-[4-(4-Bromo-2-cyano-1-pyrrolyl)benzyl]-2-butyl-3H-imidazo[4,5-d]pyrimidine mp: 120°-125° C.

NMR (CDCl$_3$, δ): 0.94 (3H, t, J=7.5 Hz), 1.32-1.55 (2H, m), 1.75-1.95 (2H, m), 2.92 (2H, t, J=7.5 Hz), 5.58 (2H, s), 6.99 (1H, d, J=1Hz), 7.08 (1H, d, J=1Hz), 7.34 (2H, d, J=8 Hz), 7.44 (2H, d, J=8 Hz), 9.02 (1H, s), 9.12 (1H, s)

(8)
2-Butyl-3-[4-(4-tert-butyl-2-cyano-1-pyrrolyl)benzyl]-7-methyl-3H-imidazo[4,5-b]pyridine NMR (CDCl$_3$, δ): 0.91 (3H, t, J=7.5 Hz), 1.26 (9H, s), 1.30-1.55 (2H, m), 1.65-1.90 (2H, m), 2.73 (3H, s), 2.88 (2H, t), 5.54 (2H, s), 6.80 (1H, d, J=1Hz), 6.88 (1H, d, J=1Hz), 7.08 (1H, d, J=5 Hz), 7.23 (2H, d, J=8 Hz), 7.39 (2H, d, J=8 Hz), 8.23 (1H, d, J=5 Hz)

(9)
2-Butyl-3-[4-(4-chloro-2-cyano-1-pyrrolyl)benzyl]-3H-imidazo[4,5-b]pyridine NMR (CDCl$_3$, δ): 0.93 (3H, t, J=7.5 Hz), 1.30-1.53 (2H, m), 1.73-1.93 (2H, m), 2.82 (2H, t, J=7.5 Hz), 5.57 (2H, s), 6.89 (1H, d, J=2 Hz), 7.00 (1H, d, J=2 Hz), 7.19-7.46 (5H, m), 8.02 (1H, dd, J=8 Hz, 1Hz), 8.36 (1H, dd, J=5 Hz, 1Hz)

(10)
3-[4-(2-Cyano-4-vinyl-1-pyrrolyl)benzyl]-7-methyl-2-propyl-3H-imidazo[4,5-b]pyridine NMR (CDCl$_3$, δ): 1.01 (3H, t, J=7.5 Hz), 1.70-1.92 (2H, m), 2.70 (3H, s), 2.83 (2H, t, J=7.5 Hz), 5.14 (1H, dd, J=11Hz, 1Hz), 5.43-5.60 (3H, m), 6.52 (1H, dd, J=11Hz, 17.5 Hz), 7.00-7.10 (3H, m), 7.25 (2H, d, J=8 Hz), 7.39 (2H, d, J=8 Hz), 8.21 (1H, d, J=5 Hz)

(11)
1-[4-(4-Bromo-2-cyano-1-pyrrolyl)benzyl]-2-butylthieno[3,4-d]imidazole

NMR (CDCl$_3$, δ): 0.88 (3H, t, J=7 Hz), 1.39 (2H, m), 1.78 (2H, m), 2.71 (2H, t, J=7 Hz), 5.15 (2H, s), 6.24 (1H, d, J=2 Hz), 6.90 (1H, d, J=2 Hz), 6.97 (1H, d, J=2 Hz), 7.00 (1H, d, J=2 Hz), 7.22 (2H, d, J=9 Hz), 7.36 (2H, d, J=9 Hz)

(12)
1-[4-(4-Bromo-2-cyano-1-pyrrolyl)benzyl]-2-butyl-4-chloro-5-hydroxymethylimidazole mp: 154°-155° C.

NMR (CDCl$_3$, δ): 0.90 (3H, t, J=7 Hz), 1.36 (2H, m), 1.69 (2H, m), 2.60 (2H, t, J=7 Hz), 4.52 (2H, s), 5.30 (2H, s), 6.98 (1H, d, J=2 Hz), 7.08 (1H, d, J=2 Hz), 7.16 (2H, d, J=9 Hz), 7.42 (2H, d, J=9 Hz)

Preparation 48

The following compounds were obtained according to a similar manner to that of Preparation 28.

(1)
1-[4-(4-Bromo-2-cyano-1-pyrrolyl)benzyl]-2-butyl-6-ethoxycarbonyl-1H-benzimidazole mp: 130°-132° C.

NMR (CDCl$_3$, δ): 0.94 (3H, t, J=7.5 Hz), 1.32-1.60 (5H, m), 1.76-1.99 (2H, m), 2.93 (2H, t, J=7.5 Hz), 4.39 (2H, q, J=7.5 Hz), 5.50 (2H, s), 6.98 (1H, d, J=1Hz), 7.08 (1H, d, J=1Hz), 7.20 (2H, d, J=8 Hz), 7.84 (1H, d, J=8 Hz), 7.98-8.11 (2H, m)

(2)
3-[4-(4-Bromo-2-cyano-1-pyrrolyl)benzyl]-2-butyl-5-chloro-3H-imidazo[4,5-b]pyridine mp: 140°-141° C.

NMR (CDCl$_3$, δ): 0.98 (3H, t, J=7.5 Hz), 1.31-1.53 (2H, m), 1.70-1.92 (2H, m), 2.88 (2H, t, J=7.5 Hz), 5.52 (2H, s), 6.98 (1H, d, J=1Hz), 7.06 (1H, d, J=1Hz), 7.22-7.48 (5H, m), 8.04 (1H, d, J=8 Hz)

(3)
3-[4-(4-Bromo-2-cyano-1-pyrrolyl)benzyl]-2-butyl-5-methoxy-3H-imiazo[4,5-b]pyridine mp: 140°-143° C.

NMR (CDCl$_3$, δ): 0.92 (3H, t, J=7.5 Hz), 1.30-1.54 (2H, m), 1.70-1.90 (2H, m), 2.82 (2H, t-like, J=7.5 Hz), 3.98 (3H, s), 5.48 (2H, s), 6.72 (1H, d, J=10 Hz), 6.98 (1H, d, J=1Hz), 7.04 (1H, d, J=1Hz), 7.30-7.47 (4H, m), 7.94 (1H, d, J=10 Hz)

Preparation 49

To a solution of 4-(4-methylphenyl)pyrrole-3-carbonitrile (2.0 g) in a mixture of benzene (40 ml) and 50% aqueous sodium hydroxide solution (10 ml) was added methyliodide (1.56 g) and tetrabutylammonium iodide (4.06 g) in that order in an ice bath. The mixture was stirred for 3 hours at ambient temperature and extracted twice with diethyl ether. The combined organic layers were washed with aqueous hydrochloric acid and then water, dried, and concentrated in vacuo to yield 1-methyl-4-(4-methylphenyl)pyrrole-3-carbonitrile (2.03 g) as pale yellow crystals.

mp: 93°-94° C.

NMR (CDCl$_3$, δ): 2.38 (3H, s), 3.72 (3H, s), 6.78 (1H, d, J=2 Hz), 7.14 (1H, d, J=2 Hz), 7.21 (2H, d, J=8 Hz), 7.52 (2H, d, J=8 Hz)

Preparation 50

A mixture of 1-methyl-4-(4-methylphenyl)pyrrole-3-carbonitrile (2.0 g), 2,2'-azobis(4-methoxy-2,4-dimethylvaleronitrile (200 mg) and N-bromosuccinimide (1.91 g) in carbon tetrachloride (40 ml) was refluxed under nitrogen atmosphere, cooled to ambient temperature, and filtered. The filtrate was washed with 5% sodium thiosulfate solution and water. The separated oil was extracted with carbon tetrachloride, dried, and evaporated under reduced pressure to give a mixture of 2-bromo-1-methyl-3-(4-methylphenyl)pyrrole-4-carbonitrile and 2-bromo-1-methyl-4-(4-methylphenyl)pyrrole-3-carbonitrile.

mp: 113°-115° C.

NMR (CDCl$_3$, δ): 2.39 (3H, s), 3.70 (3H, s), 7.20-7.35 (3H, m), 7.45 (2H, d, J=8 Hz)

Preparation 51

The following compound was obtained according to a similar manner to that of Preparation 7.

A mixture of 2-bromo-3-(4-bromomethylphenyl)-1-methylpyrrole-4-carbonitrile and 2-bromo-4-(4-bromomethylphenyl)-1-methylpyrrole-3-carbonitrile mp: 146°-149° C.

NMR (CDCl$_3$, δ): 3.69 (3H, s), 4.51 (2H, s), 7.35 (1H, s), 7.49-7.57 (4H, m)

Preparation 52

The following compound was obtained according to a similar manner to that of Preparation 27.

A mixture of 2-bromo-1-methyl-3-[4-[N-(4-methyl-3-nitropyridin-2-yl)-N-butyrylamino]methylphenyl]pyrrole-4-carbonitrile and 2-bromo-1-methyl-4-[4-[N-(4-methyl-3-nitropyridin-2-yl)-N-butyrylamino]methylphenyl]pyrrole-3-carbonitrile.

NMR (CDCl$_3$, δ): 0.89 (3H, t, J=7.5 Hz), 1.55-1.85 (2H, m), 2.00-2.24 (2H, br peak), 2.43 (3H, s), 3.70 (3H, s), 4.90-5.35 (2H, br peak), 7.00-7.64 (6H, m), 8.37-8.52 (1H, m)

Preparation 53

The following compound was obtained according to a similar manner to that of Preparation 28.

A mixture of 3-[4-(2-bromo-4-cyano-1-methyl-3-pyrrolyl)benzyl]-7-methyl-2-propyl-3H-imidazo[4,5-b]pyridine and 3-[4-(2-bromo-3-cyano-1-methyl-4-pyrrolyl)benzyl]-7-methyl-2-propyl-3H-imidazo[4,5-b]pyridine.

mp: 105°-108° C.

NMR (CDCl$_3$, δ): 1.00 (3H, t, J=7.5 Hz), 1.69-1.92 (2H, m), 2.70 (3H, s), 3.69 (3H, s), 5.52 (2H, s), 7.02 (1H, d, J=5 Hz), 7.18 (2H, d, J=8 Hz), 7.30 (1H, s), 7.48 (2H, d, J=8 Hz), 8.21 (1H, d, J=5 Hz)

Preparation 54

A solution of the mixture prepared by Preparation 53 (300 mg) in methanol (15 ml) was hydrogenated over 10% palladium on carbon (300 mg) under a hydrogen atmosphere (3 atm) for 8 hours. The catalyst was filtered off and the filtrate was evaporated under reduced pressure. The residue was purified by preparative thin layer chromatography to give 3-[4-(4-cyano-1-methyl-3-pyrrolyl)benzyl]-7-methyl-2-propyl-3H-imidazo[4,5-b]pyridine (117 mg) as crystals.

mp: 117°-120° C.

NMR (CDCl$_3$, δ): 1.00 (3H, t, J=7.5 Hz), 1.69-1.91 (2H, m), 2.71 (3H, s), 2.86 (2H, t, J=7.5 Hz), 3.71 (3H, s), 5.51 (2H, s), 6.76 (1H, d, J=2 Hz), 7.06 (1H, d, J=5 Hz), 7.10-7.20 (3H, m), 7.53 (2H, d, J=9 Hz), 8.22 (1H, d, J=5 Hz)

Preparation 55

To a solution of 1-(4-ethoxycarbonylphenyl)-4-formylpyrrole-2-carbonitrile (2.0 g) in 1,2-dichloroethane (10 ml) was added sodium borohydride (296 mg) in one portion under nitrogen at ambient temperature. The mixture was stirred for one hour at the same temperature and then quenched with aqueous saturated ammonium chloride solution at 5° C. The organic layer was washed with water and brine, dried, and concentrated in vacuo. The residue was purified by silica gel column chromatography eluted by a mixture of ethyl acetate and n-hexane (2:1) to give 1-(4-ethoxycarbonylphenyl)-4-hydroxymethylpyrrole-2-carbonitrile (1.3 g) as a white solid.

mp: 120°-121.5° C.

NMR (CDCl$_3$, δ): 1.43 (3H, t, J=7.0 Hz), 4.42 (2H, q, J=7.0 Hz), 4.65 (2H, s), 7.04 (1H, d, J=1.0 Hz), 7.18 (1H, d, J=1.0 Hz), 7.55 (2H, d, J=9.0 Hz), 8.20 (2H, d, J=9.0 Hz)

Preparation 56

To a solution of 1-(4-ethoxycarbonylphenyl)-4-hydroxymethylpyrrole-2-carbonitrile (500 mg) in dichloromethane (5.5 ml) was added trifluoroacetic acid (2.8 ml) and triethylsilane (652 μl) in that order at 5° C. under nitrogen. The mixture was stirred at 5° C. for one and half hours and at ambient temperature for one hour and then poured into a mixture of diethyl ether and n-hexane (1:1). The mixture was washed with saturated sodium bicarbonate solution and brine, dried, and concentrated in vacuo. The residue was purified by column chromatography on silica gel (elution by ethyl acetate/n-hexane=1/10) to yield 1-(4-ethoxycarbonylphenyl)-4-methylpyrrole-2-carbonitrile (163 mg) as a white solid.

mp: 72°-75.5° C.

NMR (CDCl$_3$, δ): 1.42 (3H, t, J=7.0 Hz), 2.16 (3H, s), 4.41 (2H, q, J=7.0 Hz), 6.87 (1H, d, J=1.0 Hz), 6.93 (1H, d, J=1.0 Hz), 7.52 (2H, d, J=9.0 Hz), 8.19 (2H, d, J=9.0 Hz)

Preparation 57

The following compound was obtained according to a similar manner to that of Preparation 56.

1-(4-Ethoxycarbonylphenyl)-5-methylpyrrole-2-carbonitrile mp: 99°–104° C.

NMR (CDCl$_3$, δ): 1.42 (3H, t, J=7.0 Hz), 2.18 (3H, s), 4.42 (2H, q, J=7.0 Hz), 6.11 (1H, d, J=4.5 Hz), 6.90 (1H, d, J=4.5 Hz), 7.40 (2H, d, J=9.0 Hz), 8.21 (2H, d, J=9.0 Hz)

Preparation 58

The following compounds were obtained according to a similar manner to that of Preparation 37.

(1)

1-(4-Hydroxymethylphenyl)-4-methylpyrrole-2-carbonitrile mp: 89°–95° C.

NMR (CDCl$_3$, δ): 1.76 (1H, br s), 2.16 (3H, s), 4.75 (2H, s), 6.81 (1H, d, J=1.0 Hz), 6.87 (1H, d, J=1.0 Hz), 7.41 (2H, d, J=9.0 Hz), 7.49 (2H, d, J=9.0 Hz)

(2)

1-(4-Hydroxymethylphenyl)-5-methylpyrrole-2-carbonitrile

NMR (CDCl$_3$, δ): 1.99 (1H, br), 2.15 (3H, s), 4.79 (2H, d, J=5.5 Hz), 6.08 (1H, d, J=4.5 Hz), 6.87 (1H, d, J=4.5 Hz), 7.31 (2H, d, J=9.0 Hz), 7.52 (2H, d, J=9.0 Hz)

(3)

3-Chloro-1-(4-hydroxymethylphenyl)-2-methylpyrrole-5-carbonitrile

NMR (CDCl$_3$, δ): 1.89 (1H, br s), 2.12 (3H, s), 4.80 (2H, s), 6.86 (1H, s), 7.29 (2H, d, J=9.0 Hz), 7.53 (2H, d, J=9.0 Hz)

Preparation 59

The following compound was obtained according to a similar manner to that of Preparation 41.

1-(4-Chloromethylphenyl)-4-methylpyrrole-2-carbonitrile mp: 115°–120° C.

NMR (CDCl$_3$, δ): 2.15 (3H, s), 4.63 (2H, s), 6.82 (1H, d, J=1.0 Hz), 6.88 (1H, d, J=1.0 Hz), 7.42 (2H, d, J=9.0 Hz), 7.52 (2H, d, J=9.0 Hz)

Preparation 60

To a solution of 1-(4-hydroxymethylphenyl)-5-methylpyrrole-2-carbonitrile (890 mg) in dichloromethane (9 ml) was added triethylamine (794 μl) and methanesulfonyl chloride (343 μl) at 0° C. under nitrogen atmosphere. The mixture was stirred at 0° C. for an hour and then dichloromethane was added therein. The mixture was stirred and washed with water twice and brine, dried over magnesium sulfate and concentrated in vacuo to give 1-(4-methanesulfonyloxymethylphenyl)-5-methylpyrrole-2-carbonitrile (1.19 g).

NMR (CDCl$_3$, δ): 2.18 (3H, s), 3.03 (3H, s), 5.31 (2H, s), 6.10 (1H, d, J=4.5 Hz), 6.89 (1H, d, J=4.5 Hz), 7.37 (2H, d, J=9.0 Hz), 7.59 (2H, d, J=9.0 Hz)

Preparation 61

The following compounds were obtained according to a similar manner to that of Preparation 60.

(1)

3-Chloro-1-(4-methanesulfonyloxymethylphenyl)-2-methylpyrrole-5-carbonitrile

NMR (CDCl$_3$, δ): 2.12 (3H, s), 3.04 (3H, s), 5.31 (2H, s), 6.87 (1H, s), 7.37 (2H, d, J=9.0 Hz), 7.61 (2H, d, J=9.0 Hz)

(2)

1-(4-Methanesulfonyloxymethylphenyl)-5-methylthiopyrrole-2-carbonitrile mp: 95°–98° C.

NMR (CDCl$_3$, δ): 2.20 (3H, s), 2.94 (3H, s), 5.24 (2H, s), 6.24 (1H, d, J=5 Hz), 6.90 (1H, d, J=5 Hz), 7.38 (2H, d, J=8 Hz), 7.51 (2H, d, J=8 Hz)

Preparation 62

The following compound was obtained according to a similar manner to that of Preparation 27.

2-[N-Butyryl-N-[4-(2-cyano-4-methyl-1-pyrrolyl)benzyl]amino]-4-methyl-3-nitropyridine NMR (CDCl$_3$, δ): 0.88 (3H, t, J=7.0 Hz), 1.56–1.80 (2H, m), 2.02–2.19 (2H, m), 2.12 (3H, s), 2.43 (3H, s), 4.72–5.30 (2H, m), 6.78–6.91 (3H, m), 7.26–7.53 (4H, m), 8.46–8.57 (1H, m)

Preparation 63

The following compound was obtained according to a similar manner to that of Preparation 28.

3-[4-(2-Cyano-4-methyl-1-pyrrolyl)benzyl]-7-methyl-2-propyl-3H-imidazo[4,5-b]pyridine NMR (CDCl$_3$, δ): 1.01 (3H, t, J=7.5 Hz), 1.71–1.92 (2H, m), 2.11 (3H, s), 2.70 (3H, s), 2.83 (2H, t, J=7.5 Hz), 5.54 (2H, s), 6.79 (2H, d, J=1.0 Hz), 7.06 (1H, d, J=5.0 Hz), 7.23 (2H, d, J=9.0 Hz), 7.36 (2H, d, J=9.0 Hz), 8.21 (1H, d, J=5.0 Hz)

Preparation 64

The following compound was obtained according to a similar manner to that of Preparation 3.

1-(4-Ethoxycarbonylphenyl)pyrrole-2-carbaldehyde mp: 66°–69° C.

NMR (CDCl$_3$, δ): 1.41 (3H, t, J=7.0 Hz), 4.41 (2H, q, J=7.0 Hz), 6.44 (1H, dd, J=4.0 & 3.0 Hz), 7.11 (1H, dd, J=3.0 & 1.0 Hz), 7.19 (1H, dd, J=4.0 & 1.0 Hz), 7.41 (2H, d, J=9.0 Hz), 8.16 (2H, d, J=9.0 Hz), 9.60 (1H, s)

Preparation 65

The following compound was obtained according to a similar manner to that of Preparation 55.

1-(4-Ethoxycarbonylphenyl)-2-hydroxymethylpyrrole

NMR (CDCl$_3$, δ): 1.41 (3H, t, J=7.5 Hz), 4.40 (2H, q, J=7.5 Hz), 4.54 (2H, s), 6.29 (1H, dd, J=4.0 & 3.0 Hz), 6.37 (1H, dd, J=4.0 & 1.0 Hz), 6.92 (1H, dd, J=3.0 & 1.0 Hz), 7.60 (2H, d, J=9.0 Hz), 8.15 (2H, d, J=9.0 Hz)

Preparation 66

To a solution of 1-(4-ethoxycarbonylphenyl)-2-hydroxymethylpyrrole (8.97 g) in dichloromethane (90 ml) was added triethylamine (12.1 ml), 4-dimethylaminopyridine (100 mg) and tert-butylchlorodiphenylsilane (10.6 ml) in that order at 5° C. under nitrogen atmosphere. After stirring for half an hour at 5° C., the mixture was allowed to warm to ambient temperature and stirred for 13.5 hours. The mixture was washed with water and brine, dried, concentrated in vacuo. The residue was purified by column chromatography on silica gel (elution by ethyl acetate/n-hexane=1/7) to yield 2-tert-butyldiphenylsilyloxymethyl-1-(4-ethoxycarbonylphenyl)pyrrole (18.67 g) as an oil.

NMR (CDCl$_3$, δ): 1.02 (9H, s), 1.44 (3H, t, J=7.5 Hz), 4.43 (2H, q, J=7.5 Hz), 4.56 (2H, s), 6.13 (1H, dd, J=4.0 & 1.0 Hz), 6.23 (1H, dd, J=4.0 & 3.5 Hz), 6.90 (1H, dd, J=3.5 & 1.0 Hz), 7.30–7.48 (6H, m), 7.59–7.76 (6H, m), 8.12 (2H, d, J=9.0 Hz)

Preparation 67

The following compound was obtained according to a similar manner to that of Preparation 19.

2-tert-Butyldiphenylsilyloxymethyl-1-[4-ethoxycarbonylphenyl)pyrrole-2-carbonitrile NMR (CDCl$_3$, δ): 0.98 (9H, s), 1.46 (3H, t, J=7.5 Hz), 4.43 (2H, q, J=7.5 Hz), 4.45 (2H, s), 6.19 (1H, d, J=4.0 Hz), 6.91 (1H, d, J=4.0 Hz), 7.29–7.59 (10H, m), 7.77 (2H, d, J=9.0 Hz), 8.16 (2H, d, J=9.0 Hz)

Preparation 68

To a solution of 2-tert-butyldiphenylsilyloxymethyl-1-(4-ethoxycarbonylphenyl)pyrrole-2-carbonitrile (1.9 g) in tetrahydrofuran (19 ml) was added tetrabutylammonium fluoride (5.6 ml, 1M tetrahydrofuran solution) through syringe at ambient temperature. The mixture was stirred for half an hour at the same temperature and concentrated in vacuo. The residue was dissolved in ethyl acetate and the solution was washed with aqueous hydrochloric acid, water and brine, and then dried, and concentrated in vacuo. The oily residue was chromatographed on silica gel (elution by ethyl acetate/n-hexane =1/1) to give 1-(4-ethoxycarbonylphenyl)-5-hydroxymethylpyrrole-2-carbonitrile (702.5 mg) as an oil.

NMR (CDCl$_3$, δ): 1.42 (3H, t, J=7.0 Hz), 4.44 (2H, q, J=7.0 Hz), 4.49 (2H, s), 6.40 (1H, d, J=4.5 Hz), 6.97 (1H, d, J=4.5 Hz), 7.54 (2H, d, J=9.0 Hz), 8.23 (2H, d, J=9.0 Hz)

Preparation 69

The following compound was obtained according to a similar manner to that of Preparation 68.

1-(4-Hydroxymethylphenyl)-5-methylthiopyrrole-2-carbonitrile mp: 88°–91° C.

NMR (CDCl$_3$, δ): 2.28 (3H, s), 4.81 (2H, s), 6.30 (1H, d, J=5 Hz), 6.96 (1H, d, J=5 Hz), 7.39 (2H, d, J=8 Hz), 7.53 (2H, d, J=8 Hz)

Preparation 70

The following compounds were obtained according to a similar manner to that of Preparation 9.

(1)

3-[4-(2-Cyano-5-methyl-1-pyrrolyl)benzyl]-7-methyl-2-propyl-3H-imidazo[4,5-b]pyridine NMR (CDCl$_3$, δ): 1.00 (3H, t, J=7.0 Hz), 1.69–1.91 (2H, m), 2.10 (3H, s), 2.72 (3H, s), 2.87 (2H, t, J=7.0 Hz), 5.57 (2H, s), 6.06 (1H, d, J=4.5 Hz), 6.86 (1H, d, J=4.5 Hz), 7.08 (1H, d, J=5.0 Hz), 7.28 (4H, s), 8.23 (1H, d, J=5.0 Hz)

(2)

3-[4-(3-Chloro-5-cyano-2-methyl-1-pyrrolyl)benzyl]-7-methyl-2-propyl-3H-imidazo[4,5-b]pyridine NMR (CDCl$_3$, δ): 1.00 (3H, t, J=7.5 Hz), 1.70–1.91 (2H, m), 2.08 (3H, s), 2.71 (3H, s), 2.87 (2H, t, J=7.5 Hz), 5.57 (2H, s), 6.83 (1H, s), 7.08 (1H, d, J=5.0 Hz), 7.23 (2H, d, J=9.0 Hz), 7.31 (2H, d, J=9.0 Hz), 8.23 (1H, d, J=5.0 Hz)

(3)

3-[4-(2-Cyano-5-methylthio-1-pyrrolyl)benzyl]-7-methyl-2-propyl-3H-imidazo[4,5-b]pyridine NMR (CDCl$_3$, δ): 1.00 (3H, t, J=7.5 Hz), 1.68–1.90 (2H, m), 2.21 (3H, s), 2.70 (3H, s), 2.82 (2H, t, J=7.5 Hz), 5.58 (2H, s), 6.28 (1H, d, J=5 Hz), 6.91 (1H, d, J=5 Hz), 7.06 (1H, d, J=5 Hz), 7.22–7.48 (4H, m), 8.22 (1H, d, J=5 Hz)

(4)

2-Butyl-3-[4-[2-cyano-5-methyl-1-pyrrolyl)benzyl]-7-methyl-3H-imidazo[4,5-b]pyridine NMR (CDCl$_3$, δ): 0.91 (3H, t, J=7 Hz), 1.41 (2H, m), 1.75 (2H, m), 2.10 (3H, s), 2.71 (3H, s), 2.87 (2H, t, J=7 Hz), 5.58 (2H, s), 6.05 (1H, d, J=4 Hz), 6.86 (1H, d, J=4 Hz), 7.07 (1H, d, J=5 Hz), 7.28 (4H, s), 8.23 (1H, d, J=5 Hz)

(5)

3-[4-(4-Chloro-2-cyano-1-pyrrolyl)benzyl]-2-ethyl-5,7-dimethyl-3H-imidazo[4,5-b]pyridine NMR (CDCl$_3$, δ): 1.34 (3H, t, J=7.5 Hz), 2.61 (3H, s), 2.68 (3H, s), 2.87 (2H, q, J=7.5 Hz), 5.53 (2H, s), 6.89 (1H, d, J=1Hz), 6.95 (1H, s), 7.00 (1H, d, J=1Hz), 7.28 (2H, d, J=8 Hz), 7.38 (2H, d, J=8 Hz)

(6)

3-[4-(2-Cyano-4-difluoromethyl-1-pyrrolyl)benzyl]-7-methyl-2-propyl-3H-imidazo[4,5-b]pyridine NMR (CDCl$_3$, δ): 1.02 (3H, t, J=7.5 Hz), 1.72–1.98 (2H, m), 2.75 (3H, s), 2.93 (2H, t, J=7.5 Hz), 5.59 (2H, s), 6.68 (1H, t, J=56 Hz), 7.05–7.18 (2H, m), 7.18–7.37 (3H, m), 7.37–7.49 (2H, m), 8.29 (1H, d, J=5 Hz)

Preparation 71

To a suspension of 1-(4-ethoxycarbonylphenyl)-5-methylpyrrole-2-carbonitrile (1.76 g) and silica gel (8.0 g, Mallinckrodt) in tetrachloromethane (26 ml) was added dropwise sulfuryl chloride (760 μl) at 5° C. under nitrogen atmosphere. The suspension was stirred at 5° C. for one hour and then at ambient temperature for half an hour. The mixture was filtered off and washed with a little amount of tetrachloromethane. The filtrate was concentrated in vacuo and the residue was purified by column chromatography on silica gel (elution by ethyl acetate/n-hexane =1/7) to yield 4-chloro-1-(4-ethoxycarbonylphenyl)-5-methylpyrrole-2-carbonitrile (1.36 g)

mp: 101°–106° C.

NMR (CDCl$_3$, δ): 1.42 (3H, t, J=7.0 Hz), 2.15 (3H, s), 4.43 (2H, q, J=7.0 Hz), 6.89 (1H, s), 7.38 (2H, d, J=9.0 Hz), 8.22 (2H, d, J=9.0 Hz)

Preparation 72

The following compound was obtained according to a similar manner to that of Preparation 16.

5-Bromo-1-(4-tert-butyldiphenylsilyloxymethyl-phenyl)pyrrole-2-carbaldehyde

NMR (CDCl$_3$, δ): 1.12 (9H, s), 4.86 (2H, s), 6.49 (1H, d, J=4 Hz), 7.11 (1H, d, J=4 Hz), 7.53–7.19 (10H, m), 7.78–7.67 (4H, m), 9.31 (1H, s)

Preparation 73

The following compound was obtained according to a similar manner to that of Preparation 4.

5-Bromo-1-(4-tert-butyldiphenylsilyloxymethyl-phenyl)pyrrole-2-carbonitrile

NMR (CDCl$_3$, δ): 1.13 (9H, s), 4.84 (2H, s), 6.37 (1H, d, J=4 Hz), 6.92 (1H, d, J=4 Hz), 7.54–7.23 (10H, m), 7.76–7.66 (4H, m)

Preparation 74

To a mixture of N,N,N'-N'-tetramethylethylenediamine (1.55 ml) and 5-bromo-1-(4-tert-butyldiphenylsilyloxymethylphenyl)pyrrole-2-carbonitrile (3.80 g) was added dropwise n-butyllithium solution (1.6M solution in n-hexane, 5.2 ml) during a period of 20 minutes at −60° C. under nitrogen atmosphere. The mixture was stirred for one hour at the same temperature and then dimethyldisulfide (1 ml) was added therein in one portion. The reaction mixture was allowed to warm to ambient temperature, stirred overnight at the same temperature and then poured into ice water. The separated oil was extracted with ethyl acetate. The organic layer was washed with water, dried, and concentrated in vacuo to give the residue, which was purified by column chromatography on silica gel to yield 1-(4-tert-butyldiphenylsilyloxymethylphenyl)-5-methylthiopyrrole-2-carbonitrile (1.94 g) as a solid.

mp: 145°–148° C.

NMR (CDCl$_3$, δ): 1.11 (9H, s), 2.27 (3H, s), 4.83 (2H, s), 6.30 (1H, d, J=5 Hz), 6.93 (1H, d, J=5 Hz), 7.29–7.53 (10H, m), 7.64–7.74 (4H, m)

Preparation 75

To a solution of diethylaminosulfur trifluoride (639 mg) in dichloromethane (10 ml) was added 4-formyl-1-(4-methylphenyl)pyrrole-2-carbonitrile (417 mg) in one portion at ambient temperature. The mixture was stirred for 6.5 hours at the same temperature and furthermore diethylaminosulfur trifluoride (0.5 ml) was added therein to complete the reaction. The mixture was stirred overnight at the same temperature and then washed with water. The organic layer was dried and concentrated in vacuo to give an oily residue, which was purified by flash column chromatography on silica gel (elution by n-hexane/ethyl acetate =9/1) to yield 4-difluoromethyl-1-(4-methylphenyl)pyrrole-2-carbonitrile (364 mg) as an yellow oil.

NMR (CDCl$_3$, δ): 2.43 (3H, s), 6.68 (1H, t, J=56 Hz), 7.09 (1H, br s), 7.24 (1H, br s), 7.33 (4H, s)

Preparation 76

The following compound was obtained according to a similar manner to that of Preparation 7.

1-(4-Bromomethylphenyl)-4-difluoromethylpyrrole-2-carbonitrile mp: 74°–76° C.

NMR (CDCl$_3$, δ): 4.53 (2H, s), 6.79 (1H, t, J=56 Hz), 7.12 (1H, br s), 7.28 (1H, br s), 7.45 (2H, d, J=10 Hz), 7.57 (2H, d, J=10 Hz)

Preparation 77

A mixture of 4-bromo-1-(4-methylphenyl)pyrrole-2-carbonitrile (3.66 g), sodium trifluoroacetate (7.62 g), cuprous iodide (5.34 g) and N-methylpyrrolidone (40 ml) was stirred at 200° C. under a nitrogen atmosphere for 11 hours. The mixture was filtered. The filtrate was poured into water and extracted with ethyl acetate twice. The combined organic layer was dried over magnesium sulfate and evaporated in vacuo. The residue was purified by silica gel column chromatography to afford 1-(4-methylphenyl)-4-trifluoromethylpyrrole-2-carbonitrile (0.98 g).

mp: 40°–42° C.

NMR (CDCl$_3$, δ): 2.44 (3H, s), 7.13 (1H, s like), 7.32 (5H, s)

Preparation 78

The following compound was obtained according to a similar manner to that of Preparation 7.

1-(4-Bromomethylphenyl)-4-trifluoromethylpyrrole-2-carbonitrile mp: 65°–68° C.

NMR (CDCl$_3$, δ): 4.53 (2H, s), 7.17 (1H, s like), 7.38 (1H, s like), 7.45 (2H, d, J=9 Hz), 7.60 (2H, d, J=9 Hz)

Preparation 79

The following compound was obtained according to a similar manner to that of Preparation 35.

1(4-Ethoxycarbonylphenyl)-5-formyl-4-methylpyrrole-2-carbonitrile mp: 105°–108° C.

NMR (CDCl$_3$, δ): 1.42 (3H, t, J=7.5 Hz), 2.46 (3H, s), 4.43 (2H, q, J=7.5 Hz), 6.82 (1H, s), 7.47 (2H, d, J=9.0 Hz), 8.23 (2H, d, J=9.0 Hz), 9.68 (1H, s)

Preparation 80

The following compound was obtained according to similar manners to those of Preparations 55 and 56, successively.

4,5-Dimethyl-1-[4-ethoxycarbonylphenyl)pyrrole-2-carbonitrile mp: 58°–59° C.

NMR (CDCl$_3$, δ): 1.41 (3H, t, J=7.5 Hz), 2.09 (6H, s), 4.43 (2H, q, J=7.5 Hz), 6.79 (1H, s), 7.40 (2H, d, J=9.0 Hz), 8.20 (2H, d, J=9.0 Hz)

Preparation 81

The following compound was obtained according to a similar manner to that of Preparation 71.

5-Chloro-1-(4-ethoxycarbonylphenyl)-4-methylpyrrole-2carbonitrile mp: 72°–75° C.

NMR (CDCl$_3$, δ): 1.42 (3H, t, J=7.5 Hz), 2.12 (3H, s), 4.42 (2H, q, J=7.5 Hz), 6.83 (1H, s), 7.46 (2H, d, J=9.0 Hz), 8.21 (2H, d, J=9.0 Hz)

Preparation 82

The following compound was obtained according to a similar manner to that of Preparation 16.

5-Bromo-1-(4-ethoxycarbonylphenyl)-4-methylpyrrole-2-carbonitrile mp: 68°–70.5° C.

NMR (CDCl₃, δ): 1.42 (3H, t, J=7.5 Hz), 2.13 (3H, s), 4.43 (2H, q, J=7.5 Hz), 6.86 (1H, s), 7.45 (2H, d, J=9.0 Hz), 8.21 (2H, d, J=9.0 Hz)

Preparation 83

The following compounds were obtained according to a similar manner to that of Preparation 37.

(1)

4,5-Dimethyl-1-(4-hydroxymethylphenyl)pyrrole-2-carbonitrile mp: 77.5°-82° C.

NMR (CDCl₃, δ): 2.05 (3H, s), 2.09 (3H, s), 4.74 (2H, s), 6.73 (1H, s), 7.27 (2H, d, J=9.0 Hz), 7.49 (2H, d, J=9.0 Hz)

(2)

5-Chloro-1-(4-hydroxymethylphenyl)-4-methylpyrrole-2-carbonitrile mp: 94°-99.5° C.

NMR (CDCl₃, δ): 1.85 (1H, t like), 2.11 (3H, s), 4.80 (2H, d, J=4.5 Hz), 6.80 (1H, s), 7.35 (2H, d, J=9.0 Hz), 7.56 (2H, d, J=9.0 Hz)

(3)

5-Bromo-1-(4-hydroxymethylphenyl)-4-methylpyrrole-2-carbonitrile mp: 84°-87.5° C.

NMR (CDCl₃, δ): 2.11 (3H, s), 4.80 (2H, s), 6.81 (1H, s), 7.32 (2H, d, J=9.0 Hz), 7.52 (2H, d, J=9.0 Hz)

Preparation 84

The following compounds were obtained according to a similar manner to that of Preparation 60.

(1)

4,5-Dimethyl-1-(4-methanesulfonyloxymethylphenyl)-pyrrole-2-carbonitrile mp: 91.5°-93.5° C.

NMR (CDCl₃, δ): 2.08 (6H, s), 3.01 (3H, s), 5.30 (2H, s), 6.75 (1H, s), 7.35 (2H, d, J=9.0 Hz), 7.58 (2H, d, J=9.0 Hz)

(2)

5-Chloro-1-(4-methanesulfonyloxymethylphenyl)-4-methylpyrrole-2-carbonitrile

NMR (CDCl₃, δ): 2.12 (3H, s), 3.02 (3H, s), 5.31 (2H, s), 6.81 (1H, s), 7.42 (2H, d, J=9.0 Hz), 7.61 (2H, d, J=9.0 Hz)

(3)

5-Bromo-1-(4-methanesulfonyloxymethylphenyl)-4-methylpyrrole-2-carbonitrile

NMR (CDCl₃, δ): 2.13 (3H, s), 3.01 (3H, s), 5.31 (2H, s), 6.84 (1H, s), 7.40 (2H, d, J=9.0 Hz), 7.59 (2H, d, J=9.0 Hz)

(4)

4-Ethoxycarbonyl-1-(4-methanesulfonyloxymethylphenyl)-2-(1-trityl-1H-tetrazol-5-yl)pyrrole NMR (CDCl₃, δ): 1.37 (3H, t, J=8 Hz), 2.92 (3H, s), 4.32 (2H, q, J=8 Hz), 5.19 (2H, s), 6.88-6.98 (6H, m), 7.18-7.39 (13H, m), 7.44 (1H, d, J=1.5 Hz), 7.55 (1H, d, J=1.5 Hz)

Preparation 85

To a solution of 2-butyrylamino-4,6-dimethyl-3-nitropyridine (2.49 g) in dimethylformamide (12.5 ml) was added sodium hydride (441 mg) in an ice-water bath. The mixture was stirred at room temperature for an hour, and a solution of 1-(4-methanesulfonyloxymethylphenyl)-5-methylpyrrole-2-carbonitrile (3.05 g) in dimethylformamide (15 ml) was dropwise therein. The reaction mixture was stirred at room temperature for 5.5 hours and was stood overnight. The separated oil was extracted with ethyl acetate. The extract were washed with brine, dried, and concentrated in vacuo. The residue was purified by flash column chromatography eluted by n-hexane/ethyl acetate (1/1) to give 2-[N-butyryl-N-[4-(2-cyano-5-methyl-1-pyrrolyl)benzyl]amino]-4,6-dimethyl-3-nitropyridine (2.75 g) as oil.

NMR (CDCl₃, δ): 0.89 (3H, t, J=7 Hz), 1.68 (2H, m), 2.10 (2H, m), 2.15 (3H, s), 2.36 (3H, s), 2.52 (3H, s), 4.73-5.32 (2H), 6.06 (1H, d, J=4 Hz), 6.86 (1H, d, J=4 Hz), 7.08-7.48 (5H)

Preparation 86

The following compounds were obtained according to a similar manner to that of Preparation 85.

(1)

2-[N-Butyryl-N-[4-(2-cyano-4,5-dimethyl-1-pyrrolyl)-benzyl]amino]-4-methyl-3-nitropyridine NMR (CDCl₃, δ): 0.88 (3H, t, J=7.5 Hz), 1.57-1.80 (2H, m), 1.98-2.20 (2H, m), 2.04 (3H, s), 2.06 (3H, s), 2.42 (3H, s), 4.62-5.38 (2H, m), 6.71 (1H, s), 7.07-7.55 (5H, m), 8.42-8.55 (1H, m)

(2)

4,6-Dimethyl-2-[N-propionyl-N-[4-(2-cyano-5-methyl-1-pyrrolyl)benzyl]amino]-3-nitropyridine NMR (CDCl₃, δ): 1.10 (3H, t, J=7 Hz), 2.13 (3H, s), 2.13-2 25 (2H, m), 2.36 (3H, s), 2.52 (3H, s), 4.66-5.40 (2H, m), 6.04 (1H, m), 6.83 (1H, m), 7.03-7.75 (5H, m)

Preparation 87

The following compounds were obtained according to a similar manner to that of Preparation 9.

(1)

3-[4-(2-Cyano-4-trifluoromethyl-1-pyrrolyl)benzyl]-7-methyl-2-propyl-3H-imidazo[4,5-b]pyridine NMR (CDCl₃, δ): 1.02 (3H, t, J=7 Hz), 1.83 (2H, dt, J-7 Hz, 7 Hz), 2.71 (3H, s), 2.86 (2H, t, J=7 Hz), 5.58 (2H, s), 7.08 (1H, d, J=5 Hz), 7.15 (1H, s like), 7.30 (2H, d, J=7 Hz), 7.32 (1H, s like), 7.40 (2H, d, J=7 Hz), 8.22 (1H, d, J=5 Hz)

(2)

3-[4-(4-Chloro-2-cyano-1-pyrrolyl)benzyl]-2-ethyl-7-methyl-3H-imidazo[4,5-b]pyridine NMR (CDCl₃, δ): 1.42 (3H, t, J=7.5 Hz), 2.75 (3H, s), 2.92 (2H, q, J=7.5 Hz), 5.58 (2H, s), 6.91 (1H, d, J=2 Hz), 7.01 (1H, d, J=2 Hz), 7.09 (1H, d, J=5 Hz), 7.31 (2H, d, J=9 Hz), 7.40 (2H, d, J=9 Hz), 8.25 (1H, d, J=5 Hz)

(3)

3-[4-(4-Chloro-2-cyano-1-pyrrolyl)benzyl]-2-propyl-3H-imidazo[4,5-b]pyridine

NMR (CDCl₃, δ): 1.03 (3H, t, J=7.5 Hz), 1.78-2.02 (2H, m), 2.84 (2H, t, J=7.5 Hz), 5.58 (2H, s), 6.90 (1H, d, J=1Hz), 7.00 (1H, d, J=1Hz), 7.20-7.45 (5H, m), 8.07 (1H, dd, J=8 Hz, 1Hz), 8.48 (1H, dd, J=5 Hz, 1Hz)

(4)

3-[4-(4-Chloro-2-cyano-1-pyrrolyl)benzyl]-5,7-dimethyl-2-propyl-3H-imidazo[4,5-b]pyridine NMR (CDCl₃, δ): 0.99 (3H, s), 1.67-1.90 (2H, m), 2.60 (3H, s), 2.64 (3H, s), 2.77 (2H, t, J=7.5 Hz), 5.52 (2H, s), 6.89 (1H, d, J=1Hz), 6.93 (1H, s), 7.00 (1H, d, J=1Hz), 7.26 (2H, d, J=9 Hz), 7.37 (2H, d, J=9 Hz)

(5)

3-[4-(5-Chloro-2-cyano-4-methyl-1-pyrrolyl)benzyl]-7-methyl-2-propyl-3H-imidazo[4,5-b]pyridine NMR (CDCl₃, δ): 1.00 (3H, t, J=7.5 Hz), 1.69-1.90 (2H, m), 2.09 (3H, s), 2.70 (3H, s), 2.82 (2H, t, J=7.5 Hz), 5.57 (2H, s), 6.77 (1H, s), 7.04 (1H, d, J=5.0 Hz), 7.28 (4H, s), 8.21 (1H, d, J=5.0 Hz)

(6)

3-[4-(5-Bromo-2-cyano-4-methyl-1-pyrrolyl)benzyl]-7-methyl-2-propyl-3H-imidazo[4,5-b]pyridine mp: 106°-109° C.

NMR (CDCl₃, δ): 1.00 (3H, t, J=7.5 Hz), 1.69-1.90 (2H, m), 2.10 (3H, s), 2.71 (3H, s), 2.85 (2H, t, J=7.5 Hz), 5.58 (2H, s), 6.80 (1H, s), 7.07 (1H, d, J=5.0 Hz), 7.28 (4H, s), 8.23 (1H, d, J=5.0 Hz)

(7)

3-[4-(2-Chloro-4-cyano-1-methyl-3-pyrrolyl]benzyl]-2-propyl-7-methyl-3H-imidazo[4,5-b]pyridine NMR (CDCl₃, δ) 1.00 (3H, t, J=7.5 Hz), 1.69-1.91 (2H, m), 2.69 (3H, s), 2.83 (2H, t, J=7.5 Hz), 3.67 (3H, s), 5.52 (2H, s), 7.03 (1H, d, J=5 Hz), 7.13-7.24 (3H, m), 7.51 (2H, d, J=9 Hz), 8.21 (1H, d, J=5 Hz)

Preparation 88

The following compounds were obtained according to a similar manner to that of Preparation 28.

(1)

3-[4-(2-Cyano-5-methyl-1-pyrrolyl)benzyl]-2-ethyl-5,7-dimethyl-3H-imidazo[4,5-b]pyridine mp: 182°-183.5° C.

NMR (CDCl₃, δ): 1.34 (3H, t, J=8 Hz), 2.09 (3H, s), 2.60 (3H, s), 2.65 (3H, s), 2.84 (2H, q, J=8 Hz), 5.53 (2H, s), 6.04 (1H, d, J=5 Hz), 6.85 (1H, d, J=5 Hz), 6.92 (1H, s), 7.22 (2H, d, J=7 Hz), 7.26 (2H, d, J=7 Hz)

(2)

3-[4-(2-Cyano-4,5-dimethyl-1-pyrrolyl)benzyl]-7-methyl-2-propyl-3H-imiazo[4,5-b]pyridine NMR (CDCl₃, δ): 0.99 (3H, t, J=7.5 Hz), 1.70-1.92 (2H, m), 2.00 (3H, s), 2.04 (3H, s), 2.70 (3H, s), 2.87 (2H, t, J=7.5 Hz), 5.57 (2H, s), 6.71 (1H, s), 7.06 (1H, d, J=5.0 Hz), 7.21 (2H, d, J=9.0 Hz), 7.28 (2H, d, J=9.0 Hz), 8.23 (1H, d, J=5.0 Hz)

(3)

3-[4-(2-Cyano-5-methyl-1-pyrrolyl)benzyl]-5,7-dimethyl-2-propyl-3H-imidazo[4,5-b]pyridine NMR (CDCl₃, δ): 0.97 (3H, t J=7 Hz) 1.76 (2H dt J=7 Hz, 7 Hz), 2.61 (3H, s), 2.65 (3H, s), 2.78 (2H, t, J=7 Hz), 5.53 (2H, s), 6.06 (1H, d, J=4 Hz), 6.86 (1H, d, J=4 Hz), 6.92 (1H, s), 7.28 (4H, s)

Preparation 89

The following compound was obtained according to a similar manner to that of Preparation 4.

1-(4-tert-Butyldiphenylsilyloxymethylphenyl)pyrrole-2-carbonitrile

NMR (CDCl₃, δ): 1.11 (9H, s), 4.82 (2H, s), 6.35 (1H, dd, J=5 Hz, 4 Hz), 6.99 (1H, dd, J=5 Hz, 2 Hz), 7.08 (1H, dd, J=4 Hz, 2 Hz), 7.30-7.53 (10H, m), 7.62-7.74 (4H, m)

Preparation 90

The following compound was obtained according to a similar manner to that of Preparation 1.

4-Bromo-1-(4-tert-butyldiphenylsilyloxymethylphenyl)pyrrole-2-carbonitrile mp: 88°-90° C.

NMR (CDCl₃, δ): 1.10 (9H, s), 4.81 (2H, s), 6.97 (1H, d, J=2 Hz), 7.09 (1H, d, J=2 Hz), 7.32-7.58 (10H, m), 7.65-7.80 (2H, m)

Preparation 91

A mixture of 4-bromo-1-(4-tert-butyldiphenylsilyloxymethylphenyl)pyrrole-2-carbonitrile (2.02 g) and trimethyltin azide (2.42 g) in xylene (20 ml) was stirred at 120° C. for 14 hours. After cooled to ambient temperature, the reaction mixture was concentrated in vacuo. To the residue was added trityl chloride (42 mg), triethylamine (50 μl) and methylene chloride (1 ml), and the mixture was treated in a conventional manner to give 4-bromo-1-(4-tert-butyldiphenylsilyloxymethylphenyl)-2-(1-trityl-1H-tetrazol-5-yl)pyrrole (1.63 g)

NMR (CDCl₃, δ): 1.12 (9H, s), 4.73 (2H, s), 6.84-7.51 (27H, m), 7.64-7.76 (4H, m)

Preparation 92

To a stirred solution of 4-bromo-1-(4-tert-butyldiphenylsilyloxymethylphenyl)-2-(1-trityl-1H-tetrazol-5-yl)pyrrole (500 mg) in a mixture of tetrahydrofuran (5 ml) and N,N,N',N'-tetramethylethylenediamine (0.19 ml) was added n-butyl lithium (0.41 ml; 1.6M in n-hexane) at −78° C. under nitrogen atmosphere and the mixture was stirred at the same temperature for half an hour. Ethyl chloroformate (0.3 ml) was added to the mixture at the same temperature and the resulting mixture was stirred at −78° C. for half an hour, at 0° C. for one hour and then at ambient temperature for two hours. The reaction was quenched with aqueous saturated sodium bicarbonate and diluted with ethyl acetate. The organic layer was washed with brine and dried over magnesium sulfate. After filtration, the filtrate was concentrated and the residue was purified by flash chromatography eluted with a mixture of ethyl acetate-n-hexane 1:9 (V/V) to give 1-(4-tert-butyldiphenylsilyloxymethylphenyl)-4-ethoxycarbonyl-2-(1-trityl-1H-tetrazol-5-yl)pyrrole (311 mg) as a colorless viscous oil.

NMR (CDCl₃, δ): 1.12 (9H, s), 1.36 (3H, t, J=8 Hz), 4.31 (2H, q, J=8 Hz), 4.72 (2H, s), 6.83-6.98 (4H, m), 7.09-7.46 (20H, m), 7.55 (1H, d, J=1Hz), 7.64-7.75 (4H, m)

Preparation 93

The following compound was obtained according to a similar manner to that of Preparation 68.

4-Ethoxycarbonyl-1-(4-hydroxymethylphenyl)-2-(1-trityl-1H-tetrazol-5-yl)pyrrole

NMR (CDCl₃, δ): 1.36 (3H, t, J=8 Hz), 4.31 (2H, q, J=8 Hz), 4.67 (2H, br d, J=4 Hz), 6.85-7.02 (13H, m), 7.13-7.39 (6H, m), 7.43 (1H, d, J=2 Hz), 7.55 (1H, d, J=5 Hz)

Preparation 94

To a stirred solution of diethyl cyanomethylphosphonate (96 ml) in 1,2-dimethoxyethane (375 ml) was added sodium hydride (60%: 22g) portionwise below 5° C. and the stirring was continued at 0° C. for half an hour and then at ambient temperature for half an hour. The reaction mixture was recooled to 0° C. and a solution of methyl p-formylbenzoate (75 g) in 1,2-dimethoxyethane (375 ml) was added to the reaction mixture below 6° C. The reaction mixture was quenched with saturated aqueous sodium bicarbonate and diluted with ethyl acetate. The organic layer was washed with water and aqueous saturated sodium bicarbonate and dried over magnesium sulfate and filtered. The solvent was removed in vacuo and the solid product was recrystallized from ethanol to give 4-methoxycarbonylcinnamonitrile (52.12 g) as a white needle.

mp: 141°-144° C.

NMR (CDCl$_3$, δ): 3.95 (3H, s), 6.00 (1H, d, J=17 Hz), 7.45 (1H, d, J=17 Hz), 7.53 (2H, d, J=9 Hz), 8.09 (2H, d, J=9 Hz)

Preparation 95

(4-Methoxycarbonylphenyl)-1H-pyrrole-3-carbonitrile (13.21 g) was prepared by reacting 4-methoxycarbonylcinnamonitrile (50 g) with p-tolylmethyl isocyanide (62.5 g) in a conventional manner.

mp: 171°-172° C.

NMR (CDCl$_3$, +CD$_3$OD, δ): 3.93 (3H, s), 7.04-7.11 (1H, m), 7.35-7.41 (1H, m), 7.73 (2H, d, J=9 Hz), 8.07 (2H, d, J=9 Hz)

Preparation 96

To a stirred solution of 4-(4-methoxycarbonylphenyl)-1H-pyrrole-3-carbonitrile (3.00 g) in N,N-dimethylformamide (25 ml) was added sodium hydride 60% oil dispersion: 559mg) at ambient temperature and the stirring was continued for half an hour at the same temperature. Iodomethane (1.99 g) was added to the mixture, and was stirred at ambient temperature for two hours. The reaction mixture was poured onto ice water and extracted with ethyl acetate and washed with 7% aqueous hydrochloric acid. The organic layer was dried over magnesium sulfate, filtered and concentrated in vacuo. The residue was recrystallized from ethanol to give 4-(4-methoxycarbonylphenyl)-1-methylpyrrole-3-carbonitrile (2.78 g) as pale yellow needles.

mp: 125°-126° C.

NMR (CDCl$_3$, δ): 3.75 (3H, s), 3.93 (3H, s), 6.91 (1H, d, J=2 Hz), 7.20 (1H, d, J=2 Hz), 7.70 (2H, d, J=9 Hz), 8.06 (2H, d, J=9 Hz)

Preparation 97

The following compound was obtained by reacting 4-(4-methoxycarbonylphenyl)-1-methylpyrrole-3-carbonitrile with thionyl chloride, silica gel and carbon tetrachloride in a conventional manner.

A mixture of 5-chloro-4-(4-methoxycarbonylphenyl)-1-methylpyrrole-3-carbonitrile and 2,5-dichloro-4-(4-methoxycarbonylphenyl)-1-methylpyrrole-3-carbonitrile.

NMR (CDCl$_3$, δ): 3.70, 3.71, 3.95, 7.24, 7.60-7.72, 8.07-8.17

Preparation 98

The following compounds were obtained according to a similar manner to that of Preparation 37.

(1)

5-Chloro-4-(4-hydroxymethylphenyl)-1-methylpyrrole-3-carbonitrile mp: 153°-155° C.

NMR (CDCl$_3$, δ): 3.69 (3H, s), 4.73 (2H, s), 7.21 (1H, s), 7.46 (2H, d, J=9 Hz), 7.59 (2H, d, J=9 Hz)

(2)

2,5-Dichloro-4-(4-hydroxymethylphenyl)-1-methylpyrrole-3-carbonitrile mp: 167°-170° C.

NMR (CDCl$_3$, δ): 3.68 (3H, s), 4.74 (2H, s), 7.46 (2H, d, J=9 Hz), 7.56 (2H, d, J=9 Hz)

Preparation 99

To a stirred solution of 5-chloro-4-(4-hydroxymethylphenyl)-1-methylpyrrole-3-carbonitrile (450 mg) in methylene chloride (20 ml) was added triphenylphosphine (1.44 g) and carbon tetrabromide (1.21 g) successively at 0° C. and the resulting yellow solution was stirred at the same temperature for a while. The mixture was washed with aqueous saturated sodium bicarbonate and water, dried over magnesium sulfate and filtered. The organic layer was concentrated in vacuo and the residue was purified by flash chromatography eluted with a mixture of ethyl acetate and n-hexane 1:4 (V/V) then with 1:3 (V/V) to give 4-(4-bromomethylphenyl)-5-chloro-1-methylpyrrole-3-carbonitrile (220 mg) as a white solid.

mp: 128°-133° C.

NMR (CDCl$_3$, δ): 3.70 (3H, s), 4.63 (2H, s), 7.22 (1H, s), 7.49 (2H, d, J=9 Hz), 7.59 (2H, d, J=9 Hz)

Preparation 100

To a stirred suspension of 2-formylamino-2-(4-methylphenyl)acetic acid (4.00 g) in acetic anhydride (45 ml) was added 2-chloroacrylonitrile (16.5 ml) at room temperature and the resulting suspension was heated at 90° C. for 2.5 hours. After cooling, the solvent was evaporated and the residue was washed with isopropyl ether. The mixture was filtered and the resulting solid was dissolved into ethyl acetate and the solution was washed with aqueous saturated sodium bicarbonate and water successively. The organic layer was dried with magnesium sulfate, filtered and concentrated in vacuo. The residue was purified by silica gel column chromatography eluted with n-hexane/methylene chloride 1:3 (V/V) to give 2-(4-methylphenyl)pyrrole-3-carbonitrile (0.73 g) as a colorless viscous oil.

NMR (CDCl$_3$, δ): 2.40 (3H, s), 6.50-6.58 (1H, m), 6.75-6.84 (1H, m), 7.27 (2H, d, J=9 Hz), 7.59 (2H, d, J=9 Hz), 8.68 (1H, br s)

Preparation 101

The following compound was obtained according to a similar manner to that of Preparation 96.

1-Ethyl-2-(4-methylphenyl)pyrrole-3-carbonitrile

NMR (CDCl$_3$, δ): 1.31 (3H, t, J=7 Hz), 2.40 (3H, s), 3.90 (2H, q, J=7 Hz), 6.47 (1H, d, J=4 Hz), 6.70 (1H, d, J=4 Hz), 7.28 (5H, s)

Preparation 102

The following compound was obtained according to a similar manner to that of Preparation 1.

A mixture of 5-bromo-1-ethyl-2-(4-methylphenyl)-pyrrole-3-carbonitrile and 4-bromo-1-ethyl-2-(4-methylphenyl)pyrrole-3-carbonitrile.

NMR (CDCl$_3$, δ): 1.23 (3H, t, J=7 Hz), 2.42 (3H, s), 3.95 (2H, q, J=7 Hz), 6.51 (0.63H, s), 7.28 (4.37H, s)

Preparation 103

The following compound was obtained according to a similar manner to that of Preparation 7.

A mixture of 5-bromo-2-(4-bromomethylphenyl)-1-ethylpyrrole-3-carbonitrile and 4-bromo-2-(4-bromomethylphenyl)-1-ethylpyrrole-3-carbonitrile (This compound was used to the next reaction without furthermore purification.)

Preparation 104

The following compounds were obtained according to a similar manner to that of Preparation 9.

(1) A mixture of 3-[4-(5-bromo-3-cyano-1-ethyl-2-pyrrolyl)benzyl]-7-methyl-2-propyl-3H-imidazo[4,5-b]pyridine and 3-[4-(4-bromo-3-cyano-1-ethyl-2-pyrrolyl)benzyl]-7-methyl-2-propyl-3H-imidazo[4,5-b]pyridine NMR (CDCl$_3$, δ): 1.00 (3H, t, J=7 Hz), 1.19 and 1.20 (total 3H, each t, J=7 Hz), 1.81 (2H, m), 2.75 (3H, s), 2.91 (2H, m), 3.90 (2H, q, J=7 Hz), 5.58 (2H, s), 6.50 (0.6H, s), 7.10 (1H, d, J=5 Hz), 7.28 (2H, d, J=8 Hz), 7.85 (2H, d, J=8 Hz), 8.24 and 8.26 (total 1H, each d, J=5 Hz)

(2) 3-[4-(5-Bromo-3-cyano-1-ethyl-2-pyrrolyl)benzyl]-7-methyl-2-propyl-3H-imidazo[4,5-b]pyridine NMR (CDCl$_3$, δ): 1.02 (3H, t, J=8 Hz), 1.20 (3H, t, J=7 Hz), 1.83 (2H, m), 2.73 (3H, s), 2.90 (2H, dd, J=8 Hz, 7 Hz), 3.90 (2H, d, J=7 Hz), 5.58 (2H, s), 6.51 (1H, s), 7.09 (1H, d, J=4 Hz), 7.25 (2H, d, J=8 Hz), 7.35 (2H, d, J=8 Hz), 8.25 (1H, d, J=4 Hz)

Preparation 105

A mixture of 3-[4-(5-bromo-3-cyano-1-ethyl-2-pyrrolyl)benzyl]-7-methyl-2-propyl-3H-imidazo[4,5-b]pyridine and 3-[4-(4-bromo-3-cyano-1-ethyl-2-pyrroloyl)benzyl]-7-methyl-2-propyl-3H-imiazo[4,5-b]pyridine was dissolved in methanol (15 ml) and hydrogenated with 10% palladium on charcoal (300 mg) and potassium hydroxide (180 mg) at atmospheric pressure at ambient temperature for two hours. Concentrated hydrochloric acid was added until the pH of the solution was adjusted to 1 and then triethylamine was added until the pH was alkaline. The mixture was filtered through celite and the filtrate was concentrated in vacuo. The residue was chromatographed on silica gel eluted with ethyl acetate to give 3-[4-(3-cyano-1-ethyl-2-pyrrolyl)benzyl]-7-methyl-2-propyl-3H-imidazo[4,5-b]pyridine as a colorless oil.

NMR (CDCl$_3$, δ): 1.01 (3H, t, J=7.0 Hz), 1.28 (3H, t, J=8 Hz), 1.82 (2H, m), 2.73 (3H, s), 2.91 (2H, t, J=7 Hz), 3.86 (2H, q, J=8 Hz), 5.58 (2H, s), 6.50 (1H, d, J=2 Hz), 6.70 (1H, d, J=2 Hz), 7.09 (1H, d, J=4 Hz), 7.24 (2H, d, J=8 Hz), 7.35 (2H, d, J=8 Hz), 8.25 (1H, d, J=4 Hz)

Preparation 106

To a solution of 4-bromotoluene (1.42 g) in dry tetrahydrofuran (15 ml) was added n-butyl lithium solution (1.6 M in n-hexane, 5.2 ml) through a syringe at −78° C. under nitrogen atmosphere. The solution was stirred for one hour at −78° C. and a solution of zinc chloride (1.130 in dry tetrahydrofuran (10 ml) was added dropwise through a cannula therein at the same temperature under nitrogen atmosphere. After stirring for one hour at ambient temperature, the mixture was added to a solution of tetrakis (triphenylphosphine) palladium(0) (320 mg) in dry tetrahydrofuran (10 ml) through a cannula at ambient temperature under nitrogen atmosphere. The reaction mixture was allowed to stand overnight at the same temperature and poured into aqueous 1N hydrochloric acid. The separated oil was extracted twice with ethyl acetate. The extracts were washed with water, dried, and concentrated in vacuo. The residue was purified by column chromatography on silica gel (elution by n-hexane/ethyl acetate=6/1) to give 3-(4-methylphenyl)furane-2-carbaldehyde (1.01 g) as a yellow oil.

NMR (CDCl$_3$, δ): 2.52 (3H, s), 6.72 (1H, d, J=2 Hz), 7.29 (2H, d, J=9 Hz), 7.47 (2H, d, J=9 Hz), 7.69 (1H, d, J=2 Hz), 9.75 (1H, s)

Preparation 107

A mixture of 3-(4-methylphenyl)furane-2-carbaldehyde (1.0 g), hydroxylamine hydrochloride (560 mg), and sodium acetate (660 mg) in 60% aqueous ethanol (10 ml) was stirred for one and half hours at 65° C. The mixture was concentrated in vacuo. The residue was dissolved in a mixture of ethyl acetate and aqueous sodium bicarbonate solution. The organic layer was washed with brine, dried, and concentrated in vacuo to give a yellow solid. A mixture of the solid and sodium acetate (56 mg) in acetic anhydride (10.5 ml) was refluxed for 5 hours and then evaporated in vacuo. The residue was purified by column chromatography on silica gel (elution by n-hexane/ethyl acetate=15/1) to yield 3-(4-methylphenyl)furane-2-carbonitrile (884 mg) as a yellow oil.

NMR (CDCl$_3$, δ): 2.40 (3H, s), 6.78 (1H, d, J=2 Hz), 7.27 (2H, d, J=9 Hz), 7.54–7.64 (3H, m)

Preparation 108

A mixture of 3-(4-methylphenyl)furane-2-carbonitrile (884 mg), N-bromosuccinimide (902 mg), and 2,2'-azobis-4-methoxy-2,4-dimethylvaleronitrile (130 mg) in dichloromethane (10 ml) was refluxed for 2 hours. The mixture was cooled to ambient temperature, washed with aqueous sodium bicarbonate solution and water successively, dried, and concentrated in vacuo. The residue was column chromatographed on silica gel (elution by n-hexane/dichloromethane=4/1) to give 3-(4-bromethylphenyl)furane-2-carbonitrile (905 mg) as a powder.

NMR (CDCl$_3$, δ): 4.51 (2H, s), 6.80 (1H, d, J=2 Hz), 7.50 (2H, d, J=9 Hz), 7.61 (1H, d, J=2 Hz), 7.69 (2H, d, J=9 Hz)

Preparation 109

A mixture of 2-amino-4-methyl-3-nitropyridine (5.0 g) and N,N-dimethylaniline (8.5 ml) was heated at 100° C. under nitrogen atmosphere. To the solution was added butyryl chloride (3.5 ml) and the mixture was stirred at 100° C. for 5 hours. After being cooled to room temperature, ethyl acetate was added to the reaction mixture. The organic layer was separated and washed successively with water and brine. The solution was dried over magnesium sulfate and the solvent was evaporated in vacuo. The residue was washed with n-hexane to give 2-butyrylamino-4-methyl-3-nitropyridine (7.0 g).

mp: 92.5°-99° C.

NMR (CDCl₃, δ): 1.01 (3H, t, J=7.5 Hz), 1.64-1.85 (2H, m), 2.43 (2H, t, J=7.5 Hz), 2.48 (3H, s), 7.10 (1H, d, J=5.0 Hz), 8.26 (1H, br s), 8.35 (1H, d, J=5.0 Hz)

Preparation 110

A solution of 2-butyrylamino-4-methyl-3-nitropyridine (7.0 g) and iron powder (17.5 g) in a mixture of acetic acid (14 ml) and ethanol (100 ml) was stirred at 90° C. for 3 hours under nitrogen atmosphere. After being cooled to room temperature, the reaction mixture was filtered through Celite and the filtrate was evaporated in vacuo. Ethyl acetate and saturated aqueous sodium hydrogencarbonate were added to the residue until pH 7-8 and the resulting suspension was filtered through Celite. The organic layer of the filtrate was separated, washed with brine and dried over magnesium sulfate. The solvent was evaporated in vacuo and the residue was purified with silica gel column chromatography (eluent:ethyl acetate) to give 7-methyl-2-propyl-3H-imidazo[4,5-b]pyridine (3.6 g).

mp: 108°-111° C.

NMR (CDCl₃δ): 1.09 (3H, t, J=7.5 Hz), 1.09-2.12 (2H, m), 2.72 (3H, s), 3.06 (2H, t, J=7.5 Hz), 7.07 (1H, d, J=5.0 Hz), 8.19 (1H, d, J=5.0 Hz)

Preparation 111

To a suspension of sodium hydride (150 mg, 60% oil dispersion) in dimethylsulfoxide (10 ml) was added 7-methyl-2-propyl-3H-imidazo[4,5-b]pyridine (595 mg) in one portion at ambient temperature under nitrogen atmosphere. The mixture was stirred for one hour at the same temperature and then a solution of 3-(4-bromomethyl)furan-2-carbonitrile (890 mg) in dimethylsulfoxide (10 ml) as added dropwise to the mixture. After stirring for 3 hours at ambient temperature, the mixture was poured into diluted hydrochloric acid. The separated oil was extracted four times with ethyl acetate. The combined organic layers were washed with water, dried, and concentrated in vacuo. The residue was purified by column chromatography on silica gel (elution by n-hexane/ethyl acetate=1/1) to yield 3-[4-(2-cyano-3-furyl)benzyl]-7-methyl-2-propyl-3H-imidazo[4,5-b]pyridine (555 mg) as an amorphous solid.

NMR (CDCl₃, δ): 1.00 (3H, t, J=7.5 Hz), 1.70-1.92 (2H, m), 2.70 (3H, s), 2.82 (2H, t, J=7.5 Hz), 5.53 (2H, s), 6.73 (1H, d, J=1 Hz), 7.05 (1H, d, J=5 Hz), 7.22 (2H, d, J=9 Hz), 7.53-7.68 (3H, m), 8.22 (1H, d, J=5 Hz)

Preparation 112

A mixture of 2-hydroxy-4'-methylbenzophenone (18.3 g), chloroacetonitrile (7.87 g) and potassium carbonate (14.2 g) in N,N'-dimethylformamide (183 ml) was stirred at ambient temperature for 5 hours and then poured into ice water. The separated oil was extracted with dichloromethane (×2). The organic layer were washed with water (×3), dried and concentrated in vacuo. The residue was purified by flash column chromatography on silica gel eluted with dichloromethane to give 2-cyanomethoxy-4'-methylbenzophenone (21.3 g) as a yellow oil.

NMR (CDCl₃, δ): 2.42 (3H, s), 4.72 (2H, s), 7.10-7.72 (8H, m)

Preparation 113

To a solution of 2-(4-methylphenyl)benzo[b]thiophene (896 mg) in freshly distillated tetrahydrofuran (15 ml) was added n-butyllithium (2.75 ml, 1.6 mol solution in n-hexane) through a syringe at −78° C. The solution was stirred at −78° C. for 10 minutes and then at ambient temperature for half an hour. To the deep red colored solution was added N,N-dimethylformamide (365mg) at 5° C. The mixture was stirred at ambient temperature for one hour, quenched with aqueous saturated ammonium chloride solution, and extracted with diethyl ether. The organic layer was washed with aqueous saturated ammonium chloride solution, dried, and concentrated in vacuo to give a yellow residue, which was purified by flash column chromatography on silica gel eluted with 50% n-hexane in dichloromethane to yield 2-(4-methylphenyl)benzo[b]thiophene-3-carbaldehyde (285 mg) as white crystals.

IR (Nujol): 1660 cm⁻¹

NMR (CDCl₃, δ): 2.50 (3H, s), 7.38 (2H, d, J=7.5 Hz), 7.45-7.60 (2H, m), 7.54 (2H, d, J=7.5 Hz), 7.90 (1H, dd, J=2 Hz and 7.5 Hz), 8.82 (1H, dd, J=2 Hz and 7.5 Hz), 10.1 (1H, s)

Preparation 114

The following compounds were obtained according to a similar manner to that of Preparation 3.

(1)

5-Chloro-3-(4-methylphenyl)thiophene-2-carbaldehyde

NMR (CDCl₃, δ): 2.43 (3H, s), 7.08 (1H, s), 7.28 (2H, d, J=8 Hz), 7.36 (2H, d, J=8 Hz), 9.77 (1H, s)

(2)

2-(4-Methylphenyl)imidazo[1,2-a]pyridine-3-carbaldehyde

NMR (CDCl₃, δ): 2.44 (3H, s), 7.13 (1H, dt, J=7 Hz and 1 Hz), 7.34 (2H, d, J=7 Hz), 7.59 (1H, ddd, J=8 Hz, 7 Hz and 1 Hz), 7.74 (2H, d, J=7 Hz), 7.83 (1H, dt, J=1 Hz and 8 Hz), 9.68 (1H, dd, J=7 Hz and 1 Hz), 10.07 (1H, s)

(3)

2-(4-Methylphenyl)indolizine-3-carbaldehyde

NMR (CDCl₃, δ): 2.41 (3H, s), 6.58 (1H, s), 6.91 (1H, t, J=6 Hz), 7.23 (1H, m), 7.26 (2H, d, J=8 Hz), 7.46 (2H, d, J=8 Hz), 7.55 (1H, d, J=8 Hz), 9.75 (1H, s), 9.84 (1H, d, J=6 Hz)

Preparation 115

The following compound was obtained according to a similar manner to that of the former half of Preparation 4.

2-(4-Methylphenyl)benzo[b]thiophene-3-carbaldehyde oxime mp: 155°-157° C.

NMR (CDCl₃, δ): 2.44 (3H, s), 7.29 (2H, d, J=9.5 Hz), 7.42 (2H, d, J=9.5 Hz), 7.34-7.50 (2H, m), 7.82 (1H, dd, J=2 Hz and 7.5 Hz), 8.35 (1H, s), 8.59 (1H, dd, J=2 Hz and 7.5 Hz)

Preparation 116

The following compound was obtained according to a similar manner to that of the latter half of Preparation 4.

2-(4-Methylphenyl)benzo[b]thiophene-3-carbonitrile mp: 104°–106° C.

IR (Nujol): 2200 cm$^{-1}$

NMR (CDCl$_3$, δ): 2.45 (3H, s), 7.31 (2H, d, J=7.5 Hz), 7.39–7.54 (2H, m), 7.79 (2H, d, J=7.5 Hz), 7.78–7.97 (2H, m)

Preparation 117

To a stirred solution of 2-picoline (5.12 g) in acetone (10 ml) was added 2-bromo-4'-methylacetophenone (10.4 g) in one portion and the mixture was heated at 80° C. for one hour. After addition of diethyl ether, the crystalline product was collected and washed with diethyl ether. After drying in air for several hours, this product was suspended in water (100 ml) and a solution of sodium bicarbonate (21 g) in water (100 ml) was added dropwise to the suspension. The mixture was stirred at ambient temperature for 45 minutes and refluxed for half an hour. The mixture was diluted with methylene chloride and washed with aqueous saturated sodium chloride. The organic layer was separated, dried over potassium carbonate and filtered. The solvent was removed in vacuo and the resulting solid was recrystallized from benzene to give 2-(4-methylphenyl)indolizine (7.51 g).

NMR (CDCl$_3$, δ): 2.36 (3H, s), 6.43 (1H, br t, J=6 Hz), 6.66 (2H, m), 7.20 (2H, d, J=8 Hz), 7.32 (1H, d, J=8 Hz), 7.54 (2H, d, J=8 Hz), 7.52 (1H, m), 7.89 (1H, br s)

Preparation 118

To a mixture of 2-cyanomethoxy-4'-methylbenzophenone (18.6 g) and molecular sieves (18 g) in benzene (270 ml) was added potassium tert-butoxide (8.31 g) in one portion at ambient temperature. After stirring at the same temperature for one hour, the mixture was filtered off. The filtrate was washed with diluted hydrochloric acid, dried, and concentrated in vacuo. The residue was purified by flash column chromatography to yield 3-(4-methylphenyl)benzo[b]furan-2-carbonitrile (1.82 g) as white crystals.

mp: 131°–133.5° C.

IR (Nujol): 2200 cm$^{-1}$

Preparation 119

A mixture of 2-pyridyl acetonitrile (5.0 g) and 2-bromo-4'-methylacetophenone (8.52 g) in acetone (10 ml) was heated at 80° C. for 24 hours, during which 2-pyridylacetonitrile (1 g, 2 g) was added to the reaction mixture. After being cooled, the solvent was removed in vacuo and the residue was chromatographed on silica gel eluted with a mixture of ethyl acetate and n-hexane (1:6 to 1:2, V/V) to give a solid product. This product was recrystallized from ethanol-water to give 2-(4-methylphenyl)indolizine-1-carbonitrile (4.1 g) as a pale brown powder.

mp: 107°–109° C.

NMR (CDCl$_3$, δ): 2.40 (3H, s), 6.75 (1H, dd, J=7 Hz and 1 Hz), 7.06 (1H, ddd, J=1 Hz, 7 Hz and 8 Hz), 7.26 (2H, d, J=8 Hz), 7.42 (1H, s), 7.65 (1H, m), 7.67 (2H, d, J=8 Hz), 8.00 (1H, br d, J=7 Hz)

Preparation 120

The following compounds were obtained according to a similar manner to that of Preparation 4.

(1)

5-Chloro-3-(4-methylphenyl)thiophene-2-carbonitrile

NMR (CDCl$_3$, δ): 2.41 (3H, s), 7.13 (1H, s), 7.28 (2H, d, J=8 Hz), 7.55 (2H, d, J=8 Hz)

(2)

2-(4-Methylphenyl)imidazo[1,2-a]pyridine-3-carbonitrile

NMR (CDCl$_3$, δ): 2.42 (3H, s), 7.09 (1H, dt, J=1 Hz and 7 Hz), 7.33 (2H, d, J=8 Hz), 7.46 (1H, ddd, J=1 Hz, 7 Hz and 8 Hz), 7.75 (1H, dd, J=1 Hz and 8 Hz), 8.09 (2H, d, J=8 Hz), 8.36 (1H, dd, J=1 Hz and 7 Hz)

(3)

2-(4-Methylphenyl)indolizine-3-carbonitrile

NMR (CDCl$_3$, δ): 2.40 (3H, s), 6.66 (1H, s), 6.81 (1H, dt, J=1 Hz and 7 Hz), 7.02 (1H, dt, J=1 Hz and 7 Hz), 7.39 (2H, d, J=8 Hz), 7.49 (1H, d, J=7 Hz), 7.71 (2H, d, J=8 Hz), 8.26 (1H, d, J=7 Hz)

Preparation 121

The following compound was obtained according to a similar manner to that of Preparation 35.

2-Formyl-3-(4-methoxycarbonylphenyl)-1-methylpyrrole-4-carbonitrile mp: 197°–200° C.

NMR (CDCl$_3$, δ): 3.97 (3H, s), 4.05 (3H, s), 7.35 (1H, s), 7.56 (2H, d, J=9 Hz), 8.17 (2H, d, J=9 Hz), 9.61 (1H, s)

Preparation 122

The following compound was obtained according to similar manners to those of Preparations 55 and 56, successively.

1,2-Dimethyl-3-(4-methoxycarbonylphenyl)pyrrole-4-carbonitrile mp: 135°–138° C.

NMR (CDCl$_3$, δ): 2.29 (3H, s), 3.62 (3H, s), 3.93 (3H, s), 7.17 (1H, s), 7.46 (2H, d, J=9 Hz), 8.10 (2H, d, J=9 Hz)

Preparation 123

The following compound was obtained according to a similar manner to that of Preparation 37.

1,2-Dimethyl-3-(4-hydroxymethylphenyl)pyrrole-4-carbonitrile

NMR (CDCl$_3$, δ): 1.78 (1H, br s), 2.27 (3H, s), 3.61 (3H, s), 4.71 (2H, s), 7.13 (1H, s), 7.34–7.48 (4H, m)

Preparation 124

The following compound was obtained according to a similar manner to that of Preparation 99.

3-(4-Chloromethylphenyl)-1,2-dimethylpyrrole-4-carbonitrile mp: 170°–177° C.

NMR (CDCl$_3$, δ): 2.27 (3H, s), 3.62 (3H, s), 4.63 (2H, s), 7.14 (1H, s), 7.34–7.50 (4H, m)

Preparation 125

The following compounds were obtained according to a similar manner to that of Preparation 96.

(1)

2-(4-Methylphenyl)-1-propylpyrrole-3-carbonitrile

NMR (CDCl$_3$, δ): 0.80 (3H, t, J=8 Hz), 1.56 (2H, m), 2.40 (3H, s), 3.32 (2H, t, J=8 Hz), 6.49 (1H, d, J=3 Hz), 6.69 (1H, d, J=3 Hz), 7.20–7.36 (4H, m)

(2)

1-Isopropyl-2-(4-methylphenyl)pyrrole-3-carbonitrile

NMR (CDCl$_3$, δ): 1.37 (6H, d, J=7 Hz), 2.41 (3H, s), 4.40 (1H, m), 6.50 (1H, d, J=4 Hz), 6.78 (1H, d, J=4 Hz), 7.28 (4H, s)

Preparation 126

The following compound was obtained according to similar manners to those of Preparation 7 and 27, successively.

A mixture of 4,6-dimethyl-3-nitro-2-[N-propionyl-N-[4-(4-bromo-3-cyano-1-ethyl-2-pyrrolyl)benzyl]amino]-pyridine and 4,6-dimethyl-3-nitro-2-[N-propionyl-N-[4-(5-bromo-3-cyano-1-ethyl-2-pyrrolyl)benzyl]amino]-pyridine.

(This mixture was used to the next reaction without further purification.)

Preparation 127

The following compound was obtained according to a similar manner to that of Preparation 27.

4,6-Dimethyl-2-[N-propionyl-N-[4-(2-chloro-4-cyano-1-methyl-3-pyrrolyl)benzyl]amino]-3-nitropyridine NMR (CDCl$_3$, δ): 1.11 (3H, t, J=7.5 Hz), 2.05–2.65 (8H, m), 3.68 (3H, s), 4.55–5.40 (2H, br), 6.88–7.68 (6H, m)

Preparation 128

The following compounds were obtained according to a similar manner to that of Preparation 50.

(1)

1-Bromo-2-(4-methylphenyl)indolizine-3-carbonitrile

NMR (CDCl$_3$, δ): 2.43 (3H, s), 6.88 (1H, dt, J=1 Hz and 7 Hz), 7.13 (1H, ddd, J=1 Hz, 7 Hz and 8 Hz), 7.30 (2H, d, J=8 Hz), 7.58 (1H, d, J=8 Hz), 7.62 (2H, d, J=8 Hz), 8.27 (1H, d, J=7 Hz)

(2) 3-Bromo-2-(4-methylphenyl)indolizine-1-carbonitrile

NMR (CDCl$_3$, δ): 2.42 (3H, s), 6.93 (1H, dt, J=0.5 and 7 Hz), 7.18 (1H, dt, J=0.5 Hz and 8 Hz), 7.32 (2H, d, J=7 Hz), 7.60 (2H, d. J=7 Hz1, 7.69 (1H, d, J=8 Hz), 8.21 (1H, d, J=7 Hz)

Preparation 129

The following compounds were obtained according to a similar manner to that of Preparation 1.

(1) A mixture of 4-bromo-2-(4-methylphenyl)-1-propylpyrrole-3-carbonitrile and 5-bromo-2-(4-methylphenyl)-1-propylpyrrole-3-carbonitrile (This mixture was used to the next reaction without further purification.)

(2) 4,5-Dibromo-1-isopropyl-2-(4-methylphenyl)pyrrole-3-carbonitrile (This compound was used to the next reaction without further purification.)

Preparation 130

A mixture of 3-(4-methylphenyl)benzo[b]furan-2-carbonitrile (239 mg), N-bromosuccinimide (182 mg), and 2,2'-azobisisobutyronitrile (10 mg) in carbon tetrachloride (5 ml) was refluxed for 5 hours and cooled to ambient temperature. The precipitates were filtered off. The filtrate was washed with aqueous sodium bicarbonate solution (×3), dried, and concentrated in vacuo to give a yellow oil, which was crystallized from n-hexane to yield 3-(4-bromomethylphenyl)benzo[b]furan-2-carbonitrile (300 mg) as a yellow solid.

NMR (CDCl$_3$, δ): 4.58 (2H, s), 7.38–7.88 (8H, m)

Preparation 131

The following compounds were obtained according to a similar manner to that of Preparation 130.

(1)

2-(4-Bromomethylphenyl)benzo[b]thiophene-3-carbonitrile

NMR (CDCl$_3$, δ): 4.56 (2H, s), 7.30–8.04 (8H)

(2)

3-(4-Bromomethylphenyl)-5-chloro-2-(1-trityl-1H-tetrazol-5-yl)thiophene

NMR (CDCl$_3$, δ): 4.48 (2H, s), 6.92–7.43 (20H)

(3)

2-(4-Bromomethylphenyl)-3-(1-trityl-1H-tetrazol-5-yl)imidazo[1,2-a]pyridine (This compound was used to the next reaction without further purification.)

(4)

1-Bromo-2-(4-bromomethylphenyl)indolizine-3-carbonitrile

NMR (CDCl$_3$, δ): 4.56 (2H, s), 6.92 (1H, dt, J=1 Hz and 7 Hz); 7.17 (1H, ddd, J=1 Hz, 7 Hz and 8 Hz), 7.54 (2H, d, J=7 Hz), 7.60 (1H, m), 7.71 (2H, d, J=7 Hz), 8.28 (1H, d, J=7 Hz)

(5)

3-Bromo-2-(4-bromomethylphenyl)indolizine-1-carbonitrile

NMR (CDCl$_3$, δ): 4.56 (2H, s), 6.95 (1H, dt, J=0.5 and 7 Hz), 7.19 (1H, ddd, J=0.5 Hz, 7 Hz and 8 Hz), 7.53 (2H, d, J=7 Hz), 7.65 (1H, m), 7.68 (2H, d, J=7 Hz), 8.24 (1H, d, J=7 Hz)

(6)

2-(4-Bromomethylphenyl)-4,5-dibromo-1-isopropylpyrrole-3-carbonitrile (This compound was used to the next reaction without further purification.)

Preparation 132

A mixture of 5-chloro-3-(4-methylphenyl)thiophene-2-carbonitrile (4.67 g), trimethyltin azide (12.3 g) and xylene (100 ml) was heated under reflux for 15 hours. After standing for 3 days at ambient temperature, the precipitate was collected by vacuum filtration to give 5-chloro-3-(4-methylphenyl)-2-(1H-tetrazol-5-yl)thiophene (14.7 g) as a yellowish powder. This powder was treated with trityl chloride (6.7 g) and 10N aqueous sodium hydroxide (2.4 ml) in dichloromethane (59 ml), and tetrahydrofuran (10 ml) at ambient temperature for 20 hours. The reaction mixture was washed with brine and dried over magnesium sulfate. The solvents were evaporated in vacuo to give a residue which was purified by silica gel column chromatography to afford 5-chloro-3-(4-methylphenyl)-2-(1-trityl-1H-tetrazol-5-yl)thiophene (10.3 g).

NMR (CDCl₃, δ): 2.35 (3H, s), 6.94–7.42 (20H)

Preparation 133

The following compound was obtained according to a similar manner to that of the former half of Preparation 132.

2-(4-Methylphenyl)-3-(1H-tetrazol-5-yl)imidazo[1,2-a]pyridine.

NMR (CDCl₃-CD₃OD, δ): 1.97 (3H, s), 6.84 (2H, d, J=8 Hz), 6.93 (1H, dt, J=1 Hz and 7 Hz), 7.12 (2H, d, J=8 Hz), 7.35 (1H, dt, J=1 Hz and 8 Hz), 8.56 (1H, ddd, J=1 Hz, 7 Hz and 8 Hz)

Preparation 134

The following compound was obtained according to a similar manner to that of the latter half of Preparation 32.

2-(4-Methylphenyl)-3-(1-trityl-1H-tetrazol-5-yl)imidazo[1,2-a]pyridine mp: 154°–156° C.

NMR (CDCl₃, δ): 2.93 (3H, s), 6.84 (1H, dd, J=1 Hz and 7 Hz), 6.96–7.11 (8H, m), 7.14–7.40 (10H, m), 7.59–7.74 (3H, m), 8.95 (1H, br d, J=7 Hz)

Preparation 135

The following compounds were obtained according to a similar manner to that of Preparation 9.

(1)
2-Butyl-3-[4-(2-cyano-3-benzo[b]furyl)benzyl]-3H-imidazo[4,5-b]pyridine

NMR (CDCl₃, δ): 0.92 (3H, t, J=7.5 Hz), 1.32–1.55 (2H, m), 1.74–1.95 (2H, m), 2.88 (2H, t, J=7.5 Hz), 5.60 (2H, s), 7.21–7.80 (9H, m), 8.05 (1H, dd, J=9.0 Hz, and 0.5 Hz), 8.37 (1H, dd, J=5.0 Hz and 0.5 Hz)

(2)
2-Butyl-3-[4-(3-cyano-2-benzo[b]thienyl)benzyl]-3H-imidazo[4,5-b]pyridine mp: 134°–135° C.

NMR (CDCl₃, δ): 0.94 (3H, t, J=7 Hz), 1.44 (2H, m), 1.86 (2H, m), 2.88 (2H, t, J=7 Hz), 5.60 (2H, s), 7.22–7.60 (6H), 7.86 (2H, d, J=8 Hz), 7.98 (1H, d, J=8 Hz), 8.07 (1H, d, J=8 Hz), 8.38 (1H, d, J=5 Hz)

(3)
2-Butyl-3-[4-(1-bromo-3-cyano-2-indolizinyl)benzyl]-3H-imidazo[4,5-b]pyridine NMR (CDCl₃, δ): 0.92 (3H, t, J=7 Hz), 1.44 (2H, m), 1.86 (2H, m), 2.94 (2H, t, J=7 Hz), 5.61 (2H, s), 6.90 (1H, dt, J=1 Hz and 7 Hz), 7.15 (1H, ddd, J=1 Hz, 7 Hz and 8 Hz), 7.28 (2H, d, J=7 Hz), 7.29 (1H, m), 7.57 (1H, d, J=8 Hz), 7.67 (2H, d, J=8 Hz), 8.13 (1H, d, J=8 Hz), 8.25 (1H, d, J=7 Hz), 8.43 (1H, dd, J=1 Hz and 6 Hz)

(4)
2-Butyl-3-[4-(3-bromo-1-cyano-2-indolizinyl)benzyl]-3H-imidazo[4,5-b]pyridine NMR (CDCl₃, δ): 0.91 (3H, t, J=7 Hz), 1.43 (2H, m), 1.86 (2H, m), 2.88 (2H, t, J=7 Hz), 5.63 (2H, s), 6.98 (1H, dd, J=1 Hz and 7 Hz), 7.21 (1H, dd, J=1 Hz and 8 Hz), 7.28 (1H, m), 7.31 (2H, d, J=7 Hz), 7.68 (2H, d, J=7 Hz), 7.70 (1H, m), 8.11 (1H, dd, J=7 Hz and 1 Hz), 8.24 (1H, d, J=7 Hz), 8.53 (1H, dd, J=5 Hz and 1 Hz)

(5)
3-[4-(4-Cyano-1,2-dimethyl-3-pyrrolyl)benzyl]-7-methyl-2-propyl-3H-imidazo[4,5-b]pyridine mp: 122°–124° C.

NMR (CDCl₃, δ): 1.00 (3H, t, J=7.5 Hz), 1.70–1.93 (2H, m), 2.20 (3H, s), 2.71 (3H, s), 2.86 (2H, t, J=7.5 Hz), 3.58 (3H, s), 5.53 (2H, s), 7.05 (1H, d, J=5 Hz), 7.10 (1H, s), 7.18 (2H, d, J=9 Hz), 7.32 (2H, d, J=9 Hz), 8.23 (1H, d, J=5 Hz)

(6)
3-[4-(3-Cyano-4,5-dibromo-1-isopropyl-2-pyrrolyl)benzyl]-7-methyl-2-propyl-3H-imidazo[4,5-b]pyridine NMR (CDCl₃, δ): 1.02 (3H, t, J=8 Hz), 1.48 (6H, d, J=7 Hz), 1.83 (2H, m), 2.72 (3H, s), 2.87 (2H, t, J=8 Hz), 4.49 (1H, m), 5.56 (2H, s), 7.07 (1H, d, J=5 Hz), 7.24 (2H, d, J=9 Hz), 7.39 (2H, d, J=9 Hz), 8.23 (1H, d, J=5 Hz)

(7)
3-[4-(2-Chloro-4-cyano-1-methyl-3-pyrrolyl)benzyl]-5,7-dimethyl-2-propyl-3H-imidazo[4,5-b]pyridine mp: 150°–152° C.

NMR (CDCl₃, δ): 0.99 (3H, t, J=7.5 Hz), 1.66–1.90 (2H, m), 2.61 (3H, s), 2.65 (3H, s), 2.80 (2H, m), 3.67 (3H, s), 5.50 (2H, s), 6.92 (1H, s), 7.11–7.23 (3H, m), 7.50 (2H, d, J=9 Hz)

Preparation 136

The following compound was obtained according to similar manners to those of Preparation 130 and 9, successively.

A mixture of 3-[4-(5-bromo-3-cyano-1-propyl-2-pyrrolyl)benzyl]-7-methyl-3-propyl-3H-imidazo[4,5-b]pyridine and 3-[4-(4-bromo-3-cyano-1-propyl-2-pyrrolyl)benzyl]-7-methyl-2-propyl-3H-imidazo[4,5-b]pyridine.

NMR (CDCl₃, δ): 0.67 (1.5H, t, J=8 Hz), 0.70 (1.5H, t, J=8 Hz), 0.99 (3H, t, J=8 Hz), 1.57 (2H, m), 1.83 (2H, m), 2.74 (3H, br s), 2.91 (2H, m), 3.86 (2H, m), 5.57 (2H, s), 6.50 (0.5H, s), 7.10 (1H, d, J=5 Hz), 7.19–7.41 (4.5H, m), 8.26 (0.5H, d, J=5 Hz), 8.27 (0.5H, d, J=5 Hz)

Preparation 137

The following compounds were obtained according to a similar manner to that of Preparation 28.

(1)
3-[4-(2-Chloro-4-cyano-1-methyl-3-pyrrolyl)benzyl]-5,7-dimethyl-2-ethyl-3H-imidazo[4,5-b]pyridine mp: 155°–157° C.

NMR (CDCl₃, δ): 1.35 (3H, t, J=7.5 Hz), 2.60 (3H, s), 2.67 (3H, s), 2.86 (2H, q), 3.67 (3H, s), 5.50 (2H, s), 6.92 (1H, s), 7.13–7.24 (3H, m), 7.50 (2H, d, J=9 Hz)

(2)
A mixture of 3-[4-(4-bromo-3-cyano-1-ethyl-2-pyrrolyl)benzyl]-5,7-dimethyl-2-ethyl-3H-imidazo[4,5-b]pyridine and 3-[4-(5-bromo-3-cyano-1-ethyl-2-pyrrolyl)benzyl]-5,7-dimethyl-2-ethyl-3H-imidazo[4,5-b]pyridine.

NMR (CDCl₃, δ): 1.12–1.32 (6H, m), 2.60 (3H, s), 2.65 (3H, s), 2.82 (2H, t, J=8 Hz), 3.82–4.05 (2H, m), 5.54 (2H, s), 6.50 (0.4H, s), 6.93 (0.6H, s), 7.18–7.42 (4H, m)

Preparation 138

The following compounds were obtained according to a similar manner to that of Preparation 105.

(1)

3-[4-(3-Cyano-1-propyl-2-pyrrolyl)benzyl]-7-methyl-2-propyl-3H-imidazo[4,5-b]pyridine NMR (CDCl₃, δ): 0.75 (3H, t, J=8 Hz), 1.00 (3H, t, J=8 Hz), 1.61 (2H, m), 1.81 (2H, m), 2.72 (3H, s), 2.88 (2H, t, J=8 Hz), 3.78 (2H, t, J=8 Hz), 5.55 (2H, s), 6.47 (1H, d, J=3 Hz), 6.69 (1H, d, J=3 Hz), 7.06 (1H, d, J=5 Hz), 7.23 (2H, d, J=9 Hz), 7.33 (2H, d, J=9 Hz), 8.24 (1H, d, J=5 Hz)

(2)

3-[4-(3-Cyano-1-ethyl-2-pyrrolyl)benzyl]-5,7-dimethyl-2-ethyl-3H-imidazo[4,5-b]pyridine mp: 171°-172° C.

NMR (CDCl₃, δ): 1.26 (3H, t, J=8 Hz), 1.36 (3H, t, J=8 Hz), 2.61 (3H, s), 2.66 (3H, s), 2.86 (2H, q, J=8 Hz), 3.87 (2H, q, J=8 Hz), 5.53 (2H, s), 6.49 (1H, d, J=3 Hz), 6.70 (1H, d, J=3 Hz), 6.95 (1H, s), 7.23 (2H, d, J=9 Hz), 7.35 (2H, d, J=9 Hz)

(3)

3-[4-(3-Cyano-1-isopropyl-2-pyrrolyl)benzyl]-7-methyl-2-propyl-3H-imidazo[4,5-b]pyridine NMR (CDCl₃, δ): 1.01 (3H, t, J=8 Hz), 1.33 (6H, d, J=7 Hz), 1.81 (2H, m), 2.70 (3H, s), 2.86 (2H, t, J=8 Hz), 4.31 (1H, m), 5.55 (2H, s), 6.50 (1H, d, J=3 Hz), 6.79 (1H, d, J=3 Hz), 7.05 (1H, d, J=5 Hz), 7.23 (2H, d, J=9 Hz), 7.32 (2H, d, J=9 Hz), 8.23 (1H, d, J=5 Hz)

Preparation 139

The following compound was obtained according to similar manners to those of Preparation 27 and 28, successively.

A mixture of 3-[4-(4-bromo-3-cyano-1-ethyl-2-pyrrolyl)benzyl]-5,7-dimethyl-2-propyl-3H-imidazo[4,5-b]pyridine and 3-[4-(5-bromo-3-cyano-1-ethyl-2-pyrrolyl)benzyl]-5,7-dimethyl-2-propyl-3H-imidazo[4,5-b]pyridine NMR (CDCl₃, δ): 0.96 (3H, t, J=8 Hz), 1.21 (3H, t, J=8 Hz), 1.76 (2H, m), 2.59 (3H, s), 2.63 (3H, s), 2.76 (2H, t, J=8 Hz), 3.85–4.05 (2H, m), 5.51 (2H, s), 6.91 (0.9H, s), 7.16–7.57 (4.1H, m)

Preparation 140

The following compound was obtained according to a similar manner to that of Preparation 105.

3-[4-(3-Cyano-1-ethyl-2-pyrrolyl)benzyl]-5,7-dimethyl-2-propyl-3H-imidazo[4,5-b]pyridine NMR (CDCl₃, δ): 0.97 (3H, t, J=8 Hz), 1.26 (3H, t, J=8 Hz), 1.76 (2H, m), 2.60 (3H, s), 2.64 (3H, s), 2.76 (2H, dd, J=7 Hz and 8 Hz), 3.88 (2H, q, J=8 Hz), 5.52 (2H, s), 6.49 (1H, d, J=3 Hz), 6.70 (1H, d, J=3 Hz), 6.90 (1H, s), 7.23 (2H, d, J=9 Hz), 7.84 (2H, d, J=9 Hz)

Preparation 141

A mixture of (4-methoxycarbonylbenzoyl)acetonitrile (80.0 g), 2-aminopropanone diethyl acetal (58.0 g) and toluene (370 ml) was refluxed for 15 hours under nitrogen atmosphere. The mixture was evaporated in vacuo. The residue was purified by silica gel column chromatography to afford a mixture of (E)-3-(2,2-diethoxy-1-methylethylamino)-3-(4-methoxycarbonylphenyl)acrylonitrile and (Z)-3-(2,2-diethoxy-1-methylethylamino)-3-4-methoxycarbonylphenyl)acrylonitrile as a brown oil (117.6 g).

NMR (CDCl₃, δ): 1.23 (6H, t, J=7.0 Hz), 1.27 (3H, d, 3.95 (3H, s), 4.03 (2/5H, s), 4.17 (3/5H, s), 4.36 (2/5H, d, J=3.5 Hz), 4.46 (3/5H, d, J=3.5 Hz), 4.69 (3/5H, d, J=8.0 Hz), 5.07 (2/5H, d, J=10.0 Hz), 7.50 (4/5H, d, J=8.0 Hz), 7.61 (6/5H, d, J=8.0 Hz), 8.08 (4/5H, d, J=8.0 Hz), 8.11 (6/5H, d, J=8.0 Hz)

Preparation 142

A mixture (117.0 g) of (E)-3-(2,2-diethoxy-1-methylethylamino-3-(4-methoxycarbonylphenyl)acrylonitrile and (Z)-3-(2,2-diethoxy-1-methylethylamino)-3-(4-methoxycarbonylphenyl)acrylonitrile was treated with trifluoroacetic acid (200 ml) at 0° C. for 30 minutes and then at ambient temperature for 30 minutes. To the mixture ethyl acetate (300 ml) was added at 0° C. and this mixture was stirred at 0° C. for 15 minutes. The precipitates were collected by vacuum filtration to afford 2-(4-methoxycarbonylphenyl)-5-methylpyrrole-3-carbonitrile as an orange powder (54.8 g).

mp: 201°-205° C.

NMR (CDCl₃, δ): 2.35 (3H, s), 3.96 (3H, s), 6.28 (1H, d, J=2.5 Hz), 7.74 (2H, d, J=9.0 Hz), 8.10 (2H, d, J=9.0 Hz), 8.60 (1H, br s)

Preparation 143

The following compounds were obtained according to a similar manner to that of Preparation 96.

(1)

2-(4-Methoxycarbonylphenyl)-1,5-dimethylpyrrole-3-carbonitrile mp: 138°-139.5° C.

NMR (CDCl₃, δ): 2.29 (3H, s), 3.51 (3H, s), 3.96 (3H, s), 6.27 (1H, s), 7.52 (2H, d, J=9.0 Hz), 8.16 (2H, d, J=9.0 Hz)

(2)

1-Ethyl-2-(4-methoxycarbonylphenyl)-5-methylpyrrole-3-carbonitrile mp: 84°-85.5° C.

NMR (CDCl₃, δ): 1.21 (3H, t, J=7.0 Hz), 2.31 (3H, s), 3.91 (2H, q, J=7.0 Hz), 3.97 (3H, s), 6.26 (1H, s), 7.51 (2H, d, J=9.0 Hz), 8.16 (2H, d, J=9.0 Hz)

(3)

5-Chloro-1-methyl-2-(4-methylphenyl)pyrrole-3-carbonitrile

NMR (CDCl₃, δ): 2.42 (3H, s), 3.54 (3H, s), 6.41 (1H, s), 7.32 (4H, s)

(4)

5-Chloro-1-ethyl-2-(4-methylphenyl)pyrrole-3-carbonitrile

NMR (CDCl₃, δ): 1.25 (3H, t, J=7 Hz), 2.41 (3H, s), 3.92 (2H, q, J=7 Hz), 6.49 (1H, s), 7.30 (4H, s)

Preparation 144

The following compound was obtained according to a similar manner to that of Preparation 1.

5-Chloro-2-(4-methylphenyl)pyrrole-3-carbonitrile

NMR (CDCl₃, δ): 2.39 (3H, s), 6.37 (1H, d, J=3 Hz), 7.27 (2H, d, J=9 Hz), 7.54 (2H, d, J=9 Hz), 8.64 (1H, br s)

Preparation 145

The following compounds were obtained according to a similar manner to that of Preparation 37.

(1)
2-(4-Hydroxymethylphenyl)-1,5-dimethylpyrrole-3-carbonitrile mp: 108°–111° C.

NMR (CDCl₃, δ): 1.96 (1H, bt, J=4.0 Hz), 2.28 (3H, s), 3.49 (3H, s), 4.75 (2H, d, J=4.0 Hz), 6.22 (1H, s), 7.41 (2H, d, J=9.0 Hz), 7.49 (2H, d, J=9.0 Hz)

(2)
1-Ethyl-2-(4-hydroxymethylphenyl)-5-methylpyrrole-3-carbonitrile mp: 91°–94.5° C.

NMR (CDCl₃, δ): 1.18 (3H, t, J=7.0 Hz), 2.19 (1H, br s), 2.29 (3H, s), 3.87 (2H, q, J=7.0 Hz), 4.73 (2H, s), 6.20 (1H, s), 7.40 (2H, d, J=9.0 Hz), 7.48 (2H, d, J=9.0 Hz)

Preparation 146

The following compounds were obtained according to a similar manner to that of Preparation 60.

(1)
2-(4-Methanesulfonyloxymethylphenyl)-1,5-dimethylpyrrole-3-carbonitrile mp: 89°–94° C.

NMR (CDCl₃, δ): 2.28 (3H, s), 3.01 (3H, s), 3.49 (3H, s), 5.29 (2H, s), 6.25 (1H, s), 7.47 (2H, d, J=9.0 Hz), 7.56 (2H, d, J=9.0 Hz)

(2)
1-Ethyl-2-(4-methanesulfonyloxymethylphenyl)-5-methylpyrrole-3-carbonitrile mp: 104.5°–108° C.

NMR (CDCl₃, δ): 1.20 (3H, t, J=7.0 Hz), 2.31 (3H, s), 3.01 (3H, s), 3.89 (2H, q, J=7.0 Hz), 5.29 (2H, s), 6.24 (1H, s), 7.47 (2H, d, J=9.0 Hz), 7.56 (2H, d, J=9.0 Hz)

Preparation 147

The following compounds were obtained according to a similar manner to that of Preparation 7.

(1)
2-(4-Bromomethylphenyl)-5-chloro-1-methylpyrrole-3-carbonitrile

NMR (CDCl₃, δ): 4.54 (2H, s), 6.45 (1H, s), 7.41 (2H, d, J=9 Hz), 7.53 (2H, d, J=9 Hz)

(2)
2-(4-Bromomethylphenyl)-5-chloro-1-ethylpyrrole-3-carbonitrile

NMR (CDCl₃, δ): 1.28 (3H, t, J=7 Hz), 3.97 (2H, q, J=7 Hz), 4.52 (2H, s), 6.42 (1H, s), 7.40 (2H, d, J=9 Hz), 7.52 (2H, d, J=9 Hz)

Preparation 148

The following compounds were obtained according to a similar manner to that of Preparation 9.

(1)
3-[4-(3-Cyano-5-chloro-1-ethyl-2-pyrrolyl)benzyl]-7-methyl-2-propyl-3H-imidazo[4,5-b]pyridine NMR (CDCl₃, δ): 1.00 (3H, t, J=7 Hz), 1.20 (3H, t, J=7 Hz), 1.81 (2H, m), 2.71 (3H, s), 2.82 (2H, t, J=7 Hz), 3.91 (2H, q, J=7 Hz), 5.54 (2H, s), 6.40 (1H, s), 7.04 (1H, d, J=5 Hz), 7.19 (2H, d, J=9 Hz), 7.33 (2H, d, J=9 Hz), 8.23 (1H, d, J=5 Hz)

(2)
3-[4-(3-Cyano-5-chloro-1-methyl-2-pyrrolyl)benzyl]-7-methyl-2-propyl-3H-imidazo[4,5-b]pyridine mp: 132°–134° C.

NMR (CDCl₃, δ): 1.01 (3H, t, J=7 Hz), 1.82 (2H, m), 2.70 (3H, s), 2.83 (2H, t, J=7 Hz), 3.50 (3H, s), 5.55 (2H, s), 6.41 (1H, s), 7.05 (1H, d, J=5 Hz), 7.24 (2H, d, J=9 Hz), 7.36 (2H, d, J=9 Hz), 8.21 (1H, d, J=5 Hz)

(3)
3-[4-(5-Chloro-3-cyano-1-ethyl-2-pyrrolyl)benzyl]-2-ethyl-5,7-dimethyl-3H-imidazo[4,5-b]pyridine NMR (CDCl₃, δ): 1.19 (3H, t, J=8 Hz), 1.32 (3H, t, J=8 Hz), 2.60 (3H, s), 2.65 (3H, s), 2.81 (2H, q, J=8 Hz), 3.90 (2H, q, J=8 Hz), 5.50 (2H, s), 6.40 (1H, s), 6.90 (1H, s), 7.19 (2H, d, J=9 Hz), 7.34 (2H, d, J=9 Hz)

(4)
3-[4-(5-Chloro-3-cyano-1-methyl-2-pyrrolyl)benzyl]-2-ethyl-5,7-dimethyl-3H-imidazo[4,5-b]pyridine NMR (CDCl₃, δ): 1.36 (3H, t, J=7 Hz), 2.60 (3H, s), 2.64 (3H, s), 2.82 (2H, q, J=7 Hz), 3.50 (3H, s), 5.51 (2H, s), 6.41 (1H, s), 6.92 (1H, s), 7.24 (2H, d, J=9 Hz), 7.36 (2H, d, J=9 Hz)

(5)
3-[4-(5-Chloro-3-cyano-1-ethyl-2-pyrrolyl)benzyl]-5,7-dimethyl-2-propyl-3H-imidazo[4,5-b]pyridine mp: 131°–135° C.

NMR (CDCl₃, δ): 0.96 (3H, t, J=7 Hz), 1.21 (3H, t, J=7 Hz), 1.76 (2H, m), 2.60 (3H, s), 2.64 (3H, s), 2.77 (2H, t, J=7 Hz), 3.91 (2H, q, J=7 Hz), 5.52 (2H, s), 6.40 (1H, s), 6.92 (1H, s), 7.25 (2H, d, J=9 Hz), 7.34 (2H, d, J=9 Hz)

(6)
3-[4-(5-Chloro-3-cyano-1-methyl-2-pyrrolyl)benzyl]-5,7-dimethyl-2-propyl-3H-imidazo[4,5-b]pyridine NMR (CDCl₃, δ): 0.98 (3H, t, J=7 Hz), 1.78 (2H, m), 2.60 (3H, s), 2.63 (3H, s), 2.76 (2H, t, J=7 Hz), 3.50 (3H, s), 5.51 (2H, s), 6.40 (1H, s), 6.91 (1H, s), 7.22 (2H, d, J=9 Hz), 7.34 (2H, d, J=9 Hz)

(7)
3-[4-(3-Cyano-1,5-dimethyl-2-pyrrolyl)benzyl]-2-ethyl-5,7-dimethyl-3H-imidazo[4,5-b]pyridine mp: 156°–157° C.

NMR (CDCl₃, δ): 1.34 (3H, t, J=7.5 Hz), 2.25 (3H, s), 2.60 (3H, s), 2.65 (3H, s), 2.82 (2H, q, J=7.5 Hz), 3.42 (3H, s), 5.51 (2H, s), 6.21 (1H, s), 6.91 (1H, s), 7.22 (2H, d, J=9.0 Hz), 7.35 (2H, d, J=9.0 Hz)

(8)
3-[4-(3-Cyano-1-ethyl-5-methyl-2-pyrrolyl)benzyl]-2-ethyl-5,7-dimethyl-3H-imidazo[4,5-b]pyridine mp: 159°–162° C.

NMR (CDCl₃, δ): 1.15 (3H, t, J=7.0 Hz), 1.32 (3H, t, J=7.5 Hz), 2.28 (3H, s), 2.61 (3H, s), 2.66 (3H, s), 2.84 (2H, q, J=7.5 Hz), 3.81 (2H, q, J=7.0 Hz), 5.51 (2H, s), 6.20 (1H, s), 6.91 (1H, s), 7.21 (2H, d, J=9.0 Hz), 7.35 (2H, d, J=9.0 Hz)

(9)
3-[4-(3-Cyano-1,5-dimethyl-2-pyrrolyl)benzyl]-7-methyl-2-propyl-3H-imidazo[4,5-b]pyridine mp: 111°–113° C.

NMR (CDCl₃, δ): 1.01 (3H, t, J=7.5 Hz), 1.71–1.92 (2H, m), 2.24 (3H, s), 2.70 (3H, s), 2.84 (2H, t, J=7.5 Hz), 3.42 (3H, s), 5.54 (2H, s), 6.21 (1H, s), 7.03 (1H, d, J=5.0 Hz), 7.22 (2H, d, J=9.0 Hz), 7.37 (2H, d, J=9.0 Hz), 8.21 (1H, d, J=5.0 Hz)

(10)
3-[4-(3-Cyano-1-ethyl-5-methyl-2-pyrrolyl)benzyl]-7-methyl-2-propyl-3H-imidazo[4,5-b]pyridine mp: 113°–115° C.

NMR (CDCl₃, δ): 1.00 (3H, t, J=7.5 Hz), 1.15 (3H, t, J=7.0 Hz), 1.70–1.91 (2H, m), 2.28 (3H, s), 2.70 (3H, s), 2.83 (2H, t, J=7.5 Hz), 3.82 (2H, q, J=7.0 Hz), 5.54 (2H, s), 6.20 (1H, s), 7.05 (1H, d, J=5.0 Hz), 7.21 (2H, d, J=9.0 Hz), 7.35 (2H, d, J=9.0 Hz), 8.21 (1H, d, J=5.0 Hz)

(11)
3-[4-(3-Cyano-1,5-dimethyl-2-pyrrolyl)benzyl]-5,7-dimethyl-2-propyl-3H-imidazo[4,5-b]pyridine mp: 118°–120° C.

NMR (CDCl₃, δ): 0.98 (3H, t, J=7.5 Hz), 1.67–1.89 (2H, m), 2.25 (3H, s), 2.60 (3H, s), 2.63 (3H, s), 2.78 (2H, t, J=7.5 Hz), 3.42 (3H, s), 5.51 (2H, s), 6.21 (1H, s), 6.91 (1H, s), 7.21 (2H, d, J=9 Hz), 7.35 (2H, d, J=7.5 Hz)

(12)
3-[4-(3-Cyano-1-ethyl-5-methyl-2-pyrrolyl)benzyl]5,7-dimethyl-2-propyl-3H-imidazo[4,5-b]pyridine mp: 169°–170° C.

NMR (CDCl₃, δ): 0.98 (3H, t, J=7 Hz), 1.14 (3H, t, J=7 Hz), 1.77 (2H, m), 2.27 (3H, s), 2.61 (3H, s), 2.65 (3H, s), 2.78 (2H, t, J=7 Hz), 3.81 (2H, q, J=7 Hz), 5.52 (2H, s), 6.20 (1H, s), 6.91 (1H, s), 7.21 (2H, d, J=9 Hz), 7.35 (2H, d, J=9 Hz)

(13)
3-[4-(2-Bromo-4-cyano-1-methyl-3-pyrrolyl)benzyl]-2-ethyl-5,7-dimethyl-3H-imidazo[4,5-b]pyridine mp: 151°–152° C.

NMR (CDCl₃, δ): 1.33 (3H, t, J=7.5 Hz), 2.60 (3H, s), 2.64 (3H, s), 2.82 (2H, q, J=7.5 Hz), 3.69 (3H, s), 5.50 (2H, s), 6.90 (1H, s), 7.19 (2H, d, J=9 Hz), 7.30 (1H, s), 7.48 (2H, d, J=9 Hz)

(14)
3-[4-(2-Bromo-4-cyano-1-methyl-3-pyrrolyl)benzyl]-5,7-dimethyl-2-propyl-3H-imidazo[4,5-b]pyridine mp: 142°–143° C.

NMR (CDCl₃, δ): 0.98 (3H, t, J=7.5 Hz), 1.65–1.87 (2H, m), 2.60 (3H, s), 2.64 (3H, s), 2.78 (2H, t, J=7.5 Hz), 3.69 (3H, s), 5.50 (2H, s), 6.90 (1H, s), 7.17 (2H, d, J=9 Hz), 7.30 (1H, s), 7.48 (2H, d, J=9 Hz)

EXAMPLE 1

A mixture of 2-butyl-3-[4-(3,4-dichloro-2-cyano-1-pyrrolyl)benzyl]-7-methyl-3H-imidazo[4,5-b]pyridine (490 mg) and trimethyltin azide (690 mg) in xylene (5 ml) was stirred at 120° C. for 22 hours. After cooled to ambient temperature, the mixture was treated with aqueous 1N sodium hydroxide (10 ml) for 4 hours. The suspension was filtered. The filtrate was washed with diisopropyl ether, adjusted to pH 4 with aqueous 1N-hydrochloric acid, and concentrated in vacuo. The residue was purified by column chromatography on silica gel (elution by methanol/dichloromethane=1/8) to give 2-butyl-3-[4-[3,4-dichloro-2-(1H-tetrazol-5-yl)-1-pyrrolyl]benzyl]-7-methyl-3H-imidazo[4,5-b]pyridine (516 mg) as an amorphous solid.

NMR (DMSO-d₃, δ): 0.83 (3H, t, J=7.5 Hz), 1.22–1.44 (2H, m), 1.57–1.74 (2H, m), 2.58 (3H, s), 2.85 (2H, t, J=7.5 Hz), 5.58 (2H, s), 6.81 (1H, s), 7.10 (1H, d, J=4.5 Hz), 7.20 (2H, d, J=8.5 Hz), 7.28 (2H, d, J=8.5 Hz), 8.18 (1H, d, J=4.5 Hz)

Example 2

The following compounds were obtained according to a similar manner to that of Example 1.

(1)
3-[4-[4-Bromo-2-(1H-tetrazol-5-yl)-1-pyrrolyl]benzyl]-2-butyl-7-methyl-3H-imidazo[4,5-b]pyridine mp: 188°–191° C.

NMR (DMSO-d₆, δ): 0.88 (3H, t, J=7.5 Hz), 1.37 (2H, m), 1.68 (2H, m), 2.57 (3H, s), 5.55 (2H, s), 6.87 (1H, d, J=2.3 Hz), 7.09 (1H, d, J=5 Hz), 7.19 (4H, m), 7.40 (1H, d, J=2.3 Hz), 8.17 (1H, d, J=5 Hz)

(2)
2-Butyl-3-[4-[2-chloro-5-(1H-tetrazol-5-yl)-1-pyrrolyl]benzyl]-3H-imidazo[4,5-b]pyridine mp: 147° C.

NMR (DMSO-d₆, δ): 0.82 (3H, t, J=7.5 Hz), 1.22–1.45 (2H, m), 1.58–1.77 (2H, m), 2.86 (2H, t, J=7.5 Hz), 5.60 (2H, s), 6.41 (1H, d, J=4.5 Hz), 6.74 (1H, d, J=4.5 Hz), 7.21 (4H, s), 7.28 (1H, dd, J=8.0 Hz and 5.0 Hz), 8.03 (1H, dd, J=8.0 Hz and 1.0 Hz), 8.33 (1H, dd, J=5.0 Hz and 1.0 Hz)

(3)
2-Butyl-3-[4-[4-nitro-2-(1H-tetrazol-5-yl)-1-pyrrolyl]benzyl]-3H-imidazo[4,5-b]pyridine NMR (DMSO-d₆, δ): 0.88 (3H, t, J=7.5 Hz), 1.27–1.49 (2H, m), 1.64–1.83 (2H, m), 2.89 (2H, t, J=7.5 Hz), 5.56 (2H, s), 7.03 (1H, d, J=1.5 Hz), 7.19 (2H, d, J=8.0 Hz), 7.27 (1H, dd, J=7.5 Hz and 5.0 Hz), 7.29 (2H, d, J=8.0 Hz), 8.01 (1H, dd, J=7.5 Hz & 1.0 Hz), 8.19 (1H, d, J=1.5 Hz), 8.31 (1H, dd, J=5.0 Hz and 1.0 Hz)

(4)
2-Butyl-3-[4-[2-(1H-tetrazol-5-yl)-1-pyrrolyl]benzyl]-3H-imidazo[4,5-b]pyridine mp: 98°–101° C.

NMR (CD₃OD, δ): 0.93 (3H, t, J=7.5 Hz), 1.44 (2H, m), 1.80 (2H, m), 2.90 (2H, dd, J=7 Hz & 7 Hz), 5.57 (2H, s), 6.42 (1H, dd, J=3.5 Hz & 3 Hz), 6.94 (1H, dd, J=3.5 Hz & 2 Hz), 7.04 (1H, dd, J=3 Hz & 2 Hz), 7.21 (4H, s), 7.32 (1H, dd, J=8 Hz & 5 Hz), 8.04 (1H, dd, J=8 Hz & 1 Hz), 8.35 (1H, dd, J=5 Hz & 1 Hz)

(5)
2-Butyl-3-[4-[2-(1H-tetrazol-5-yl)-1-indolyl]benzyl]-3H-imidazo[4,5-b]pyridine (6)
2-Butyl-3-[4-[2-chloro-5-(1H-tetrazol-5-yl)-1-pyrrolyl]benzyl]-7-methyl-3H-imidazo[4,5-b]pyridine

EXAMPLE 3

To a solution of 2-butyl-3-[4-[3,4-dichloro-2-(1H-tetrazol-5-yl)-1-pyrrolyl]benzyl]-7-methyl-3H-imidazo[4,5-b]pyridine (496 mg) in hot ethanol (7.5 ml) was added a solution of sodium bicarbonate (86.6 mg) in water (4 ml) in one portion. The mixture was stirred at 80° C. for 5 minutes and concentrated in vacuo. The residue was dissolved in ethanol (6 ml). The ethanolic solution was filtered through a millipor filter. The filtrate was evaporated under reduced pressure. The residue was dissolved in water (5 ml) and lyophilized to yield sodium salt of 2-butyl-3-[4-[3,4-dichloro-2-(1H-tetrazol-5-yl)-1-pyrrolyl]benzyl]-7-methyl-3H-imidazo[4,5-b]pyridine (466 mg) as a solid.

NMR (D$_2$O, δ): 0.43 (3H, t, J=7.5 Hz), 0.80-1.01 (2H, m), 1.14-1.34 (2H, m), 2.31 (3H, s), 2.61 (2H, t, J=7.5 Hz), 5.31 (2H, s), 6.54 (1H, s), 6.69 (2H, d, J=8.5 Hz), 6.79 (1H, d, J=5.0 Hz), 6.90 (2H, d, J=8.5 Hz), 7.90 (1H, d, J=5.0 Hz)

EXAMPLE 4

The following compounds were obtained according to a similar manner to that of Example 3.

(1) Sodium salt of 3-[4-[4-bromo-2-(1H-tetrazol-5-yl)-1-pyrrolyl]benzyl]-2-butyl-7-methyl-3H-imidazo[4,5-b]pyridine mp: 154°-168° C.

NMR (D$_2$O, δ): 0.51 (3H, t, J=7.5 Hz), 0.87-1.08 (2H, m), 1.15-1.36 (2H, m), 2.30 (3H, s), 2.55 (2H, t, J=7.5 Hz), 5.18 (2H, s), 6.26 (1H, d, J=1.5 Hz), 6.48 (1H, d, J=1.5 Hz), 6.51 (2H, d, J=8.0 Hz), 6.69 (2H, d, J=8.0 Hz), 6.71 (1H, d, J=5.0 Hz), 7.78 (1H, d, J=5.0 Hz)

(2) Sodium salt of 2-butyl-3-[4-[2-chloro-5-(1H-tetrazol-5-yl)-1-pyrrolyl]benzyl]-3H-imidazo[4,5-b]pyridine NMR (D$_2$O, δ): 0.60 (3H, t, J=7 Hz), 1.08 (2H, m), 1.40 (2H, m), 2.70 (2H, t, J=7 Hz), 5.42 (2H, s), 6.19 (1H, d, J=4 Hz), 6.63 (1H, d, J=4 Hz), 6.90 (2H, d, J=9 Hz), 7.00 (2H, d, J=9 Hz), 7.20 (1H, dd, J=9 Hz & 6 Hz), 7.90 (1H, dd, J=9 Hz & 1 Hz), 8.17 (1H, dd, J=6 Hz & 1 Hz)

(3) Sodium salt of 2-butyl-3-[4-[4-nitro-2-(1H-tetrazol-5-yl)-1-pyrrolyl]benzyl]-3H-imidazo[4,5-b]pyridine mp: 166°-179° C.

NMR (D$_2$O, δ): 0.71 (3H, t, J=7.5 Hz), 1.05-1.27 (2H, m), 1.41-1.61 (2H, m), 2.70 (2H, t, J=7.5 Hz), 5.42 (2H, s), 6.83 (2H, d, J=9.0 Hz), 6.94 (2H, d, J=9.0 Hz), 7.12 (1H, d, J=1.5 Hz), 7.21 (1H, dd, J=8 Hz & 5 Hz), 7.64 (1H, d, J=1.5 Hz), 7.92 (1H, dd, J=8.0 Hz & 1.0 Hz), 8.12 (1H, dd, J=5.0 Hz & 1.0 Hz)

(4) Sodium salt of 2-butyl-3-[4-[2-(1H-tetrazol-5-yl)-1-indolyl]benzyl]-3H-imidazo[4,5-b]pyridine mp: 187°-192° C. (dec.)

NMR (D$_2$O+CD$_3$OD, δ): 0.50 (3H, t, J=7.5 Hz), 0.92 (2H, m), 1.28 (2H, m), 2.50 (2H, t, J=7.5 Hz), 5.26 (2H, s), 6.50-6.82 (3H, m), 6.63 (2H, d, J=8 Hz), 6.80 (2H, d, J=8 Hz), 6.98 (1H, s), 7.12 (1H, dd, J=8 Hz & 5 Hz), 7.37 (1H, d, J=8 Hz), 7.86 (1H, d, J=8 Hz), 8.08 (1H, d, J=5 Hz)

(5) Sodium salt of 2-butyl-3-[4-[2-chloro-5-(1H-tetrazol-5-yl)-1-pyrrolyl]benzyl]-7-methyl-3H-imidazo[4,5-b]pyridine mp: 154°-157° C.

NMR (D$_2$O, δ): 0.72 (3H, t, J=7.5 Hz), 1.21 (2H, m), 1.49 (2H, m), 2.60 (3H, s), 2.87 (2H, t, J=6 Hz), 5.54 (2H, s), 6.25 (1H, d, J=4 Hz), 6.84 (1H, d, J=4 Hz), 6.90 (2H, d, J=9 Hz), 7.05 (1H, d, J=5 Hz), 7.14 (2H, d, J=9 Hz), 8.15 (1H, d, J=5 Hz)

EXAMPLE 5

The following compounds were obtained according to a similar manner to that of Example 1.

(1) 3-[4-[2-Bromo-5-(1H-tetrazol-5-yl)-1-pyrrolyl]benzyl]-2-butyl-7-methyl-3H-imidazo[4,5-b]pyridine NMR (CDCl$_3$, δ): 0.90 (3H, t, J=7.5 Hz), 1.40 (2H, m), 1.70 (2H, m), 3.41 (2H, m), 5.62 (2H, s), 6.47 (1H, d, J=4 Hz), 6.90 (1H, d, J=4 Hz), 7.15 (1H, d, J=5 Hz), 7.23 (4H, s), 8.20 (1H, d, J=5 Hz)

(2) 3-[4-[4-Bromo-2-(1H-tetrazol-5-yl)-1-pyrrolyl]-2-fluorobenzyl]-2-butyl-7-methyl-3H-imidazo[4,5-b]pyridine NMR (DMSO-d$_6$, δ): 0.89 (3H, t, J=7.5 Hz), 1.27-1.49 (2H, m), 1.62-1.82 (2H, m), 2.57 (3H, s), 2.86 (2H, t, J=7.5 Hz), 5.57 (2H, s), 6.85 (1H, d, J=1.0 Hz), 6.92 (1H, d, J=9 Hz), 7.03 (1H, dd, J=9.0 Hz & 1.5 Hz), 7.09 (1H, d, J=5.0 Hz), 7.33 (1H, dd, J=11.0 Hz & 1.5 Hz), 7.45 (1H, d, J=1.0 Hz), 8.14 (1H, d, J=5.0 Hz)

(3) 3-[4-[4-Bromo-2-(1H-tetrazol-5-yl)-1-pyrrolyl]-benzyl]-7-methyl-2-propyl-3H-imidazo[4,5-b]pyridine mp: 179°-186° C.

NMR (DMSO-d$_6$, δ): 0.94 (3H, t, J=7.5 Hz), 1.62-1.86 (2H, m), 2.58 (3H, s), 2.82 (2H, t, J=7.5 Hz), 5.53 (2H, s), 6.81 (1H, d, J=1.0 Hz), 7.09 (1H, d, J=5 Hz), 7.16 (2H, d, J=9.0 Hz), 7.22 (2H, d, J=9.0 Hz), 7.39 (1H, d, J=1.0 Hz), 8.16 (1H, d, J=5.0 Hz)

(4) 2-Butyl-7-methyl-3-[2-[2-(1H-tetrazol-5-yl)-1-pyrrolyl]-5-pyridylmethyl]-3H-imidazo[4,5-b]pyridine mp: 148°-154° C.

NMR (DMSO-d$_6$, δ): 0.89 (3H, t, J=7.5 Hz), 1.28-1.49 (2H, m), 1.61-1.81 (2H, m), 2.56 (3H, s), 2.90 (2H, t, J=7.5 Hz), 5.57 (2H, s), 6.46 (1H, t, J=4.0 Hz), 6.86 (1H, dd, J=4.0 Hz & 1.0 Hz), 7.11 (1H, d, J=5.0 Hz), 7.38 (1H, d, J=8.5 Hz), 7.50 (1H, dd, J=4.0 Hz & 1.0 Hz), 7.69 (1H, dd, J=8.5 Hz & 1.5 Hz), 8.17 (1H, d, J=5.0 Hz), 8.31 (1H, d, J=1.5 Hz)

(5) 3-[2-[2-Bromo-5-(1H-tetrazol-5-yl)-1-pyrrolyl]-5-pyridylmethyl]-2-butyl-7-methyl-3H-imidazo[4,5-b]pyridine mp: 98°-114° C.

NMR (DMSO-d$_6$, δ): 0.87 (3H, t, J=7.5 Hz), 1.25-1.48 (2H, m), 1.59-1.78 (2H, m), 2.57 (3H, s), 2.90 (2H, t, J=7.5 Hz), 5.69 (2H, s), 6.58 (1H, d, J=4.5 Hz), 6.96 (1H, d, J=4.5 Hz), 7.11 (1H, d, J=5.0 Hz), 7.48 (1H, d, J=7.5 Hz), 7.73 (1H, dd, J=7.5 Hz & 1.5 Hz), 8.20 (1H, d, J=5.0 Hz), 8.48 (1H, d, J=1.5 Hz)

(6) 3-[3-Bromo-4-[2-(1H-tetrazol-5-yl)-1-pyrrolyl]benzyl]-2-butyl-7-methyl-3H-imidazo[4,5-b]pyridine NMR (DMSO-d$_6$, δ): 0.89 (3H, t, J=7.5 Hz), 1.29-1.50 (2H, m), 1.62-1.80 (2H, m), 2.58 (3H, s), 2.89 (2H, t, J=7.5 Hz), 5.61 (2H, s), 6.43 (1H, t, J=4.0 Hz), 6.97 (1H, dd, J=4.0 Hz & 1.0 Hz), 7.05-7.15 (1H, m), 7.11 (1H, d, J=5.0 Hz), 7.16 (1H, dd, J=8.5 Hz & 1.0 Hz), 7.43 (1H, d, J=8.5 Hz), 7.64 (1H, d, J=1.0 Hz), 8.20 (1H, d, J=5.0 Hz)

(7)

3-[3-Bromo-4-[4-bromo-2-(1H-tetrazol-5-yl)-1-pyrrolyl]benzyl]-2-butyl-7-methyl-3H-imidazo[4,5-b]pyridine NMR (DMSO-d$_6$, δ): 0.89 (3H, t, J=7.5 Hz), 1.28-1.50 (2H, m), 1.62-1.80 (2H, m), 2.58 (3H, s), 2.88 (2H, t, J=7.5 Hz), 5.61 (2H, s), 6.93 (1H, d, J=1.5 Hz), 7.11 (1H, d, J=5.0 Hz), 7.15 (1H, dd, J=8.5 Hz & 1.0 Hz), 7.31 (1H, d, J=1.5 Hz), 7.45 (1H, d, J=8.5 Hz), 7.63 (1H, d, J=1.0 Hz), 8.19 (1H, d, J=5.0 Hz)

(8)

3-[4-[2-Bromo-5-(1H-tetrazol-5-yl)-1-pyrrolyl]-3-chlorobenzyl]-2-butyl-7-methyl-3H-imidazo[4,5-b]pyridine NMR (CDCl$_3$-CD$_3$OD, δ): 0.93 (3H, t, J=7.5 Hz), 1.44 (2H, m), 1.74 (2H, m), 2.73 (3H, s), 3.05 (2H, dd, J=8 Hz & 7 Hz), 5.72 (2H, s), 6.53 (1H, d, J=4 Hz), 6.98 (1H, d, J=4 Hz), 7.32-7.34 (2H, m), 7.37-7.45 (2H, m), 8.37 (1H, d, J=5 Hz)

(9)

3-[4-[4-Bromo-2-(1H-tetrazol-5-yl)-1-pyrrolyl]-3-chlorobenzyl]-2-butyl-7-methyl-3H-imidazo[4,5-b]pyridine NMR (CDCl$_3$+CD$_3$OD, δ): 0.95 (3H, t, J=7.5 Hz), 1.45 (2H, m), 1.77 (2H, m), 2.70 (3H, s), 2.94 (2H, t, J=7.5 Hz), 5.59 (2H, s), 6.93 (1H, d, J=1.9 Hz), 6.95 (1H, d, J=1.9 Hz), 7.13 (1H, d, J=5 Hz), 7.15 (1H, d, J=8.1 Hz, 1.9 Hz), 7.29 (1H, d, J=1.9 Hz), 7.38 (1H, d, J=8.1 Hz), 8.20 (1H, d, J=5 Hz)

(10)

3-[4-[4-Bromo-2-(1H-tetrazol-5-yl)-1-pyrrolyl]-2-chlorobenzyl]-2-butyl-7-methyl-3H-imidazo[4,5-b]pyridine NMR (CDCl$_3$-CD$_3$OD, δ): 0.94 (3H, t, J=7.5 Hz), 1.44 (2H, m), 1.75 (2H, m), 2.70 (3H, s), 2.88 (2H, t, J=8 Hz), 5.65 (2H, s), 6.58 (1H, d, J=8 Hz), 6.92 (1H, d, J=2 Hz), 7.02 (1H, dd, J=8 Hz & 2 Hz), 7.09 (1H, d, J=2 Hz), 7.14 (1H, d, J=5 Hz), 7.47 (1H, d, J=2 Hz), 8.18 (1H, d, J=5 Hz)

(11)

3-[4-[2-Bromo-5-(1H-tetrazol-5-yl)-1-pyrrolyl]benzyl]-7-methyl-2-propyl-3H-imidazo[4,5-b]pyridine NMR (CDCl$_3$-CD$_3$OD, δ): 0.96 (3H, t, J=7.5 Hz), 1.74 (2H, m), 2.69 (3H, s), 2.86 (2H, t, J=8 Hz), 5.60 (2H, s), 6.45 (1H, d, J=4 Hz), 6.86 (1H, d, J=4 Hz), 7.13 (1H, d, J=5 Hz), 7.22 (4H, s), 8.20 (1H, d, J=5 Hz)

(12)

2-Butyl-7-methyl-3-[3-nitro-4-[2-(1H-tetrazol-5-yl)-1-pyrrolyl]benzyl]-3H-imidazo[4,5-b]pyridine NMR (DMSO-d$_6$, δ): 0.88 (3H, t, J=7 Hz), 1.39 (2H, m), 1.73 (2H, m), 2.92 (2H, t, J=7 Hz), 5.72 (2H, s), 6.45 (1H, t, J=3 Hz), 6.96 (1H, dd, J=3 Hz & 1 Hz), 7.12 (1H, d, J=4 Hz), 7.19 (1H, d, J=1 Hz), 7.48 (1H, dd, J=7 Hz & 1 Hz), 7.57 (1H, d, J=7 Hz), 8.10 (1H, d, J=1 Hz), 8.19 (1H, d, J=4 Hz)

(13)

2-Butyl-3-[3-chloro-4-[2-(1H-tetrazol-5-yl)-1-pyrrolyl]benzyl]-7-methyl-3H-imidazo[4,5-b]pyridine NMR (CDCl$_3$-CD$_3$OD, δ): 0.90 (3H, t, J=7.5 Hz), 1.40 (2H, m), 1.70 (2H, m), 2.64 (3H, s), 2.87 (2H, t, J=8 Hz), 5.54 (2H, s), 6.40 (1H, dd, J=4 Hz & 3 Hz), 6.85 (1H, dd, J=3 Hz & 1 Hz), 6.90 (1H, dd, J=4 Hz & 1 Hz), 7.09 (1H, d, J=5 Hz), 7.10 (1H, dd, J=8 Hz & 2 Hz), 7.23 (1H, d, J=2 Hz), 7.32 (1H, d, J=8 Hz), 8.14 (1H, d, J=5 Hz)

EXAMPLE 6

The following compounds were obtained according to a similar manner to that of Example 3.

(1) Sodium salt of 3-[4-[2-bromo-5-(1H-tetrazol-5-yl)-1-pyrrolyl]benzyl]-2-butyl-7-methyl-3H-imidazo[4,5-b]pyridine NMR (D$_2$O, δ): 0.58 (3H, t, J=7.5 Hz), 1.06 (2H, m), 1.31 (2H, m), 2.44 (3H, s), 2.71 (2H, t, J=6 Hz), 5.38 (2H, s), 6.26 (1H, d, J=4 Hz), 6.66 (1H, d, J=4 Hz), 7.35 (2H, d, J=8 Hz), 7.43 (1H, d, J=5 Hz), 7.46 (2H, d, J=8 Hz), 7.97 (1H, d, J=5 Hz)

(2) Sodium salt of 3-[4-[4-bromo-2-(1H-tetrazol-5-yl)-1-pyrrolyl]-2-fluorobenzyl]-2-butyl-7-methyl-3H-imidazo[4,5-b]pyridine mp: 153°-179° C.

NMR (D$_2$O, δ): 0.58 (3H, t, J=7.5 Hz), 0.95-1.17 (2H, m), 1.25-1.46 (2H, m), 2.35 (3H, s), 2.63 (2H, t, J=7.5 Hz), 5.27 (2H, s), 6.29-6.43 (1H, m), 6.37 (1H, d, J=1.0 Hz), 6.49-6.63 (2H, m), 6.53 (1H, d, J=1.0 Hz), 6.73 (1H, d, J=5.0 Hz), 7.83 (1H, d, J=5.0 Hz)

(3) Sodium salt of 3-[4-[4-bromo-2-(1H-tetrazol-5-yl)-1-pyrrolyl]benzyl]-7-methyl-2-propyl-3H-imidazo[4,5-b]pyridine mp: 157°-178° C.

NMR (D$_2$O, δ): 0.78 (3H, t, J=7.5 Hz), 1.40-1.62 (2H, m), 2.47 (3H, s), 2.70 (2H, t, J=7.5 Hz), 5.35 (2H, s), 6.52 (1H, d, J=1.0 Hz), 6.64 (2H, d, J=9.0 Hz), 6.65 (1H, d, J=1.0 Hz), 6.82 (2H, d, J=9.0 Hz), 6.93 (1H, d, J=5.0 Hz), 7.93 (1H, d, J=5.0 Hz)

(4) Sodium salt of 2-butyl-7-methyl-3-[2-[2-(1H-tetrazol-5-yl)-1-pyrrolyl]-5-pyridylmethyl]-3H-imidazo[4,5-b]pyridine mp: 123°-148° C.

NMR (D$_2$O, δ): 0.74 (3H, t, J=7.5 Hz), 1.12-1.33 (2H, m), 1.39-1.59 (2H, m), 2.50 (3H, s), 2.82 (2H, t, J=7.5 Hz), 5.42 (2H, s), 6.40 (1H, t, J=3.5 Hz), 6.65 (1H, d, J=8.0 Hz), 6.73 (1H, dd, J=3.5 Hz & 1.0 Hz), 6.98 (1H, d, J=5.0 Hz), 7.10 (1H, dd, J=3.5 Hz, 1.0 Hz), 7.28 (1H, dd, J=8.0 Hz & 1.5 Hz), 7.97 (1H, d, J=5.0 Hz), 8.17 (1H, d, J=1.5 Hz)

(5) Sodium salt of 3-[2-[2-bromo-5-(1H-tetrazol-5-yl)-1-pyrrolyl]-5-pyridylmethyl]-2-butyl-7-methyl-3H-imidazo[4,5-b]pyridine mp: 132°-157° C.

NMR (D$_2$O, δ): 0.68 (3H, t, J=7.5 Hz), 1.06-1.28 (2H, m), 1.33-1.52 (2H, m), 2.50 (3H, s), 2.84 (2H, t, J=7.5 Hz), 5.56 (2H, s), 6.41 (1H, d, J=4.5 Hz), 6.73 (1H, d, J=4.5 Hz), 7.03 (1H, d, J=5.0 Hz), 7.09 (1H, d, J=9 Hz), 7.52 (1H, dd, J=9.0 Hz & 1.5 Hz), 8.04 (1H, d, J=5.0 Hz), 8.31 (1H, d, J=1.5 Hz)

(6) Sodium salt of 3-[3-bromo-4-[2-(1H-tetrazol-5-yl)-1-pyrrolyl]benzyl]-2-butyl-7-methyl-3H-imidazo[4,5-b]pyridine mp: 128.5°-159.5° C.

NMR (D₂O, δ): 0.63 (3H, t, J=7.5 Hz), 1.01-1.24 (2H, m), 1.31-1.53 (2H, m), 2.43 (3H, s), 2.74 (2H, t, J=7.5 Hz), 5.38 (2H, s), 6.28 (1H, t, J=3.0 Hz), 6.55 (1H, br s), 6.71-6.81 (1H, m), 6.90 (1H, d, J=5.0 Hz), 7.00 (1H, d, J=8.0 Hz), 7.09 (1H, d, J=8.0 Hz), 7.21 (1H, s), 7.95 (1H, d, J=5.0 Hz)

(7) Sodium salt of 3-[3-bromo-4-[4-bromo-2-(1H-tetrazol-5-yl)-1-pyrrolyl]benzyl]-2-butyl-7-methyl-3H-imidazo[4,5-b]pyridine mp: 159.5°-170.5° C.

NMR (D₂O, δ): 0.52 (3H, t, J=7.5 Hz), 0.92-1.18 (2H, m), 1.27-1.50 (2H, m), 2.36 (3H, s), 2.69 (2H, t, J=7.5 Hz), 5.35 (2H, s), 6.30 (1H, d, J=1.0 Hz), 6.66 (1H, d, J=1.0 Hz), 6.79 (1H, d, J=5.0 Hz), 6.98 (2H, s), 7.17 (1H, s), 7.89 (1H, d, J=5.0 Hz)

(8) Sodium salt of 3-[4-[2-bromo-5-(1H-tetrazol-5-yl)-1-pyrrolyl]-3-chlorobenzyl]-2-butyl-7-methyl-3H-imidazo[4,5-b]pyridine mp: 165°-175° C.

NMR (D₂O, δ): 0.47 (3H, t, J=7 Hz), 0.98 (2H, m), 1.27 (2H, m), 2.69 (2H, t, J=8 Hz), 5.36 (2H, br s), 6.20 (1H, d, J=4 Hz), 6.72 (1H, d, J=4 Hz), 6.82 (1H, d, J=5 Hz), 6.94 (1H, dd, J=8 Hz & 1 Hz), 6.99 (1H, d, J=8 Hz), 7.10 (1H, s), 7.94 (1H, d, J=5 Hz)

(9) Sodium salt of 3-[4-[4-bromo-2-(1H-tetrazol-5-yl)-1-pyrrolyl]-3-chlorobenzyl]-2-butyl-7-methyl-3H-imidazo[4,5-b]pyridine mp: 168°-178° C.

NMR (D₂O, δ): 0.61 (3H, t, J=7.5 Hz), 1.13 (2H, m), 1.42 (2H, m), 2.43 (3H, s), 2.73 (2H, t, J=8 Hz), 5.49 (2H, s), 6.43 (1H, d, J=1 Hz), 6.68 (1H, d, J=1 Hz), 6.90 (1H, d, J=5 Hz), 6.91-7.08 (3H, m), 7.94 (1H, d, J=5 Hz)

(10) Sodium salt of 3-[4-[4-bromo-2-(1H-tetrazol-5-yl)-1-pyrrolyl]-2-chlorobenzyl]-2-butyl-7-methyl-3H-imidazo[4,5-b]pyridine NMR (D₂O, δ): 0.60 (3H, t, J=7.5 Hz), 1.07 (2H, m), 1.37 (2H, m), 2.39 (3H, s), 2.60 (2H, t, J=8 Hz), 5.30 (2H, br s), 6.20 (1H, d, J=9 Hz), 6.42 (1H, dd, J=9 Hz & 1 Hz), 6.45 (1H, d, J=1 Hz), 6.55 (1H, d, J=1 Hz), 6.84 (1H, d, J=5 Hz), 6.95 (1H, d, J=1 Hz), 7.86 (1H, d, J=5 Hz)

(11) Sodium salt of 3-[4-[2-bromo-5-(1H-tetrazol-5-yl)-1-pyrrolyl]benzyl]-7-methyl-2-propyl-3H-imidazo[4,5-b]pyridine NMR (D₂O, δ): 0.65 (3H, t, J=7.5 Hz), 1.36 (2H, m), 2.41 (3H, s), 2.69 (2H, t, J=8 Hz), 5.37 (2H, s), 6.27 (1H, d, J=4 Hz), 6.66 (1H, d, J=4 Hz), 6.81 (2H, d, J=8 Hz), 6.90 (1H, d, J=5 Hz), 6.94 (2H, d, J=8 Hz), 7.94 (1H, d, J=5 Hz)

(12) Sodium salt of 2-butyl-7-methyl-3-[3-nitro-4-[2-(1H-tetrazol-5-yl)-1-pyrrolyl]benzyl]-3H-imidazo[4,5-b]pyridine NMR (D₂O, δ): 0.72 (3H, t, J=7 Hz), 1.22 (2H, m), 1.50 (2H, m), 2.83 (2H, t, J=7 Hz), 5.52 (2H, s), 6.39 (1H, t, J=3 Hz), 6.76 (1H, dd, J=3 Hz & 1 Hz), 6.83 (1H, d, J=1 Hz), 7.00 (1H, d, J=5 Hz), 7.28-7.42 (2H, m), 7.62 (1H, s), 8.00 (1H, d, J=5 Hz)

(13) Sodium salt of 2-butyl-3-[3-chloro-4-[2-(1H-tetrazol-5-yl)-1-pyrrolyl]benzyl]-7-methyl-3H-imidazo[4,5-b]pyridine mp: 49°-50° C.

NMR (D₂O, δ): 0.62 (3H, t, J=7.5 Hz), 1.10 (2H, m), 1.40 (2H, m), 2.43 (3H, s), 2.71 (2H, t, J=8 Hz), 5.34 (2H, s), 6.27 (1H, t, J=3 Hz), 6.52 (1H, br s), 6.73 (1H, d, J=4 Hz), 6.83 (1H, d, J=5 Hz), 6.90 (1H, d, J=8 Hz), 7.00 (2H, m), 7.90 (1H, d, J=5 Hz)

(14) Potassium salt of 3-[4-[4-bromo-2-(1H-tetrazol-5-yl)-1-pyrrolyl]benzyl]-7-methyl-2-propyl-3H-imidazo[4,5-b]pyridine NMR (D₂O, δ): 0.69 (3H, t, J=7.5 Hz), 1.43 (2H, m), 2.60 (2H, t, J=7.5 Hz), 5.74 (2H, s), 6.26 (1H, d, J=1 Hz), 6.52 (2H, d, J=9 Hz), 6.55 (1H, d, J=1 Hz), 6.71 (1H, d, J=5 Hz), 6.73 (2H, d, J=5 Hz), 7.82 (1H, d, J=5 Hz)

EXAMPLE 7

The following compounds were obtained according to similar manners to those of Example 1 and Example 3, successively.

(1) Sodium salt of 3-[4-[4-bromo-3-chloro-2-(1H-tetrazol-5-yl)-1-pyrrolyl]benzyl-2-butyl-7-methyl-3H-imidazo[4,5-b]pyridine mp: 160°-175° C.

NMR (D₂O, δ): 0.43 (3H, t, J=7 Hz), 0.94 (2H, m), 1.27 (2H, m), 2.66 (2H, t, J=7 Hz), 5.43 (2H, s), 6.63 (1H, s), 6.76 (2H, d, J=9 Hz), 6.83 (1H, d, J=5 Hz), 6.97 (2H, d, J=9 Hz), 7.96 (1H, d, J=5 Hz)

(2) Sodium salt of 3-[4-(2-bromo-5-(1H-tetrazol-5-yl)-1-pyrrolyl]-2-methoxybenzyl]-2-butyl-7-methyl-3H-imidazo[4,5-b]pyridine NMR (CDCl₃, δ): 0.51 (3H, t, J=7 Hz), 1.00 (2H, m), 1.28 (2H, m), 2.38 (3H, s), 2.57 (2H, t, J=7 Hz), 3.52 (3H, s), 5.20 (2H, s), 6.15 (1H, d, J=2 Hz), 6.28 (1H, d, J=8 Hz), 6.41 (1H, d, J=8 Hz), 6.59 (1H, d, J=2 Hz), 6.66 (1H, s), 6.82 (1H, d, J=4 Hz), 7.92 (1H, d, J=4 Hz)

EXAMPLE 8

A mixture of 2-butyl-7-methyl-3-[3-nitro-4-[2-(1H-tetrazol-5-yl)-1-pyrrolyl]benzyl]-3H-imidazo[4,5-b]pyridine (145 mg), 10% palladium on carbon (30 mg), and methanol (5 ml) was stirred at room temperature for 5 hours under hydrogen atmosphere (4 atom). After vacuum filtration, the filtrate was evaporated in vacuo to give a yellow residue of 3-[3-amino-4-[2-(1H-tetrazol-5-yl)-1-pyrrolyl]benzyl]-2-butyl-7-methyl-3H-imidazo[4,5-b]pyridine (130 mg). This residue was treated with acetic anhydride (1 ml) and pyridine (2 ml) at room temperature for 2 hours. The reaction mixture was evaporated in vacuo and purified by preparative thin layer chromatography (ethyl acetate-acetic acid=19:1) to give a brownish viscous oil (65 ml). To a solution of the oil in ethanol (2 ml) was added a solution of sodium hydrogencarbonate (12.8 mg) in water (1 ml) and the mixture was evaporated in vacuo. The residue was dissolved in water (2 ml) and lyophilized to afford sodium salt of 3-[3-acetamido-4-[2-(1H-tetrazol-5-yl)-1-pyrrolyl]benzyl]-2-butyl-7-methyl-3H-imidazo[4,5-b]pyridine (65 mg) as an amorphous powder.

NMR (D₂O, δ): 0.79 (3H, t, J=7 Hz), 1.28 (2H, m), 1.56 (2H, m), 1.74 (3H, s), 2.55 (3H, s), 2.87 (2H, t, J=7 Hz), 5.49 (2H, s), 6.41 (1H, br s), 6.73 (1H, br s), 6.81 (1H, br s), 6.96 (1H, d, J=8 Hz), 7.08 (1H, d, J=5 Hz), 7.19 (1H, br s), 7.21 (1H, d, J=8 Hz), 8.08 (1H, d, J=5 Hz)

EXAMPLE 9

The following compounds were obtained according to a similar manner to that of Example 1.

(1)

2-Butyl-3-[4-[4-chloro-2-(1H-tetrazol-5-yl)-1-pyrrolyl]-benzyl]-7-methyl-3H-imidazo[4,5-b]pyridine mp: 186°-190.5° C.

NMR (CD₃OD-CDCl₃, δ): 0.91 (3H, t, J=7.5 Hz), 1.31-1.52 (2H, m), 1.64-1.83 (2H, m), 2.70 (3H, s), 2.91 (2H, t, J=7.5 Hz), 5.58 (2H, s), 6.85 (1H, d, J=1.5 Hz), 6.98 (1H, d, J=1.5 Hz), 7.14 (1H, d, J=5.0 Hz), 7.19 (4H, s), 8.21 (1H, d, J=5.0 Hz)

(2)

3-[4-[4-Chloro-2-(1H-tetrazol-5-yl)-1-pyrrolyl]benzyl]-7-methyl-2-propyl-3H-imidazo[4,5-b]pyridine mp: 225°-227° C.

NMR (DMSO-d₆, δ): 0.95 (3H, t, J=7.5 Hz), 1.62-1.86 (2H, m), 2.57 (3H, s), 2.84 (2H, t, J=7.5 Hz), 5.58 (2H, s), 6.92 (1H, d, J=1 Hz), 7.10 (1H, d, J=5 Hz), 7.14-7.35 (4H, m), 7.49 (1H, d, J=1 Hz), 8.18 (1H, d, J=5 Hz)

EXAMPLE 10

The following compounds were obtained according to a similar manner to that of Example 3.

(1) Sodium salt of 2-butyl-3-[4-[4-chloro-2-(1H-tetrazol-5-yl)-1-pyrrolyl]-benzyl]-7-methyl-3H-imidazo[4,5-b]pyridine mp: 161°-170° C.

NMR (D₂O, δ): 0.68 (3H, t, J=7.5 Hz), 1.02-1.23 (2H, m), 1.31-1.50 (2H, m), 2.44 (3H, s), 2.67 (2H, t, J=7.5 Hz), 5.31 (2H, s), 6.51 (1H, d, J=1.0 Hz), 6.57 (1H, d, J=1.0 Hz), 6.65 (2H, d, J=8.5 Hz), 6.82 (2H, d, J=8.5 Hz), 6.90 (1H, d, J=5.0 Hz), 7.92 (1H, d, J=5.0 Hz)

(2) Sodium salt of 3-[4-[4-chloro-2-(1H-tetrazol-5-yl)-1-pyrrolyl]benzyl]-7-methyl-2-propyl-3H-imidazo[4,5-b]pyridine mp: 184°-187° C.

NMR (D₂O, δ): 0.74 (3H, t, J=7.5 Hz), 1.35-1.59 (2H, m), 2.42 (3H, s), 2.65 (2H, t, J=7.5 Hz), 5.30 (2H, s), 6.44 (1H, d, J=1 Hz), 6.51-6.63 (3H, m), 6.77 (2H, d, J=8 Hz), 6.86 (1H, d, J=5 Hz), 7.39 (1H, d, J=5 Hz)

EXAMPLE 11

The following compounds were obtained according to a similar manner to that of Example 1.

(1)

2-Butyl-3-[3-fluoro-4-[2-(1H-tetrazol-5-yl)-1-pyrrolyl]-benzyl]-7-methyl-3H-imidazo[4,5-b]pyridine mp: 106.5°-108° C.

NMR (DMSO-d₆, δ): 0.89 (3H, t, J=7.5 Hz), 1.27-1.50 (2H, m), 1.62-1.81 (2H, m), 2.57 (3H, s), 2.89 (2H, t, J=7.5 Hz), 5.60 (2H, s), 6.46 (1H, t, J=3.0 Hz), 6.94-7.04 (2H, m), 7.11 (1H, d, J=5.0 Hz), 7.17-7.29 (2H, m), 7.41 (1H, t, J=8.5 Hz), 8.18 (1H, d, J=5.0 Hz)

(2)

2-Butyl-3-[4-[2-bromo-5-(1H-tetrazol-5-yl)-1-pyrrolyl]-2-fluorobenzyl]-7-methyl-3H-imidazo[4,5-b]pyridine NMR (DMSO-d₆, δ): 0.85 (3H, t, J=7.5 Hz), 1.25-1.47 (2H, m), 1.59-1.78 (2H, m), 2.57 (3H, s), 2.86 (2H, t, J=7.5 Hz), 5.62 (2H, s), 6.58 (1H, d, J=4.5 Hz), 6.89-7.16 (2H, m), 6.93 (1H, d, J=4.5 Hz), 7.10 (1H, d, J=5.0 Hz), 7.40 (1H, dd, J=10.0 Hz & 1.0 Hz), 8.18 (1H, d, J=5.0 Hz)

(3)

3-[[2-[4-Bromo-2-(1H-tetrazol-5-yl)-1-pyrrolyl]pyridin-5-yl]methyl]-2-butyl-7-methyl-3H-imidazo[4,5-b]pyridine NMR (DMSO-d₆, δ): 0.88 (3H, t, J=7.5 Hz), 1.27-1.49 (2H, m), 1.61-1.80 (2H, m), 2.55 (3H, s), 2.90 (2H, t, J=7.5 Hz), 5.56 (2H, s), 6.72 (1H, d, J=1.5 Hz), 7.09 (1H, d, J=5.0 Hz), 7.17 (1H, d, J=8.5 Hz), 7.58 (1H, d, J=1.5 Hz), 7.60 (1H, dd, J=8.5 Hz & 1.0 Hz), 8.15 (1H, d, J=5.0 Hz), 8.31 (1H, d, J=1.0 Hz)

(4)

3-[3-Bromo-4-[2-bromo-5-(1H-tetrazol-5-yl)-1-pyrrolyl]benzyl]-2-butyl-7-methyl-3H-imidazo[4,5-b]pyridine NMR (DMSO-d₆, δ): 0.83 (3H, t, J=7.5 Hz), 1.25-1.45 (2H, m), 1.56-1.72 (2H, m), 2.58 (3H, s), 2.88 (2H, t, J=7.5 Hz), 5.63 (2H, s), 6.62 (1H, d, J=4.5 Hz), 7.01 (1H, d, J=4.5 Hz), 7.12 (1H, d, J=5.0 Hz), 7.18 (1H, dd, J=8.5 Hz & 1.0 Hz), 7.42 (1H, d, J=8.5 Hz), 7.69 (1H, d, J=1.0 Hz), 8.19 (1H, d, J=5.0 Hz)

(5)

2-Butyl-3-[4-[2-cyano-5-(1H-tetrazol-5-yl)-1-pyrrolyl]-benzyl]-7-methyl-3H-imidazo[4,5-b]pyridine NMR (DMSO-d₆, δ): 0.87 (3H, t, J=7.5 Hz), 1.22-1.45 (2H, m), 1.57-1.76 (2H, m), 2.57 (3H, s), 2.83 (2H, t, J=7.5 Hz), 5.58 (2H, s), 6.58 (1H, d, J=4 Hz), 7.06-7.33 (6H, m), 8.18 (1H, d, J=5 Hz)

(6)

7-Methyl-2-propyl-3-[4-[2-(1H-tetrazol-5-yl)-4-vinyl-1-pyrrolyl]benzyl]-3H-imidazo[4,5-b]pyridine NMR (CDCl₃+CD₃OD, δ): 0.92 (3H, t, J=7.5 Hz), 1.59-1.82 (2H, m), 2.60 (3H, s), 2.72 (2H, t, J=7.5 Hz), 4.96 (1H, dd, J=11 Hz & 1 Hz), 5.32-5.50 (3H, m), 6.50 (1H, dd, J=11 Hz, 17.5 Hz), 6.83-6.90 (2H, m), 6.89-7.08 (5H, m), 8.05 (1H, d, J=5 Hz)

EXAMPLE 12

A mixture of 7-methyl-2-propyl-3-[4-[2-(1H-tetrazol-5-yl)-4-vinyl-1-pyrrolyl]benzyl]-3H-imidazo[4,5-b]pyridine (40 mg), 10% palladium on carbon (10 mg) and methanol (5 ml) was stirred at room temperature for 4 hours under hydrogen atmosphere (3 atm). After filtration, the filtrate was evaporated in vacuo. The residue was purified by preparative thin layer chromatography (dichloromethane:methanol=5:1) to give 3-[4-[4-ethyl-2-(1H-tetrazol-5-yl)-1-pyrrolyl]benzyl]-7-methyl-2-propyl-3H-imidazo[4,5-b]pyridine (20 ml).

NMR (CDCl₃, +CD₃OD, δ): 0.99 (3H, t, J=7.5 Hz), 1.21 (3H, t, J=7.5 Hz), 1.64-1.87 (2H, m), 2.44-2.60 (2H, m), 2.64 (3H, s), 2.80 (2H, t, J=7.5 Hz), 5.46 (2H, s), 6.67-6.76 (2H, m), 6.97-7.13 (5H, m), 8.13 (1H, d, J=5 Hz)

EXAMPLE 13

A mixture of 3-[4-(2-cyano-1-pyrrolyl)-3-methylbenzyl]-7-methyl-3-propyl-3H-imidazo[4,5-b]pyridine (260 mg), sodium azide (183 mg), triethylamine hydrochloride (484 mg) and 1,3-dimethyl-2-imidazolidinone (5 ml) were stirred at 130° C. for 2 days under nitrogen atmosphere. The mixture was poured into water (25 ml) and the pH value was adjusted to 4 with 7% hydrochloric acid. The mixture was extracted with ethyl acetate and the organic layer was washed with brine, dried over magnesium sulfate and evaporated in vacuo. The residue was purified by preparative thin layer chromatography ($CH_2Cl_2$-MeOH=6:1) to afford 7-methyl-3-[3-methyl-4-[2-(1H-tetrazol-5-yl)-1-pyrrolyl]benzyl]-2-propyl-3H-imidazo[4,5-b]pyridine (225 mg).

NMR ($CDCl_3$, δ): 0.96 (3H, t, J=7.5 Hz), 1.67-2.00 (5H, m), 2.72 (3H, s), 2.98 (2H, t, J=7.5 Hz), 5.54 (2H, s), 6.36-6.43 (1H, m), 6.77-6.84 (1H, m), 6.93-7.22 (5H, m), 8.29 (1H, d, J=5 Hz)

EXAMPLE 14

The following compounds were obtained according to a similar manner to that of Example 13.

(1)
1-[4-[4-Bromo-2-(1H-tetrazol-5-yl)-1-pyrrolyl]benzyl]-2-butyl-6-ethoxycarbonyl-1H-benzimidazole NMR ($CD_3OD$, δ): 0.91 (3H, t, J=7.5 Hz), 1.23-1.53 (5H, m), 1.65-1.86 (2H, m), 2.92 (2H, t, J=7.5 Hz), 4.35 (2H, q, J=7.5 Hz), 5.59 (2H, s), 6.65 (1H, d, J=1 Hz), 7.01-7.20 (5H, m), 7.69 (1H, d, J=8 Hz), 7.95 (1H, dd, J=8 Hz & 1 Hz), 8.10 (1H, d, J=1 Hz)

(2)
3-[4-[4-Bromo-2-(1H-tetrazol-5-yl)-1-pyrrolyl]benzyl]-2-butyl-5-methoxy-3H-imidazo[4,5-b]pyridine mp: 235°-241° C.

NMR ($CDCl_3$, +$CD_3OD$, δ): 0.92 (3H, t, J=7.5 Hz), 1.38-1.51 (2H, m), 1.63-1.85 (2H, m), 2.75-2.90 (2H, t-like, J=7.5 Hz), 3.98 (3H, s), 5.48 (2H, s), 6.72 (1H, d, J=9 Hz), 6.91 (1H, d, J=1 Hz), 7.01 (1H, d, J=1 Hz), 7.15-7.32 (4H, m), 7.89 (1H, d, J=9 Hz)

(3)
2-Butyl-3-[4-[4-chloro-2-(1H-tetrazol-5-yl)-1-pyrrolyl]benzyl]-3H-imidazo[4,5-b]pyridine NMR ($CDCl_3$, δ): 0.82 (3H, t, J=7.5 Hz), 1.19-1.46 (2H, m), 1.59-1.81 (2H, m), 2.78 (2H, t, J=7.5 Hz), 5.48 (2H, s), 6.83-7.0 (2H, m), 7.00-7.38 (5H, m), 7.98 (2H, d, J=8 Hz), 8.37 (2H, d, J=5 Hz)

EXAMPLE 15

The following compounds were obtained according to a similar manner to that of Example 3.

(1) Sodium salt of
2-butyl-3-[3-fluoro-4-[2-(1H-tetrazol-5-yl)-1-pyrrolyl]benzyl]-7-methyl-3H-imidazo[4,5-b]pyridine mp: 93°-131° C.

NMR ($D_2O$, δ): 0.66 (3H, t, J=7.5 Hz), 1.03-1.25 (2H, m), 1.32-1.52 (2H, m), 2.45 (3H, s), 2.72 (2H, t, J=7.5 Hz), 5.35 (2H, s), 6.32 (1H, t, J=3.5 Hz), 6.63-6.90 (4H, m), 6.89 (1H, d, J=5.0 Hz), 6.94 (1H, t, J=8.0 Hz), 7.91 (1H, d, J=5.0 Hz)

(2) Sodium salt of
2-butyl-3-[4-[2-bromo-5-(1H-tetrazol-5-yl)-1-pyrrolyl]-2-fluorobenzyl]-7-methyl-3H-imidazo[4,5-b]pyridine mp: 129°-151° C.

NMR ($D_2O$, δ): 0.52 (3H, t, J=7.5 Hz), 0.90-1.12 (2H, m), 1.20-1.41 (2H, m), 2.32 (3H, s), 2.65 (2H, t, J=7.5 Hz), 5.37 (2H, s), 6.11 (1H, d, J=4.0 Hz), 6.50 (1H, d, J=8.0 Hz), 6.61 (1H, d, J=4.0 Hz), 6.68 (1H, d, J=8.0 Hz), 6.75-6.87 (2H, m), 7.91 (1H, d, J=5.0 Hz)

(3) Sodium salt of
3-[[2-[4-bromo-2-(1H-tetrazol-5-yl)-1-pyrrolyl]pyridin-5-yl]methyl]-2-butyl-7-methyl-3H-imidazo[4,5-b]pyridine mp: 155°-170.5° C.

NMR ($D_2O$, δ): 0.72 (3H, t, J=7.5 Hz), 1.09-1.33 (2H, m), 1.40-1.58 (2H, m), 2.48 (3H, s), 2.81 (2H, t, J=7.5 Hz), 5.43 (2H, s), 6.61 (1H, d, J=9.0 Hz), 6.64 (1H, d, J=1.5 Hz), 6.95 (1H, d, J=5.0 Hz), 6.97 (1H, d, J=1.5 Hz), 7.30 (1H, dd, J=9.0 Hz & 1.0 Hz), 7.93 (1H, d, J=5.0 Hz), 8.13 (1H, d, J=1.0 Hz)

(4) Sodium salt of
3-[3-bromo-4-[2-bromo-5-(1H-tetrazol-5-yl)-1-pyrrolyl]benzyl]-2-butyl-7-methyl-3H-imidazo[4,5-b]pyridine mp: 142°-169° C.

NMR ($D_2O$, δ): 0.50 (3H, t, J=7.5 Hz), 0.89-1.11 (2H, m), 1.21-1.42 (2H, m), 2.38 (3H, s), 2.70 (2H, t, J=7.5 Hz), 5.39 (2H, s), 6.21 (1H, d, J=4.5 Hz), 6.72 (1H, d, J=4.5 Hz), 6.84 (1H, d, J=5.0 Hz), 7.04 (2H, s), 7.29 (1H, s), 7.97 (1H, d, J=5.0 Hz)

(5) Sodium salt of
2-butyl-3-[4-[2-cyano-5-(1H-tetrazol-5-yl)-1-pyrrolyl]benzyl]-7-methyl-3H-imidazo[4,5-b]pyridine NMR ($CDCl_3$, δ): 0.60 (3H, t, J=7.5 Hz), 0.97-1.20 (2H, m), 1.20-1.41 (2H, m), 2.44 (3H, s), 2.71 (2H, t, J=7.5 Hz), 5.38 (2H, s), 6.72 (1H, d, J=4 Hz), 6.88-7.08 (6H, m), 7.97 (1H, d, J=5 Hz)

(6) Sodium salt of
7-methyl-3-[3-methyl-4-[2-(1H-tetrazol-5-yl)-1-pyrrolyl]benzyl]-2-propyl-3H-imidazo[, 4,5-b]pyridine mp: 125°-128° C.

NMR ($D_2O$, δ): 0.80 (3H, t, J=7.5 Hz), 1.40-1.70 (5H, m), 2.51 (3H, s), 2.77 (2H, t, J=7.5 Hz), 5.38 (2H, s), 6.32-6.41 (1H, m), 6.59-6.68 (1H, m), 6.68-6.82 (2H, m), 6.82-6.96 (2H, m), 7.00 (1H, d, J=5 Hz), 8.01 (1H, d, J=5 Hz)

(7) Sodium salt of
2-butyl-3-[4-[4-chloro-2-(1H-tetrazol-5-yl)-1-pyrrolyl]benzyl]-3H-imidazo[4,5-b]pyridine mp: 190°-193° C.

NMR ($D_2O$, δ): 0.62 (3H, t, J=7.5 Hz), 0.96-1.19 (2H, m), 1.32-1.56 (2H, m), 2.60 (2H, t, J=7.5 Hz), 5.30 (2H, s), 6.41 (1H, d, J=2 Hz), 6.52 (1H, d, J=2 Hz), 6.62 (2H, d, J=8 Hz), 6.82 (2 H, d, J=8 Hz), 7.10 (1H, dd, J=5 Hz & 8 Hz), 7.85 (1H, dd, J=8 Hz & 1 Hz), 8.06 (1H, dd, J=5 Hz & 1 Hz)

(8) Sodium salt of
7-methyl-2-propyl-3-[4-[2-(1H-tetrazol-5-yl)-4-vinyl-1-pyrrolyl]benzyl]-3H-imidazo[4,5-b]pyridine NMR ($D_2O$, δ): 0.79 (3H, t, J=7.5 Hz), 1.40-1.64 (2H, m), 2.52 (3H, s), 2.63-2.85 (2H, m), 5.00-5.12 (1H, m), 5.32–5.60 (3H, m), 6.42–7.14 (8H, m), 7.92–8.05 (1H, m)

(9) Sodium salt of 3-[4-[4-ethyl-2-(1H-tetrazol-5-yl)-1-pyrrolyl]benzyl]-7-methyl-2-propyl-3H-imidazo[4,5-b]pyridine NMR (D$_2$O, δ): 0.84 (3H, t, J=7.5 Hz), 1.17 (3H, t, J=7.5 Hz), 1.50–1.70 (2H, m), 2.39–2.64 (5H, m), 2.70–2.87 (2H, m), 5.48 (2H, s), 6.58–6.70 (2H, m), 6.83 (2H, d, J=8 Hz), 6.94 (2H, d, J=8 Hz), 7.12 (1H, d, J=5 Hz), 8.08 (1H, d, J=5 Hz)

EXAMPLE 16

The following compounds were obtained according to similar manners to those of Examples 1 and 3, successively.

(1) Sodium salt of 3-[4-[4-bromo-2-(1H-tetrazol-5-yl)-1-pyrrolyl]benzyl]-2-butyl-3H-imidazo[4,5-d]pyrimidine NMR (D$_2$O, δ): 0.60 (3H, t, J=7.5 Hz), 0.93–1.21 (2H, m), 1.32–1.58 (2H, m), 2.65 (2H, t, J=7.5 Hz), 5.31 (2H, s), 6.39 (1H, d, J=1 Hz), 6.48 (1H, d, J=1 Hz), 6.70 (2H, d, J=8 Hz), 6.91 (2H, d, J=8 Hz), 8.69 (1H, s), 8.82 (1H, s)

(2) Sodium salt of 1-[4-[4-bromo-2-(1H-tetrazol-5-yl)-1-pyrrolyl]benzyl]-2-butylthieno[3,4-d]imidazole NMR (D$_2$O, δ): 0.72 (3H, t, J=7 Hz), 1.19 (2H, m), 1.50 (2H, m), 2.60 (2H, t, J=7 Hz}, 4.95 (2H, s), 6.00 (1H, s), 6.44 (1H, s), 6.64 (2H, d, J=9 Hz), 6.80 (2H, d, J=9 Hz)

(3) Sodium salt of 1-[4-[4-bromo-2-(1H-tetrazol-5-yl)-1-pyrrolyl]benzyl]-2-butyl-4-chloro-5-hydroxymethylimidazole NMR (D$_2$O, δ): 0.69 (3H, t, J=7 Hz), 1.11 (2H, m), 1.40 (2H, m), 2.47 (2H, t, J=7 Hz), 4.43 (2H, s). 5.20 (2H, s), 6.69 (1H, d, J=2 Hz), 6.77 (1H, d, J=2 Hz), 6.86 (4H, s)

EXAMPLE 17

The following compounds were obtained according to similar manners to those of Examples 13 and 3, successively.

(1) Sodium salt of 3-[4-[4-bromo-2-(1H-tetrazol-5-yl)-1-pyrrolyl]benzyl]-2-butyl-5-chloro-3H-imidazo[4,5-b]pyridine NMR (D$_2$O, δ): 0.63 (3H, t, J=7.5 Hz), 0.94–1.19 (2H, m), 1.33–1.55 (2H, m), 2.61 (2H, t, J=7.5 Hz), 5.20 (2H, s), 6.38 (1H, d, J=1 Hz), 6.57 (1H, d, J=1 Hz), 6.68 (2H, d, J=8 Hz), 6.84 (2H, d, J=8 Hz), 6.93 (1H, d, J=8 Hz), 7.69 (1H, d, J=8 Hz)

(2) Sodium salt of 2-butyl-3-[4-[4-tert-butyl-2-(1H-tetrazol-5-yl)-1-pyrrolyl]benzyl]-7-methyl-3H-imidazo[4,5-b]pyridine mp: 188°–195° C.

NMR (D$_2$O, δ): 0.61 (3H, t, J=7.5 Hz), 0.85–1.18 (11H, m), 1.30–1.50 (2H, m), 2.44 (3H, s), 2.63 (2H, t), 5.31 (2H, s), 6.38 (1H, d), 6.57 (1H, d), 6.68 (2H, d, J=8 Hz), 6.84 (2H, d, J=8 Hz), 6.92 (1H, d, J=5 Hz), 7.93 (1H, d, J=5 Hz)

EXAMPLE 18

The following compounds were obtained according to a similar manner to that of Example 1.

(1) A mixture of 3-[4-[2-bromo-1-methyl-4-(1H-tetrazol-5-yl)-3-pyrrolyl]benzyl]-7-methyl-2-propyl-3H-imidazo[4,5-b]pyridine and 3-[4-[2-bromo-1-methyl-3-(1H-tetrazol-5-yl)-4-pyrrolyl]benzyl]-7-methyl-2-propyl-3H-imidazo[4,5-b]pyridine.

NMR (DMSO-d$_6$, δ): 0.93 (3H, t, J=7.5 Hz), 1.61–1.86 (2H, m), 2.57 (3H, s), 2.83 (2H, t, J=7.5 Hz), 3.70 (3H, s), 5.51 (2H, s), 7.05–7.26 (5H, m), 7.51 (1H, s), 8.16 (1H, d, J=5 Hz)

(2) 3-[4-[1-Methyl-4-(1H-tetrazol-5-yl)-3-pyrrolyl]benzyl]-7-methyl-2-propyl-3H-imidazo[4,5-b]pyridine NMR (CDCl$_3$+CD$_3$OD, δ): 1.02 (3H, t, J=7.5 Hz), 1.71–1.93 (2H, m), 2.91 (2H, t, J=7.5 Hz), 2.65 (3H, s), 2.91 (2H, t, J=7.5 Hz), 3.75 (3H, s), 5.51 (2H, s), 6.72 (1H, d, J=2 Hz), 7.03 (2H, d, J=9 Hz), 7.11 (1H, d, J=5 Hz), 7.20 (2H, d, J=9 Hz), 7.33 (1H, d, J=2 Hz), 8.19 (1H, d, J=5 Hz)

EXAMPLE 19

The following compounds were obtained according to a similar manner to that of Example 3.

(1) A mixture of sodium salt of 3-[4-[2-bromo-1-methyl-4-(1H-tetrazol-5-yl)-3-pyrrolyl]benzyl]-7-methyl-2-propyl-3H-imidazo[4,5-b]pyridine and sodium salt of 3-[4-[2-bromo-1-methyl-3-(1H-tetrazol-5-yl)-4-pyrrolyl]benzyl]-7-methyl-2-propyl-3H-imidazo[4,5-b]pyridine.

mp: 83°–85° C.

NMR (D$_2$O, δ): 0.63 (3H, t, J=7.5 Hz), 1.27–1.52 (2H, m), 2.31 (3H, s), 2.59 (2H, t, J=7.5 Hz), 3.23 (3H, s), 5.24 (2H, s), 6.67–6.90 (5H, m), 7.18 (1H, s), 7.88 (1H, d, J=5 Hz)

(2) Sodium salt of 3-[4-[1-methyl-4-(1H-tetrazol-5-yl)-3-pyrrolyl]benzyl]-7-methyl-2-propyl-3H-imidazo[4,5-b]pyridine mp: 140°–143° C.

NMR (D$_2$O, δ): 0.78 (3H, t, J=7.5 Hz), 1.40–1.65 (2H, m), 2.48 (3H, s), 2.64 (2H, t, J=7.5 Hz), 3.58 (3H, s), 5.28 (2H, s), 6.52 (1H, d, J=2 Hz), 6.73 (2H, d, J=9 Hz), 6.88 (2H, d, J=9 Hz), 6.99 (1H, d, J=5 Hz), 7.05 (1H, d, J=2 Hz), 7.97 (1H, d, J=5 Hz)

EXAMPLE 20

The following compounds were obtained according to a similar manner to that of Example 1.

(1) 7-Methyl-3-[4-[4-methyl-2-(1H-tetrazol-5-yl)-1-pyrrolyl]benzyl]-2-propyl-3H-imidazo[4,5-b]pyridine NMR (DMSO-d$_6$, δ): 0.93 (3H, t, J=7.5 Hz), 1.62–1.84 (2H, m), 2.09 (3H, s), 2.56 (3H, s), 2.83 (2H, t, J=7.5 Hz), 5.52 (2H, s), 6.67 (1H, d, J=1.0 Hz), 6.99 (1H, d, J=1.0 Hz), 7.09 (1H, d, J=5.0 Hz), 7.18 (4H, s), 8.18 (1H, d, J=5.0 Hz)

(2)

7-Methyl-3-[4-[5-methylthio-2-(1H-tetrazol-5-yl)-1-pyrrolyl]benzyl]-2-propyl-3H-imidazo[4,5-b]pyridine mp: 181°-183° C.

NMR (DMSO-d$_6$, δ): 0.91 (3H, t, J=7.5 Hz), 1.57-1.78 (2H, m), 2.18 (3H, s), 2.57 (3H, s), 2.81 (2H, t, J=7.5 Hz), 5.60 (2H, s), 6.51 (1H, d, J=5 Hz), 6.91 (1H, d, J=5 Hz), 7.22 (4H, s-like), 8.19 (1H, d, J=5 Hz)

(3)

3-[4-[4-Chloro-2-(1H-tetrazol-5-yl)-1-pyrrolyl]benzyl]-2-ethyl-5,7-dimethyl-3H-imidzo[4,5-b]pyridine NMR (CDCl$_3$, δ): 1.31 (3H, t, J=7.5 Hz), 2.60 (3H, s), 2.62 (3H, s), 2.81 (2H, q, J=7.5 Hz), 5.50 (2H, s), 6.83 (1H, d, J=1 Hz), 6.90-6.98 (2H, m), 7.03-7.20 (4H, m)

EXAMPLE 21

The following compounds were obtained according to a similar manner to that of Example 13.

(1)

7-Methyl-3-[4-[2-methyl-5-(1H-tetrazol-5-yl)-1-pyrrolyl]benzyl]-2-propyl-3H-imidazo[4,5-b]pyridine mp: 184°-186° C.

NMR (DMSO-d$_6$, δ): 0.90 (3H, t, J=7.5 Hz), 1.57-1.79 (2H, m), 1.99 (3H, s), 2.57 (3H, s), 2.82 (2H, t, J=7.5 Hz), 5.60 (2H, s), 6.18 (1H, d, J=4.5 Hz), 6.80 (1H, d, J=4.5 Hz), 7.10 (1H, d, J=5.0 Hz), 7.22 (4H, s), 8.19 (1H, d, J=5.0 Hz)

(2)

3-[4-[3-Chloro-2-methyl-5-(1H-tetrazol-5-yl)-1-pyrrolyl]benzyl]-7-methyl-2-propyl-3H-imidazo[4,5-b]pyridine mp: 190.5°-192.5° C.

NMR (DMSO-d$_6$, δ): 0.90 (3H, t, J=7.5 Hz), 1.56-1.79 (2H, m), 1.98 (3H, s), 2.57 (3H, s), 2.82 (2H, t, J=7.5 Hz), 5.60 (2H, s), 6.90 (1H, s), 7.11 (1H, d, J=5.0 Hz), 7.24 (4H, s), 8.18 (1H, d, J=5.0 Hz)

EXAMPLE 22

The following compounds were obtained according to a similar manner to that of Example 3.

(1) Sodium salt of 7-methyl-3-[4-[4-methyl-2-(1H-tetrazol-5-yl)-1-pyrrolyl]benzyl]-2-propyl-3H-imidazo[4,5-b]pyridine NMR (D$_2$O, δ): 0.74 (3H, t, J=7.5 Hz), 1.35-1.58 (2H, m), 1.97 (3H, s), 2.43 (3H, s), 2.63 (2H, t, J=7.5 Hz), 5.26 (2H, s), 6.25 (1H, d, J=1.0 Hz), 6.51 (1H, d, J=1.0 Hz), 6.58 (2H, d, J=9.0 Hz), 6.73 (2H, d, J=9.0 Hz), 6.87 (1H, d, J=5.0 Hz), 7.89 (1H, d, J=5.0 Hz)

(2) Sodium salt of 7-methyl-3-[4-[2-methyl-5-(1H-tetrazol-5-yl)-1-pyrrolyl]benzyl]-2-propyl-3H-imidazo[4,5-b]pyridine NMR (D$_2$O, δ): 0.66 (3H, t, J=7.5 Hz), 1.23-1.48 (2H, m), 1.62 (3H, s), 2.35 (3H, s), 2.65 (2H, t, J=7.5 Hz), 5.27 (2H, s), 5.97 (1H, d, J=4.5 Hz), 6.59 (1H, d, J=4.5 Hz), 6.71 (2H, d, J=9.0 Hz), 6.76 (1H, d, J=5.0 Hz), 6.89 (2H, d, J=9.0 Hz), 7.85 (1H, d, J=5.0 Hz)

(3) Sodium salt of 3-[4-[3-chloro-2-methyl-5-(1H-tetrazol-5-yl)-1-pyrrolyl]benzyl]-7-methyl-2-propyl-3H-imidazo[4,5-b]pyridine NMR (D$_2$O, δ): 0.57 (3H, t, J=7.5 Hz), 1.22-1.48 (2H, m), 1.36 (3H, s), 2.29 (3H, s), 2.61 (2H, t, J=7.5 Hz), 5.27 (2H, s), 6.48 (1H, s), 6.58 (2H, d, J=9.0 Hz), 6.71 (1H, d, J=5.0 Hz), 6.87 (2H, d, J=9.0 Hz), 7.82 (1H, d, J=5.0 Hz)

(4) Sodium salt of 7-methyl-3-[4-[5-methylthio-2-[1H-tetrazol-5-yl)-1-pyrrolyl]benzyl]-2-propyl-3H-imidazo[4,5-b]pyridine NMR (D$_2$O, δ): 0.68 (3H, t, J=7.5 Hz), 1.25-1.55 (2H, m), 1.79 (3H, s), 2.40 (3H, s), 2.69 (3H, t, J=7.5 Hz), 5.38 (2H, s), 6.35 (1H, d, J=5 Hz), 6.68 (1H, d, J=5 Hz), 6.85 (2H, d, J=8 Hz), 6.95 (2H, d, J=8 Hz), 7.93 (1H, d, J=5 Hz)

(5) Sodium salt of 3-[4-[4-chloro-2-(1H-tetrazol-5-yl)-1-pyrrolyl]benzyl]-2-ethyl-5,7-dimethyl-3H-imidazo[4,5-b]pyridine NMR (D$_2$O, δ): 1.13 (3H, t, J=7.5 Hz), 2.39 (3H, s), 2.42 (3H, s), 2.72 (2H, q, J=7.5 Hz), 5.38 (2H, s), 6.59-6.67 (2H, m), 6.70 (2H, d, J=8 Hz), 6.81-6.93 (3H, m)

EXAMPLE 23

The following compound was obtained according to similar manners to those of Examples 1 and 3, successively.

Sodium salt of 2-butyl-7-methyl-3-[4-[2-methyl-5-(1H-tetrazol-5-yl)-1-pyrrolyl]benzyl]-3H-imidazo[4,5-b]pyridine NMR (D$_2$O, δ): 0.69 (3H, t, J=7 Hz), 1.16 (2H, m), 1.40 (2H, m), 1.88 (3H, s), 2.50 (3H, s), 2.78 (2H, t, J=7 Hz), 5.43 (2H, s), 6.11 (1H, d, J=4 Hz), 6.60 (1H, d, J=4 Hz), 6.90 (2H, d, J=8 Hz), 7.00 (2H, d, J=8 Hz), 7.03 (1H, d, J=5 Hz), 8.03 (1H, d, J=5 Hz)

EXAMPLE 24

A mixture of trimethyltin azide (315 mg) and 2-cyano-4-difluoromethyl-1-pyrrolyl)benzyl]-7-methyl-2-propyl-3H-imidazo[4,5-b]pyridine (155.3 mg) in xylene (3 ml) was stirred at 125° C. for 16 hours and concentrated in vacuo. The residue was dissolved in methanol (2 ml) and the methanolic solution was treated with aqueous 8.9N-hydrochloric acid (0.3 ml). The solution was adjusted to pH 5 with aqueous 1N sodium hydroxide solution and then concentrated in vacuo. The residue was purified by preparative thin layer chromatography to yield 3-[4-[4-formyl-2-(1H-tetrazol-5-yl)-1-pyrrolyl]benzyl]-7-methyl-2-propyl-3H-imidazo[4,5-b] pyridine (60 mg) as an amorphous solid.

NMR (CDCl$_3$, δ): 0.93 (3H, t, J=7.5 Hz), 1.63-1.87 (2H, m), 2.57 (3H, s), 2.82 (2H, t, J-7.5 Hz), 5.54 (2H, s), 6.90 (1H, d, J=1 Hz), 7.09 (1H, d, J=5 Hz), 7.17 (2H, d, J=8 Hz), 7.25 (2H, d, J=8 Hz), 7.93 (1H, d, J=1 Hz), 8.16 (1H, d, J=5 Hz), 9.78 (1H, s)

EXAMPLE 25

The following compound was obtained according to similar manners to those of Preparation 55 and Example 3, successively.

Sodium salt of 3-[4-[4-hydroxymethyl-2-(1H-tetrazol-5-yl)-1-pyrrolyl]benzyl]-7-methyl-2-propyl-3H-imidazo[4,5-b]pyridine NMR (D$_2$O, δ): 0.81 (3H, t, J=7.5 Hz), 1.44-1.68 (2H, m), 2.56 (3H, s), 2.76 (2H, t, J=7.5 Hz), 4.56 (2H, s), 5.44 (2H, s), 6.72 (1H, d, J=1 Hz), 6.76-6.94 (5H, m), 7.09 (1H, d, J=5 Hz), 8.03 (1H, d, J=5 Hz)

EXAMPLE 26

To a suspension of 3-[4-[4-chloro-2-(1H-tetrazol-5-yl)-1-pyrrolyl]benzyl]-7-methyl-2-propyl-3H-imidazo[4,5-b]pyridine (10.33 g) in ethanol (100 ml) was added concentrated hydrochloric acid (10 ml) and ethanol (200 ml). The mixture was heated to 40°-50° C. in a water bath. The resulting solution was concentrated to half volume under reduced pressure. The precipitates were collected by filtration, washed with ethanol (50 ml) and dried over phosphorus pentoxide to yield 3-[4-[4-chloro-2-(1H-tetrazol-5-yl)-1-pyrrolyl]benzyl]-7-methyl-2-propyl-3H-imidazo[4,5-b]pyridine hydrochloride (7.70 g) as a cream powder.

mp: 140°-143° C.

NMR (DMSO-d$_6$, δ): 0.98 (3H, t, J=7.5 Hz), 1.76 (2H, m), 2.71 (3H, s), 3.19 (2H, t, J=7.5 Hz), 5.78 (2H, s), 7.02 (1H, d, J=1 Hz), 7.29 and 7.40 (4H, ABq, J=8.5 Hz), 7.42-7.48 (3H, m), 8.48 (1H, d, J=5 Hz)

EXAMPLE 27

The following compounds were obtained according to a similar manner to that of Example 1.

(1)

7-Methyl-2-propyl-3-[4-[2-(1H-tetrazol-5-yl)-4-trifluoromethyl-1-pyrrolyl]benzyl]-3H-imiazo[4,5-b]piridine NMR (DMSO-d$_6$, δ): 0.96 (3H, t, J=7 Hz), 1.76 (2H, dt, J=7 Hz, 7 Hz), 2.57 (3H, s), 2.85 (2H, t, J=7 Hz), 5.57 (2H, s), 7.08 (1H, s), 7.21 (2H, d, J=8 Hz), 7.31 (2H, d, J=8 Hz), 7.85 (1H, s), 8.18 (1H, d, J=5 Hz)

(2)

5,7-Dimethyl-3-[4-[2-methyl-5-(1H-tetrazol-5-yl)-1-pyrrolyl]benzyl]-2-propyl-3H-imidzo[4,5-b]pyridine mp: 242°-243° C.

NMR (DMSO-d$_6$, δ): 0.88 (3H, t, J=7 Hz), 1.65 (2H, dt, J=7 Hz, 7 Hz), 2.00 (3H, s), 2.52 (3H, s), 2.53 (3H, s), 2.76 (2H, t, J=7 Hz), 5.56 (2H, s), 6.18 (1H, d, J=4 Hz), 6.80 (1H, d, J=4 Hz), 6.97 (1H, s), 7.21 (4H, s)

(3)

3-[4-[2,3-Dimethyl-5-(1H-tetrazol-5-yl)-1-pyrrolyl]benzyl]-7-methyl-2-propyl-3H-imidazo[4,5-b]pyridine mp: 212°-215° C.

NMR (DMSO-d$_6$, δ): 0.90 (3H, t, J=7.5 Hz), 1.58-1.80 (2H, m), 1.91 (3H, s), 2.06 (3H, s), 2.57 (3H, s), 2.82 (2H, t, J=7.5 Hz), 5.60 (2H, s), 6.70 (1H, s), 7.10 (1H, d, J=5.0 Hz), 7.18 (2H, d, J=9.0 Hz), 7.24 (2H, d, J=9.0 Hz), 8.20 (1H, d, J=5.0 Hz)

(4)

3-[4-[2-Chloro-3-methyl-5-(1H-tetrazol-5-yl)-1-pyrrolyl]benzyl]-7-methyl-2-propyl-3H-imidazo[4,5-b]pyridine mp: 213°-215° C.

NMR (DMSO-d$_6$, δ): 0.90 (3H, t, J=7.5 Hz), 1.59-1.81 (2H, m), 2.10 (3H, s), 2.57 (3H, s), 2.82 (2H, t, J=7.5 Hz), 5.60 (2H, s), 6.85 (1H, s), 7.10 (1H, d, J=5.0 Hz), 7.23 (4H, s), 8.18 (1H, d, J=5.0 Hz)

(5)

3-[4-[2-Bromo-3-methyl-5-(1H-tetrazol-5-yl)-1-pyrrolyl]benzyl]-7-methyl-2-propyl-3H-imidazo[4,5-b]pyridine mp: 214°-216° C.

NMR (DMSO-d$_6$, δ): 0.90 (3H, t, J=7.5 Hz), 1.58-1.80 (2H, m), 2.08 (3H, s), 2.57 (3H, s), 2.81 (2H, t, J=7.5 Hz), 5.60 (2H, s), 6.85 (1H, s), 7.11 (1H, d, J=5 Hz), 7.16-7.30 (4H, m), 8.19 (1H, d, J=5 Hz)

(6)

2-Ethyl-5,7-dimethyl-3-[4-[5-methyl-2-(1H-tetrazol-5-yl)-1-pyrrolyl]benzyl]-3H-imidazo[4,5-b]pyridine mp: 261°-263° C.

NMR (DMSO-d$_6$, δ): 1.20 (3H, t, J=7 Hz), 2.00 (3H, s), 2.52 (3H x 2, s), 2.79 (2H, q, J=7 Hz), 5.55 (2H, s), 6.18 (1H, d, J=4 Hz), 6.81 (1H, d, J=4 Hz), 6.96 (1H, s), 7.20 (4H, s)

(7)

3-[4-[4-Chloro-2-(1H-tetrazol-5-yl)-1-pyrrolyl]benzyl]-2-ethyl-7-methyl-3H-imidazo[4,5-b]pyridine mp: 210°-213° C.

NMR (DMSO-d$_6$, δ): 1.29 (3H, t, J=8 Hz), 2.57 (3H, s), 2.87 (2H, t, J=8 Hz), 5.53 (2H, s), 6.89 (1H, d, J=2 Hz), 7.09 (1H, d, J=4 Hz), 7.20 (2H, d, J=7 Hz), 7.24 (2H, d, J=7 Hz), 7.46 (1H, d, J=2 Hz), 8.18 (1H, d, J=4 Hz)

(8)

3-[4-[4-Chloro-2-(1H-tetrazol-5-yl)-1-pyrrolyl]benzyl]-3H-imidazo[4,5-b]pyridine NMR (DMSO-d$_6$, δ): 0.96 (3H, t, J=7.5 Hz), 1.65-1.88 (2H, m), 2.85 (2H, t, J=7.5 Hz), 5.59 (2H, s), 6.89 (1H, d, J=1 Hz), 7.15-7.32 (5H, m), 7.45 (1H, d, J=1 Hz), 8.03 (1H, dd, J=8 Hz, 1 Hz), 8.32 (1H, dd, J=5 Hz, 1 Hz)

(9)

3-[4-(4-Chloro-2-(1H-tetrazol-5-yl)-1-pyrrolyl]benzyl]-5,7-dimethyl-2-propyl-3H-imidazo[4,5-b]pyridine mp: 217°-219° C.

NMR (DMSO-d$_6$, δ): 0.93 (3H, t, J=7.5 Hz), 1.60-1.82 (2H, m), 2.5 (6H), 2.76 (2H, t, J=7.5 Hz), 5.51 (2H, s), 6.90 (1H, d, J=1 Hz), 6.96 (1H, s), 7.15 (2H, d, J=9 Hz), 7.25 (2H, d, J=9 Hz), 7.45 (1H, d, J=1 Hz)

(10)

3-[4-[2-Chloro-1-methyl-4-(1H-tetrazol-5-yl)-3-pyrrolyl]benzyl]-7-methyl-2-propyl-3H-imidazo[4,5-b]pyridine NMR (DMSO-d$_6$, δ): 0.94 (3H, t, J=7.5 Hz), 1.63-1.85 (2H, m), 2.56 (3H, s), 2.81 (2H, t, J=7.5 Hz), 3.69 (3H, s), 5.51 (2H, s), 7.04-7.28 (5H, m), 7.50 (1H, s), 8.17 (1H, d, J=5 Hz)

(11)

3-[4-[5-Bromo-1-ethyl-3-(1H-tetrazol-5-yl)-2-pyrrolyl]benzyl]-7-methyl-2-propyl-3H-imidazo[4,5-b]pyridine NMR (DMSO-d$_6$, δ): 0.89 (3H, t, J=8 Hz), 1.04 (3H, t, J=8 Hz), 1.66 (2H, m), 2.56 (3H, s), 2.81 (2H, t, J=8 Hz), 3.78 (2H, t, J=8 Hz), 5.59 (2H, s), 6.76 (1H, s), 7.08 (1H, d, J=4 Hz), 7.21 (2H, d, J=7 Hz), 7.32 (2H, d, J=7 Hz), 8.18 (1H, d, J=4 Hz)

(12)
3-[4-[1-Ethyl-3-(1H-tetrazol-5-yl)-2-pyrrolyl]benzyl]-7-methyl-2-propyl-3H-imidazo[4,5-b]pyridine NMR (CDCl$_3$-CD$_3$OD, δ): 0.96 (3H, t, J=7 Hz), 1.20 (3H, t, J=7 Hz), 1.75 (2H, m), 2.64 (3H, s), 2.88 (2H, t, J=7 Hz), 3.78 (2H, t, J=7 Hz), 5.58 (2H, s), 6.62 (1H, d, J=2 Hz), 6.86 (1H, d, J=2 Hz), 7.11 (1H, d, J=5 Hz), 7.17 (2H, d, J=7 Hz), 7.26 (2H, d, J=7 Hz), 8.18 (1H, d, J=5 Hz)

EXAMPLE 28

Sodium hydride (10 mg) (60% in oil) was added to a stirred solution of 2-butyl-7-methylimidazo[4,5-b]pyridine (48 mg) in dimethyl sulfoxide (5.0 ml) and the mixture was stirred for 30 minutes at ambient temperature. To this mixture was added a solution of 4-ethoxycarbonyl-1-(4-methanesulfonyloxymethylphenyl)-2-(1-trityl-1H-tetrazol-5-yl)pyrrole (193 mg) in dimethyl sulfoxide (2 ml). The mixture was stirred for 3 hours at ambient temperature and poured into brine. The mixture was extracted with ethyl acetate, dried over magnesium sulfate and evaporated in vacuo. The residue was purified by preparative thin layer chromatography to afford 2-butyl-3-[4-[4-ethoxycarbonyl-2-(1-trityl-1H-tetrazol-5-yl)-1-pyrrolyl]benzyl]-7-methyl-3H-imidazo[4,5-b]pyridine (123 mg) as a colorless viscous oil.

NMR (CDCl$_3$, δ): 0.88 (3H, t, J=8 Hz), 1.36 (3H, t, J=8 Hz), 1.24-1.41 (2H, m), 1.71 (2H, m), 2.70 (3H, s), 2.74 (2H, t, J=8 Hz), 4.30 (2H, q, J=8 Hz), 5.44 (2H, s), 6.86-7.35 (20H, m), 7.40 (1H, d, J=1.5 Hz), 7.48 (1H, d, J=1.5 Hz), 8.20 (1H, d, J=8 Hz)

EXAMPLE 29

A mixture of 2-butyl-3-[4-[4-ethoxycarbonyl-2-(1-trityl-1H-tetrazol-5-yl)-1-pyrrolyl]benzyl]-7-methyl-3H-imidazo[4,5-b]pyridine (115 mg), conc. hydrochloric acid (0.25 ml) and methanol (20 ml) was stirred for 2 hours and concentrated under reduced pressure. The residue was purified by preparative thin layer chromatography to give 2-butyl-3-[4-[4-ethoxycarbonyl-2-(1H-tetrazol-5-yl)-1-pyrrolyl]benzyl]-7-methyl-3H-imidazo[4,5-b]pyridine [53 mg] as a colorless viscous oil.

NMR (CDCl$_3$-CD$_3$OD, δ): 0.93 (3H, t, J=8 Hz), 1.36 (3H, t, J=8 Hz), 1.42 (2H, m), 1.73 (2H, m), 2.69 (3H, s), 2.90 (2H, t, J=8 Hz), 4.31 (2H, t, J=8 Hz), 5.60 (2H, s), 7.14 (1H, d, J=8 Hz), 7.17-7.31 (6H, m), 8.18 (1H, d, J=8 Hz)

EXAMPLE 30

The following compounds were obtained according to a similar manner to that of Example 3.

(1) Sodium salt of
7-methyl-2-propyl-3-[4-[2-(1H-tetrazol-5-yl)-4-trifluoromethyl-1-pyrrolyl]benzyl]-3H-imidazo[4,5-b]pyridine NMR (D$_2$O, δ): 0.56 (3H, t, J=7 Hz), 1.39 (2H, dt, J=7.7 Hz), 2.35 (3H, s), 2.56 (2H, t, J=7 Hz), 5.21 (2H, s), 6.57 (2H, d, J=8 Hz), 6.67-6.83 (5H, m), 7.79 (1H, d, J=8 Hz)

(2) Sodium salt of
5,7-dimethyl-3-[4-[2-methyl-5-(1H-tetrazol-5-yl)-1-pyrrolyl]benzyl]-2-propyl-3H-imidazo[4,5-b]pyridine NMR (D$_2$O, δ): 0.69 (3H, t, J=7 Hz), 1.37 (2H, m), 1.80 (3H, s), 2.37 (6H, s), 2.67 (2H, t, J=7 Hz), 5.34 (2H, s), 6.07 (1H, d, J=4 Hz), 6.60 (1H, d, J=4 Hz), 6.71 (1H, s), 6.84 (2H, d, J=8 Hz), 6.96 (2H, d, J=8 Hz)

(3) Sodium salt of
3-[4-[2,3-dimethyl-5-(1H-tetrazol-5-yl)-1-pyrrolyl]benzyl]-7-methyl-2-propyl-3H-imidazo[4,5-b]pyridine mp: 123°-129.5° C.

NMR (D$_2$O, δ): 0.63 (3H, t, J=7.5 Hz), 1.22-1.52 (2H, m), 1.45 (3H, s), 1.82 (3H, s), 2.35 (3H, s), 2.65 (2H, t, J=7.5 Hz), 5.30 (2H, s), 6.48 (1H, s), 6.65 (2H, d, J=9.0 Hz), 6.77 (1H, d, J=5.0 Hz), 6.88 (2H, d, J=9.0 Hz), 7.87 (1H, d, J=5.0 Hz)

(4) Sodium salt of
3-[4-[2-chloro-3-methyl-5-(1H-tetrazol-5-yl)-1-pyrrolyl]benzyl]-7-methyl-2-propyl-3H-imidazo[4,5-b]pyridine NMR (D$_2$O, δ): 0.48 (3H, t, J=7.5 Hz), 1.12-1.39 (2H, m), 1.60 (3H, s), 2.26 (3H, s), 2.51 (2H, t, J=7.5 Hz), 5.21 (2H, s), 6.46 (1H, s), 6.58-6.71 (3H, m), 6.83 (2H, d, J=9.0 Hz), 7.81 (1H, d, J=5.0 Hz)

(5) Sodium salt of
3-[4-(2-bromo-3-methyl-5-(1H-tetrazol-5-yl)-1-pyrrolyl]benzyl]-7-methyl-2-propyl-3H-imidazo[4,5-b]pyridine NMR (D$_2$O, δ): 0.50 (3H, t, J=7.5 Hz), 1.10-1.49 (2H, m), 1.62 (3H, s), 2.26 (3H, s), 2.50 (2H, t, J=7.5 Hz), 5.22 (2H, s), 6.50 (1H, s), 6.57-6.72 (3H, m), 6.83 (2H, d, J=9 Hz), 7.83 (1H, d, J=5 Hz)

(6) Sodium salt of
2-ethyl-5,7-dimethyl-3-[4-[2-methyl-5-(1H-tetrazol-5-yl)-1-pyrrolyl]benzyl]-3H-imidazo[4,5-b]pyridine mp: 177°-181° C.

NMR (D$_2$O, δ): 1.00 (3H, t, J=7 Hz), 1.63 (3H, s), 2.26 (3H x 2, s), 2.65 (2H, q, J=7 Hz), 5.76 (2H, s), 5.96 (1H, d, J=3 Hz), 6.46 (1H, s), 6.59 (1H, d, J=3 Hz), 6.72 (2H, d, J=8 Hz), 6.90 (2H, d, J=8 Hz)

(7) Sodium salt of
3-[4-[4-chloro-2-(1H-tetrazol-5-yl)-1-pyrrolyl]benzyl]-2-ethyl-7-methyl-3H-imidazo[4,5-b]pyridine NMR (D$_2$O, δ): 1.11 (3H, t, J=7.5 Hz), 2.43 (3H, s), 2.70 (2H, q, J=7.5 Hz), 5.30 (2H, s), 6.44 (1H, d, J=2 Hz), 6.51-6.63 (3H, m), 6.78 (2H, d, J=9 Hz), 6.89 (1H, d, J=5 Hz), 7.88 (1H, d, J=5 Hz)

(8) Sodium salt of
3-[4-[4-chloro-2-(1H-tetrazol-5-yl)-1-pyrrolyl]benzyl]-2-propyl-3H-imidazo[4,5-b]pyridine NMR (D$_2$O, δ): 0.80 (3H, t, J=7.5 Hz), 1.45-1.71 (2H, m), 2.70 (2H, t, J=7.5 Hz), 5.40 (2H, s), 6.56-6.76 (4H, m), 6.86 (2H, d, J=9 Hz), 7.22 (1H, dd, J=8 Hz, 5 Hz), 7.95 (1H, dd, J=8 Hz, 1 Hz), 8.14 (1H, dd, J=5 Hz, 1 Hz)

(9) Sodium salt of
3-[4-[4-Chloro-2-(1H-tetrazol-5-yl)-1-pyrrolyl]benzyl]-5,7-dimethyl-2-propyl-3H-imidazo[4,5-b]pyridine NMR (D$_2$O, δ): 0.73 (3H, t, J=7.5 Hz), 1.34-1.59 (2H, m), 2.33 (3H, s), 2.37 (3H, s), 2.64 (2H, t, J=7.5

Hz), 5.30 (2H, s), 6.43 (1H, d, J=1 Hz), 6.50–6.72 (4H, m), 6.80 (2H, d, J=9 Hz)

(10) Sodium salt of 2-butyl-3-[4-[4-ethoxycarbonyl-2-(1H-tetrazol-5-yl)-1-pyrrolyl]benzyl]-7-methyl-3H-imidazo[4,5-b]pyridine NMR (D$_2$O, δ): 0.68 (3H, t, J=8 Hz), 1.17 (2H, t, J=8 Hz), 1.15 (2H, m), 1.43 (2H, m), 2.44 (3H, s), 2.64 (2H, t, J=8 Hz), 4.11 (2H, q, J=8 Hz), 5.31 (2H, s), 6.71 (2H, d, J=8 Hz), 6.88 (2H, d, J=8 Hz), 6.90 (1H, d, J=5 Hz), 6.96 (1H, d, J=1.5 Hz), 6.98 (1H, d, J=1.5 Hz), 7.90 (1H, d, J=5 Hz)

(11) Sodium salt of 3-[4-[2-chloro-1-methyl-4-(1H-tetrazol-5-yl)-3-pyrrolyl]benzyl]-7-methyl-2-propyl-3H-imidazo[4,5-b]pyridine NMR (D$_2$O, δ): 0.70 (3H, t, J=7.5 Hz), 1.33–1.58 (2H, m), 2.37 (3H, s), 2.62 (2H, t, J=7.5 Hz), 3.33 (3H, s), 6.74–6.93 (5H, m), 7.07 (1H, s), 7.93 (1H, d, J=5 Hz)

(12) Sodium salt of 3-[4-[5-bromo-1-ethyl-3-(1H-tetrazol-5-yl)-2-pyrrolyl]benzyl]-7-methyl-2-propyl-3H-imidazo[4,5-b]pyridine NMR (D$_2$O, δ): 0.45 (3H, t, J=7 Hz), 0.58 (3H, t, J=7 Hz), 1.35 (2H, m), 2.30 (3H, s), 2.63 (2H, t, J=7 Hz), 3.20 (2H, m), 5.30 (2H, s), 6.56 (1H, s), 6.71 (1H, d, J=4 Hz), 6.79 (2H, d, J=7 Hz), 6.95 (2H, d, J=7 Hz), 7.83 (1H, d, J=4 Hz)

(13) Sodium salt of 3-[4-[1-ethyl-3-(1H-tetrazol-5-yl)-2-pyrrolyl]benzyl]-7-methyl-2-propyl-3H-imidazo[4,5-b]pyridine NMR (D$_2$O, δ): 0.65 (3H, t, J=7 Hz), 0.73 (3H, t, J=7 Hz), 1.35 (2H, m), 2.32 (3H, s), 2.65 (2H, t, J=7 Hz), 3.34 (2H, q, J=7 Hz), 5.28 (2H, s), 6.57 (1H, d, J=1 Hz), 6.75 (1H, d, J=1 Hz), 6.76 (1H, d, J=5 Hz), 6.82 (2H, d, J=8 Hz), 6.89 (2H, d, J=8 Hz), 7.83 (1H, d, J=5 Hz)

EXAMPLE 31

7-Methyl-3-[4-[5-methyl-2-(1H-tetrazol-5-yl)-1-pyrrolyl]benzyl]-2-propyl-3H-imidazo[4,5-b]pyridine (13.1 g) was dissolved in hot ethanol (70 ml) and conc. hydrochloric acid (3.2 ml) was added therein. The mixture was stirred for 1 hour at ambient temperature and the precipitate was collected by vacuum filtration to give a white powder (11.7 g). This was recrystallized from methanol - 1N hydrochloric acid to afford 7-methyl-3-[4-[5-methyl-2-(1H-tetrazol-5-yl)-1-pyrrolyl]benzyl]-2-propyl-3H-imidazo[4,5-b]pyridine hydrochloride (9.13 g) as colorless fine crystals.

mp: 241°–243° C.

NMR (DMSO-d$_6$, δ): 0.90 (3H, t, J=7 Hz), 1.69 (2H, m), 2.00 (3H, s), 2.70 (3H, s), 3.18 (2H, t, J=7 Hz), 5.82 (2H, s), 6.20 (1H, d, J=4 Hz), 6.88 (1H, d, J=4 Hz), 7.27 (2H, d, J=8 Hz), 7.40 (2H, d, J=8 Hz), 7.46 (1H, d, J=4 Hz), 8.50 (1H, d, J=4 Hz)

EXAMPLE 32

A mixture of 3-[4-(2-cyano-3-furyl)benzyl]-7-methyl-2-propyl-3H-imidazo[4,5-b]pyridine (540 mg) and trimethyltin azide (1.095 g) in xylene (10 ml) was stirred at 125° C. for 24 hours. The mixture was concentrated in vacuo. The residue was dissolved in methanol (15 ml) and the methanolic solution was treated with 8.9N methanolic hydrogen chloride (1 ml) for one hour at ambient temperature. The mixture was adjusted to pH 5 with aqueous 1N sodium hydroxide solution and concentrated in vacuo. The residue was purified by flash column chromatography on silica gel (elution by dichloromethane/methanol=15/1–8/1) to yield 7-methyl-2-propyl-3-[4-[2-(1H-tetrazol-5-yl)-3-furyl]benzyl]-3H-imidazo[4,5-b]pyridine (525 mg) as an amorphous solid.

NMR (DMSO-d$_6$, δ): 0.95 (3H, t, J=7.5 Hz), 1.64–1.87 (2H, m), 2.58 (3H, s), 2.83 (2H, t, J=7.5 Hz), 5.55 (2H, s), 7.00 (1H, d, J=1 Hz), 7.05 (1H, d, J=5 Hz), 7.20 (2H, d, J=9 Hz), 7.75 (2H, d, J=9 Hz), 8.02 (1H, d, J=1 Hz), 8.17 (1H, d, J=5 Hz)

EXAMPLE 33

7-Methyl-2-propyl-3-[4-[2-(1H-tetrazol-5-yl)-3-furyl]benzyl]-3H-imidazo[4,5-b]pyridine (520 mg) was dissolved in aqueous 1N sodium hydroxide solution (1.3 ml). The solution was filtered and the filtrate was lyophilized to give sodium salt of 7-methyl-2-propyl-3-[4-[2-(1H-tetrazol-5-yl)-3-furyl]benzyl]-3H-imidazo-4,5-b]pyridine (505 mg).

NMR (D$_2$O, δ): 0.75 (3H, t, J=7.5 Hz), 1.36–1.60 (2H, m), 2.40 (3H, s), 2.60 (2H, t, J=7.5 Hz), 5.21 (2H, s), 6.36 (1H, d, J=1 Hz), 6.74 (2H, d, J=9 Hz), 6.87 (1H, d, J=5 Hz), 6.98 (2H, d, J=9 Hz), 7.54 (1H, d, J=1 Hz), 7.90 (1H, d, J=5 Hz)

EXAMPLE 34

The following compounds were obtained according to a similar manner to that of Example 1.

(1) 2-Butyl-3-[4-[2-(1H-tetrazol-5-yl)-3-benzo[b]furyl]benzyl]-3H-imidazo[4,5-b]pyridine mp: 244°–248° C.

NMR (DMSO-d$_6$, δ): 0.88 (3H, t, J=7.5 Hz), 1.28–1.49 (2H, m), 1.63–1.82 (2H, m), 2.91 (2H, t, J=7.5 Hz), 5.59 (2H, s), 7.18–7.40 (5H, m), 7.58 (1H, d, J=7.5 Hz), 7.62–7.75 (1H, m), 7.69 (2H, d, J=8.0 Hz), 8.02 (1H, dd, J=9.0 Hz and 0.5 Hz), 8.33 (1H, dd, J=5.0 Hz, 0.5 Hz)

(2) 2-Butyl-3-[4-[3-(1H-tetrazol-5-yl)-2-benzo[b]thienyl]benzyl]-3H-imidazo[4,5-b]pyridine mp: 75°–77° C.

NMR (DMSO-d$_6$, δ): 0.87 (3H, t, J=7 Hz), 1.36 (2H, m), 1.71 (2H, m), 2.86 (2H, t, J=7 Hz), 5.54 (2H, s), 7.14 (2H, d, J=8 Hz), 7.20–7.50 (5H), 7.72 (1H, m), 7.98–8.10 (2H), 8.30 (1H, d, J=5 Hz)

(3) 2-Butyl-3-[4-[1-bromo-3-(1H-tetrazol-5-yl)-2-indolizinyl]benzyl]-3H-imidazo[4,5-b]pyridine NMR (CDCl$_3$-CD$_3$OD, δ): 0.93 (3H, t, J=7 Hz), 1.43 (2H, m), 1.79 (2H, m), 2.93 (2H, t, J=7 Hz), 5.64 (2H, s), 6.86 (1H, dd, J=7 Hz and 1 Hz), 7.11 (1H, dd, J=7 Hz and 8 Hz), 7.21 (2H, d, J=8 Hz), 7.32 (1H, m), 7.35 (2H, d, J=8 Hz), 7.57 (1H, d, J=8 Hz), 8.05 (1H, dd, J=8 Hz and 1 Hz), 8.36 (1H, dd, J=7 Hz and 1 Hz), 9.10 (1H, d, J=7 Hz)

(4) 2-Butyl-3-[4-[1-bromo-3-(1H-tetrazol-5-yl)-2-indolizinyl]benzyl]-3H-imidazo[4,5-b]pyridine NMR (CDCl$_3$-CD$_3$OD, δ): 0.92 (3H, t, J=7 Hz), 1.44 (2H, m), 1.86 (2H, m), 3.02 (2H, t, J=7 Hz), 5.62 (2H, s), 6.93 (1H, dd, J=7 Hz), 7.17 (1H, ddd, J=1 Hz, 7 Hz and 8 Hz), 7.24–7.45 (5H, m), 8.15 (2H, dt, J=1 Hz and 7 Hz), 8.43 (1H, dd, J=1 Hz and 5 Hz), 8.52 (1H, d, J=8 Hz)

(5)
3-[4-[2-Chloro-1-methyl-4-(1H-tetrazol-5-yl)-3-pyrrolyl]benzyl]-5,7-dimethyl-2-ethyl-3H-imidazo4,5-b]pyridine mp: 224°–226° C.
NMR (DMSO-d6, δ): 1.26 (3H, t, J=7.5 Hz), 2.52 (6H, s), 2.81 (2H, q, J=7.5 Hz), 3.69 (3H, s), 5.48 (2H, s), 6.96 (1H, s), 7.10 (2H, d, J=9 Hz), 7.21 (2H, d, J=9 Hz), 7.51 (1H, s)

(6)
3-[4-[1,2-Dimethyl-4-(1H-tetrazol-5-yl)-3-pyrrolyl]benzyl]-7-methyl-2-propyl-3H-imidazo[4,5-b]pyridine mp: 124°–130° C.
NMR (DMSO-d6, δ): 0.92 (3H, t, J=7.5 Hz), 1.61–1.83 (2H, m), 2.12 (3H, s), 2.56 (3H, s), 2.83 (2H, t, J=7.5 Hz), 3.62 (3H, s), 5.50 (2H, s), 7.03–7.18 (5H, m), 7.30 (1H, s), 8.17 (1H, d, J=5 Hz)

(7)
7-Methyl-2-propyl-3-[4-[1-propyl-3-[1H-tetrazol-5-yl)-2-pyrrolyl]benzyl]-3H-imidazo[4,5-b]pyridine NMR (DMSO-d6, δ): 0.63 (3H, t, J=8 Hz), 0.88 (3H, t, J=8 Hz), 1.45 (2H, m), 1.66 (2H, m), 2.56 (3H, s), 2.83 (2H, t, J=8 Hz), 3.72 (2H, t, J=8 Hz), 5.58 (2H, s), 6.58 (1H, d, J=4 Hz), 7.07 (1H, d, J=4 Hz), 7.09 (1H, d, J=5 Hz), 7.10 (2H, d, J=9 Hz), 7.20 (2H, d, J=9 Hz), 8.17 (1H, d, J=5 Hz)

(8)
5,7-Dimethyl-2-ethyl-3-[4-[1-ethyl-3-(1H-tetrazol-5-yl)-2-pyrrolyl]benzyl]-3H-imidazo[4,5-b]pyridine mp: 252°–254° C.
NMR (DMSO-d6, δ): 1.11 (3H, t, J=8 Hz), 1.23 (3H, t, J=8 Hz), 2.44 (3H, s), 2.47 (3H, s), 2.81 (2H, q, J=8 Hz), 3.77 (2H, q, J=8 Hz), 5.51 (2H, s), 6.58 (1H, d, J=3 Hz), 6.95 (1H, s), 7.10 (1H, d, J=3 Hz), 7.19 (2H, d, J=9 Hz), 7.31 (2H, d, J=9 Hz)

(9)
3-[4-[1-Isopropyl-3-(1H-tetrazol-5-yl)-2-pyrrolyl]benzyl]-7-methyl-2-propyl-3H-imidazo[4,5-b]pyridine NMR (DMSO-d6, δ): 0.90 (3H, t, J=8 Hz), 1.28 (6H, d, J=8 Hz), 1.70 (2H, m), 2.56 (3H, s), 2.82 (2H, t, J=8 Hz), 4.07 (1H, m), 5.57 (2H, s), 6.61 (1H, d, J=3 Hz), 7.09 (1H, d, J=5 Hz), 7.19 (1H, d, J=3 Hz), 7.22 (2H, d, J=9 Hz), 7.29 (2H, d, J=9 Hz), 8.17 (1H, d, J=5 Hz)

(10)
3-[4-[2-Chloro-1-methyl-4-(1H-tetrazol-5-yl)-3-pyrrolyl]benzyl]-5,7-dimethyl-2-propyl-3H-imidazo[4,5-b]pyridine mp: 147°–150° C.
NMR (DMSO-d6, δ): 0.91 (3H, t, J=7.5 Hz), 1.60–1.81 (2H, m), 2.51 (6H, s), 2.77 (2H, t, J=7.5 Hz), 3.70 (3H, s), 5.48 (2H, s), 6.96 (1H, s), 7.10 (2H, d, J=9 Hz), 7.21 (2H, d, J=9 Hz), 7.51 (1H, s)

(11)
5,7-Dimethyl-3-[4-[1-ethyl-3-(1H-tetrazol-5-yl)-2-pyrrolyl]benzyl]-2-propyl-3H-imidazo[4,5-b]pyridine mp: 209°–212° C.

NMR (DMSO-d6, δ): 0.86 (3H, t, J=8 Hz), 1.11 (3H, t, J=8 Hz), 1.68 (2H, m), 2.50 (3H, s), 2.53 (3H, s), 2.75 (2H, t, J=8 Hz), 3.78 (2H, q, J=8 Hz), 5.55 (2H, s), 6.60 (1H, d, J=3 Hz), 6.98 (1H, s), 7.10 (1H, d, J=3 Hz), 7.17 (2H, d, J=9 Hz), 7.31 (2H, d, J=9 Hz)

EXAMPLE 35

The following compounds were obtained according to a similar manner to that of Example 28.

(1)
2-Butyl-3-[4-[5-chloro-2-(1-trityl-1H-tetrazol-5-yl)-3-thienyl]benzyl]-3H-imidazo[4,5-b]pyridine NMR (CDCl3, δ): 0.88 (3H, t, J=6 Hz), 1.38 (2H, m), 1.79 (2H, m), 2.85 (2H, t, J=6 Hz), 5.52 (2H, s), 6.90–7.40 (21H), 8.14 (1H, d, J=8 Hz), 8.43 (1H, dd, J=5 Hz and 1 Hz)

(2)
2-Butyl-3-[4-[3-(1-trityl-1H-tetrazol-5-yl)-2-imidazo[1,2-a]pyridyl]benzyl]-3H-imdazo[4,5-b]pyridine NMR (CDCl3, δ): 0.88 (1.5H, t, J=7 Hz), 0.97 (1.5H, t, J=7 Hz), 1.18–1.60 (2H, m), 1.68–2.03 (2H, m), 2.76 (1H, t, J=7 Hz), 3.05 (1H, t, J=7 Hz), 5.52 (2H, s), 6.91 (1H, dd, J=1 Hz and 7 Hz), 7.06–7.63 (18H, m), 7.73 (1H, t, J=7 Hz), 7.83 (2H, d, J=8 Hz), 8.07 (2H, d, J=8 Hz), 8.88 (1H, dd, J=1 Hz and 8 Hz), 9.09 (1H, d, J=8 Hz)

EXAMPLE 36

The following compound was obtained according to a similar manner to that of Example 29.

2-Butyl-3-[4-[3-(1H-tetrazol-5-yl)-2-imidazo[1,2-a]pyridyl]benzyl]-3H-imidazo[4,5-b]pyridine NMR (CD3OD, δ): 0.80 (3H, t, J=7 Hz), 1.30 (2H, m), 1.66 (2H, m), 2.74 (2H, t, J=7 Hz), 5.45 (2H, s), 6.86 (1H, t, J=7 Hz), 7.04 (2H, d, J=8 Hz), 7.18 (1H, d, J=5 Hz), 7.23 (1H, d, J=5 Hz), 7.31 (1H, br t, J=8 Hz), 7.62 (2H, d, J=8 Hz), 7.93 (1H, dd, J=1 Hz and 8 Hz), 8.24 (1H, dd, J=1 Hz and 7 Hz), 8.40 (1H, d, J=8 Hz)

EXAMPLE 37

2-Butyl-3-[4-[5-chloro-2-(1-trityl-1H-tetrazol-5-yl)-3-thienyl]benzyl]-3H-imidazo[4,5-b]pyridine (1.02 g) was dissolved in 1,4-dioxane (10 ml) and treated with 1N hydrochloric acid at ambient temperature for 10 hours. The reaction mixture was neutralized with 1N aqueous sodium hydroxide and concentrated in vacuo. The residue was extracted with dichloromethane-methanol (4:1) and the extract was evaporated in vacuo. The residue was purified by silica gel column chromatography to afford 2-butyl-3-[4-[5-chloro-2-(1H-tetrazol-5-yl)-3-thienyl]benzyl]-3H-imidazo[4,5-b]pyridine (640 mg).

NMR (DMSO-d6, δ): 0.87 (3H, t, J=6 Hz), 1.37 (2H, m), 1.72 (2H, m), 2.86 (2H, t, J=6 Hz), 5.54 (2H, s), 7.16 (2H, d, J=8 Hz), 7.27 (1H, dd, J=8 Hz and 5 Hz), 7.40 (2H, d, J=8 Hz), 8.02 (1H, dd, J=8 Hz and 1 Hz), 8.30 (1H, dd, J=5 Hz and 1 Hz)

EXAMPLE 38

The following compounds were obtained according to a similar manner to that of Example 3.

(1) Sodium salt of
3-[4-[2-chloro-1-methyl-4-(1H-tetrazol-5-yl)-3-pyrrolyl]benzyl]-5,7-dimethyl-2-ethyl-3H-imidazo[4,5-b]pyridine mp: 107°–112° C.

NMR (D₂O, δ): 1.00 (3H, t, J=7.5 Hz), 2.19 (3H, s), 2.23 (3H, s), 2.55 (2H, q, J=7.5 Hz), 3.20 (3H, s), 5.19 (2H, s), 6.48 (1H, s), 6.66–6.84 (4H, m), 7.00 (1H, s)

(2) Sodium salt of
3-[4-[1,2-dimethyl-4-(1H-tetrazol-5-yl)-3-pyrrolyl]benzyl]-7-methyl-2-propyl-3H-imidazo[4,5-b]pyridine NMR (D₂O, δ): 0.78 (3H, t, J=7.5 Hz), 1.40–1.62 (2H, m), 1.78 (3H, s), 2.46 (3H, s), 2.71 (2H, t, J=7.5 Hz), 3.45 (3H, s), 5.35 (2H, s), 6.73 (2H, d, J=9 Hz), 6.85 (2H, d, J=9 Hz), 6.97 (1H, d, J=5 Hz), 7.07 (1H, s), 7.98 (1H, d, J=5 Hz)

(3) Sodium salt of
7-methyl-2-propyl-3-[4-[1-propyl-3-(1H-tetrazol-5-yl)-2-pyrrolyl]benzyl]-3H-imidazo[4,5-b]pyridine NMR (D₂O, δ): 0.28 (3H, t, J=8 Hz), 0.62 (3H, t, J=8 Hz), 1.07 (2H, m), 1.34 (2H, m), 2.37 (3H, s), 2.65 (2H, t, J=8 Hz), 3.28 (2H, t, J=8 Hz), 5.33 (2H, s), 6.53 (1H, d, J=3 Hz), 6.68 (1H, d, J=3 Hz), 6.78 (1H, d, J=5 Hz), 6.89 (2H, d, J=9 Hz), 6.94 (2H, d, J=9 Hz), 7.90 (1H, d, J=5 Hz)

(4) Sodium salt of
5,7-dimethyl-2-ethyl-3-[4-[1-ethyl-3-(1H-tetrazol-5-yl)-2-pyrrolyl]benzyl]-3H-imidazo[4,5-b]pyridine NMR (D₂O, δ): 0.78 (3H, t, J=8 Hz), 1.05 (3H, t, J=8 Hz), 2.29 (6H, s), 2.67 (2H, q, J=8 Hz), 3.40 (2H, q, J=8 Hz), 5.79 (2H, s), 6.55 (1H, d, J=3 Hz), 6.56 (1H, s), 6.78 (1H, d, J=3 Hz), 6.86 (2H, d, J=9 Hz), 6.91 (2H, d, J=9 Hz)

(5) Sodium salt of
3-[4-[1-isopropyl-3-(1H-tetrazol-5-yl)-2-pyrrolyl]benzyl]-7-methyl-2-propyl-3H-imidazo[4,5-b]pyridine NMR (D₂O, δ): 0.68 (3H, t, J=8 Hz), 0.92 (6H, d, J=7 Hz), 1.40 (2H, m), 2.39 (3H, s), 2.69 (2H, t, J=7 Hz), 3.82 (1H, m), 5.34 (2H, s), 6.56 (1H, d, J=3 Hz), 6.84 (1H, d, J=5 Hz), 6.85 (1H, d, J=3 Hz), 6.91 (2H, d, J=9 Hz), 6.98 (2H, d, J=9 Hz), 7.90 (1H, d, J=5 Hz)

(6) Sodium salt of
5,7-dimethyl-3-[4-[1-ethyl-3-(1H-tetrazol-5-yl)-2-pyrrolyl]benzyl]-2-propyl-3H-imidazo[4,5-b]pyridine NMR (D₂O, δ): 0.64 (3H, t, J=8 Hz), 0.80 (3H, t, J=8 Hz), 1.35 (2H, m), 2.27 (3H, s), 2.31 (3H, s), 2.63 (2H, t, J=8 Hz), 3.45 (2H, q, J=8 Hz), 5.82 (2H, s), 6.56 (1H, d, J=3 Hz), 6.61 (1H, s), 6.79 (1H, d, J=3 Hz), 6.89 (2H, d, J=9 Hz), 6.94 (2H, d, J=9 Hz)

EXAMPLE 38

A mixture of 2-butyl-3-[4-[5-chloro-2-(1H-tetrazol-5-yl)-3-thienyl]benzyl]-3H-imidazo[4,5-b]pyridine (330 mg), 10% palladium on carbon (103 mg), potassium hydroxide (261 mg) and methanol (15 ml) was stirred under hydrogen atmosphere (1 atm) at ambient temperature for 3 hours. The reaction mixture was filtered through cellulose powder and the filtrate was evaporated in vacuo. The residue was dissolved in water and neutralized with 1N hydrochloric acid. The precipitate was collected by vacuum filtration to afford a white powder of 2-butyl-3-[4-[2-(1H-tetrazol-5-yl)-3-thienyl]benzyl]-3H-imidazo[4,5-b]pyridine (279 mg).

NMR (DMSO-d₆, δ): 0.88 (3H, t, J=6 Hz), 1.37 (2H, m), 1.71 (2H, m), 2.88 (2H, t, J=6 Hz), 5.56 (2H, s), 7.19 (2H, d, J=8 Hz), 7.24–7.40 (4H), 7.94 (1H, d, J=5 Hz), 8.03 (1H, dd, J=8 Hz and 1 Hz), 8.32 (1H, dd, J=5 Hz and 1 Hz)

EXAMPLE 40

The following compounds were obtained according to a similar manner to that of Example 39.

(1)
2-Butyl-3-[4-[3-(1H-tetrazol-5-yl)-2-indolizinyl]benzyl]-3H-imidazo[4,5-b]pyridine mp: 152°–154° C.

NMR (CDCl₃-CD₃OD, Δ): 0.96 (3H, t, J=7 Hz), 1.45 (2H, m), 1.80 (2H, m), 2.92 (2H, t, J=7 Hz), 5.60 (2H, s), 6.66 (1H, s), 6.78 (1H, dt, J=1 Hz and 7 Hz), 6.98 (1H, ddd, J=1 Hz, 7 Hz and 8 Hz), 7.18 (2H, d, J=7 Hz), 7.34 (2H, d, J=7 Hz), 7.35 (1H, m), 8.05 (1H, dd, J=8 Hz and 1 Hz), 8.35 (1H, dd, J=1 Hz and 7 Hz), 8.93 (1H, d, J=8 Hz)

(2)
2-Butyl-3-[4-[1-(1H-tetrazol-5-yl)-2-indolizinyl]benzyl]-3H-imidazo[4,5-b]pyridine mp: 183°–185° C.

NMR (CDCl₃-CD₃OD, δ): 0.93 (3H, t, J=7 Hz), 1.43 (2H, m), 1.79 (2H, m), 2.97 (2H, t, J=7 Hz), 5.63 (2H, s), 6.74 (1H, t, J=7 Hz), 7.03 (1H, dd, J=7 Hz and 8 Hz), 7.18 (2H, d, J=7 Hz), 7.29 (1H, s), 7.40 (1H, m), 7.50 (2H, d, J=7 Hz), 7.91 (1H, d, J=8 Hz), 8.10 (2H, d, J=7 Hz), 8.43 (1H, d, J=5 Hz)

EXAMPLE 41

The following compounds were obtained according to a similar manner to that of Example 1.

(1)
3-[4-[5-Chloro-1-ethyl-3-(1H-tetrazol-5-yl)-2-pyrrolyl]benzyl]-7-methyl-2-propyl-3H-imidazo[4,5-b]pyridine mp: 213°–214° C.

NMR (CDCl₃-CD₃OD, δ): 1.01 (3H, t, J=7 Hz), 1.18 (3H, t, J=7 Hz), 1.80 (2H, m), 2.71 (3H, s), 2.95 (2H, t, J=7 Hz), 3.89 (2H, q, J=7 Hz), 5.63 (2H, s), 6.60 (1H, s), 7.15 (1H, d, J=5 Hz), 7.22 (2H, d, J=9 Hz), 7.30 (2H, d, J=9 Hz), 7.49 (1H, s), 8.23 (1H, d, J=5 Hz)

(2)
3-[4-[5-Chloro-1-methyl-3-(1H-tetrazol-5-yl)-2-pyrrolyl]benzyl]-7-methyl-2-propyl-3H-imidazo[4,5-b]pyridine mp: 190°–191° C.

NMR (DMSO-d₆, δ): 0.93 (3H, t, J=7 Hz), 1.72 (2H, m), 2.57 (3H, s), 2.84 (2H, d, J=7 Hz), 3.37 (3H, s), 5.58 (2H, s), 6.67 (1H, s), 7.10 (1H, d, J=5 Hz), 7.22 (2H, d, J=9 Hz), 7.37 (2H, d, J=9 Hz), 8.18 (1H, d, J=5 Hz)

(3)
3-[4-[5-Chloro-1-ethyl-3-(1H-tetrazol-5-yl)-2-pyrrolyl]benzyl]-2-ethyl-5,7-dimethyl-3H-imidazo[4,5-b]pyridine mp: 254°–261° C. (dec.)

NMR (CDCl₃-CD₃OD, δ): 1.17 (3H, t, J=7.5 Hz), 1.34 (3H, t, J=7.5 Hz), 2.61 (3H, s), 2.63 (3H, s), 2.89 (2H, q, J=7.5 Hz), 3.88 (2H, q, J=7.5 Hz), 5.58 (2H, s), 6.60 (2H, s), 7.00 (1H, s), 7.20 (2H, d, J=9 Hz), 7.30 (2H, d, J=9 Hz)

(4)

3-[4-[5-Chloro-1-methyl-3-(1H-tetrazol-5-yl)-2-pyrrolyl]benzyl]-2-ethyl-5,7-dimethyl-3H-imidazo[4,5-b]pyridine mp: 244°-245° C. (dec.)

NMR (DMSO-d₆, δ): 1.25 (3H, t, J=7 Hz), 2.51 (6H, s), 2.82 (2H, q, J=7 Hz), 5.53 (2H, s), 6.68 (1H, s), 6.97 (1H, s), 7.20 (2H, d, J=9 Hz), 7.37 (2H, d, J=9 Hz)

(5)

3-[4-[5-Chloro-1-ethyl-3-(1H-tetrazol-5-yl)-2-pyrrolyl]benzyl]-5,7-dimethyl-2-propyl-3H-imidazo[4,5-b]pyridine mp: 211°-213° C.

NMR (CDCl₃-CD₃OD, δ): 0.96 (3H, t, J=7 Hz), 1.18 (3H, t, J=7 Hz), 1.75 (2H, m), 2.60 (3H, s), 2.65 (3H, s), 2.83 (2H, t, J=7 Hz), 3.39 (2H, q, J=7 Hz), 5.59 (2H, s), 6.60 (1H, s), 6.99 (1H, s), 7.20 (2H, d, J=9 Hz), 7.30 (2H, d, J=9 Hz)

(6)

3-[4-[5-Chloro-1-methyl-3-(1H-tetrazol-5-yl)-2-pyrrolyl]benzyl]-5,7-dimethyl-2-propyl-3H-imidazo[4,5-b]pyridine mp: 191°-193° C.

NMR (CDCl₃-CD₃OD, δ): 0.99 (3H, t, J=7 Hz), 1.77 (2H, m), 2.60 (3H, s), 2.62 (3H, s), 2.84 (2H, t, J=7 Hz), 3.46 (3H, s), 5.57 (2H, s), 6.60 (1H, s), 6.99 (1H, s), 7.19 (2H, d, J=9 Hz), 7.29 (2H, d, J=9 Hz)

(7)

3-[4-[1,5-Dimethyl-3-(1H-tetrazol-5-yl)-2-pyrrolyl]benzyl]-2-ethyl-5,7-dimethyl-3H-imidazo[4,5-b]pyridine mp: 238°-241° C.

NMR (DMSO-d₆, δ): 1.26 (3H, t, J=7.5 Hz), 2.27 (3H, s), 2.50 (6H, s), 2.83 (2H, q, J=7.5 Hz), 3.31 (3H, s), 5.52 (2H, s), 6.36 (1H, s), 6.97 (1H, s), 7.18 (2H, d, J=9.0 Hz), 7.31 (2H, d, J=9.0 Hz)

(8)

3-[4-[1-Ethyl-5-methyl-3-(1H-tetrazol-5-yl)-2-pyrrolyl]benzyl]-2-ethyl-5,7-dimethyl-3H-imidazo[4,5-b]pyridine mp: 261.5°-262.5° C.

NMR (DMSO-d₆, δ): 1.02 (3H, t, J=7.0 Hz), 1.22 (3H, t, J=7.5 Hz), 2.29 (3H, s), 2.51 (6H, s), 2.82 (2H, q, J=7.5 Hz), 3.73 (2H, q, J=7.0 Hz), 5.53 (2H, s), 6.34 (1H, s), 6.97 (1H, s), 7.19 (2H, d, J=9.0 Hz), 7.30 (2H, d, J=9.0 Hz)

(9)

3-[4-[1,5-Dimethyl-3-(1H-tetrazol-5-yl)-2-pyrrolyl]benzyl]-7methyl-2-propyl-3H-imidazo[4,5-b]pyridine mp: 202°-204.5° C.

NMR (DMSO-d₆, δ): 0.93 (3H, t, J=7.5 Hz), 1.62-1.83 (2H, m), 2.27 (3H, s), 2.57 (3H, s), 2.86 (2H, t, J=7.5 Hz), 3.32 (3H, s), 5.58 (2H, s), 6.34 (1H, s), 7.09 (1H, d, J=5.0 Hz), 7.21 (2H, d, J=9.0 Hz), 7.32 (2H, d, J=9.0 Hz), 8.17 (1H, d, J=5.0 Hz)

(10)

3-[4-[1-Ethyl-5-methyl-3-(1H-tetrazol-5-yl)-2-pyrrolyl]benzyl]-7-methyl-2-propyl-3H-imidazo[4,5-b]pyridine mp: 176°-178° C.

NMR (DMSO-d₆, δ): 0.90 (3H, t, J=7.5 Hz), 1.00 (3H, t, J=7.0 Hz), 1.58-1.80 (2H, m), 2.29 (3H, s), 2.58 (3H, s), 2.82 (2H, t, J=7.5 Hz), 3.71 (2H, q, J=7.0 Hz), 5.58 (2H, s), 6.34 (1H, s), 7.10 (1H, d, J=5.0 Hz), 7.21 (2H, d, J=9.0 Hz), 7.30 (2H, d, J=9.0 Hz), 8.20 (1H, d, J=5.0 Hz)

(11)

3-[4-[1,5-Dimethyl-3-(1H-tetrazol-5-yl)-2-pyrrolyl]benzyl]-5,7-dimethyl-2-propyl-3H-imidazo[4,5-b]pyridine mp: 148°-153° C.

NMR (DMSO-d₆, δ): 0.91 (3H, t, J=7.5 Hz), 1.59-1.82 (2H, m), 2.27 (3H, s), 2.80 (2H, t, J=7.5 Hz), 3.32 (3H, s), 5.53 (2H, s), 6.35 (1H, s), 6.97 (1H, s), 7.17 (2H, d, J=9 Hz), 7.31 (2H, d, J=9 Hz)

(12)

3-[4-1-Ethyl-5-methyl-3-(1H-tetrazol-5-yl)-2-pyrrolyl]benzyl]-5,7-dimethyl-2-propyl-3H-imidazo[4,5-b]pyridine mp: 208°-209° C.

NMR (DMSO-d₆, δ): 0.88 (3H, t, J=7 Hz), 1.00 (3H, t, J=7 Hz), 1.66 (2H, m), 2.30 (3H, s), 2.50 (6H, s), 2.77 (2H, q, J=7 Hz), 3.73 (2H, q, J=7 Hz), 5.54 (2H, s), 6.34 (1H, s), 6.97 (1H, s), 7.18 (2H, d, J=9 Hz), 7.30 (2H, d, J=9 Hz)

(13)

3-[4-[2-Bromo-1-methyl-4-(1H-tetrazol-5-yl)-3-pyrrolyl]benzyl]-2-ethyl-5,7-dimethyl-3H-imidazo[4,5-b]pyridine mp: 229°-231° C.

NMR (DMSO-d₆, δ): 1.25 (3H, t, J=7.5 Hz), 2.81 (2H, q, J=7.5 Hz), 3.71 (3H, s), 5.48 (2H, s), 6.95 (1H, s), 7.10 (2H, d, J=9 Hz), 7.20 (2H, d, J=9 Hz), 7.63 (1H, s)

(14)

3-[4-[2-Bromo-1-methyl-4-(1H-tetrazol-5-yl)-3-pyrrolyl]benzyl]-5,7-dimethyl-2-propyl-3H-imdazo[4,5-b]pyridine mp: 151°-153° C.

NMR (DMSO-d₆, δ): 0.91 (3H, t, J=7.5 Hz), 1.59-1.82 (2H, m), 2.76 (2H, t, J=7.5 Hz), 3.71 (3H, s), 5.48 (2H, s), 6.95 (1H, s), 7.10 (2H, d, J=9 Hz), 7.20 (2H, d, J=9 Hz), 7.63 (1H, s)

EXAMPLE 42

The following compounds were obtained according to a similar manner to that of Example 3.

(1) Sodium salt of 3-[4-[5-chloro-1-ethyl-3-(1H-tetrazol-5-yl)-2-pyrrolyl]benzyl]-7-methyl-2-propyl-3H-imidazo[4,5-b]pyridine NMR (D₂O, δ): 0.57 (3H, t, J=7 Hz), 0.64 (3H, t, J=7 Hz), 1.38 (2H, m), 2.35 (3H, s), 2.68 (2H, t, J=7 Hz), 3.29 (2H, br q, J=7 Hz), 5.36 (2H, s), 6.44 (1H, s), 6.80 (1H, d, J=5 Hz), 6.83 (2H, d, J=9 Hz), 6.95 (2H, d, J=9 Hz), 7.88 (1H, d, J=5 Hz)

(2) Sodium salt of 3-[4-[5-chloro-1-methyl-3-(1H-tetrazol-5-yl)-2-pyrrolyl]benzyl]-7-methyl-2-propyl-3H-imidazo[4,5-b]pyridine NMR (D₂O, δ): 0.77 (3H, t, J=7 Hz), 1.50 (2H, s), 2.40 (3H, s), 2.71 (2H, t, J=7 Hz), 2.89 (3H, s), 5 35 (2H, s), 6.47 (1H, s), 6.73 (2H, d, J=5 Hz), 6.82-6.92 (3H), 7.91 (1H, d, J=5 Hz)

(3) Sodium salt of
3-[4-[5-chloro-1-ethyl-3-(1H-tetrazol-5-yl)-2-pyrrolyl]-benzyl]-2-ethyl-5,7-dimethyl-3H-imidazo[4,5-b]pyridine NMR (D$_2$O, δ): 0.53 (3H, t, J=7 Hz), 1.02 (3H, t, J=7 Hz), 2.24 (6H, s), 2.66 (2H, q, J=7 Hz), 3.24 (2H, br q, J=7 Hz), 5.80 (2H, br s), 6.43 (1H, s), 6.50 (1H, s), 6.80 (2H, d, J=9 Hz), 6.93 (2H, d, J=9 Hz)

(4) Sodium salt of
3-[4-[5-chloro-1-methyl-3-(1H-tetrazol-5-yl)-2-pyrrolyl]benzyl]-2-ethyl-5,7-dimethyl-3H-imidazo[4,5-b]pyridine NMR (D$_2$O, δ): 1.11 (3H, t, J=7 Hz), 2.29 (6H, s), 2.70 (2H, q, J=7 Hz), 2.82 (3H, s), 5.30 (2H, s), 6.43 (1H, s), 6.64 (1H, s), 6.72 (2H, d, J=9 Hz), 6.88 (2H, d, J=9 Hz)

(5) Sodium salt of
3-[4-[5-chloro-1-ethyl-3-(1H-tetrazol-5-yl)-2-pyrrolyl]-benzyl]-5,7-dimethyl-2-propyl-3H-imidazo[4,5-b]pyridine mp: 172°–176° C.

NMR (DMSO-d$_6$, δ): 0.89 (3H, t, J=7 Hz), 1.02 (3H, t, J=7 Hz), 1.68 (2H, m), 2.49 (3H, s), 2.51 (3H, s), 2.76 (2H, t, J=7.5 Hz), 3.75 (2H, q, J=7 Hz), 5.50 (2H, s), 6.36 (1H, s), 6.95 (1H, s), 7.10 (2H, d, J=9 Hz), 7.35 (2H, d, J=9 Hz)

(6) Sodium salt of
3-[4-[5-chloro-1-methyl-3-(1H-tetrazol-5-yl)-2-pyrrolyl]benzyl]-5,7-dimethyl-2-propyl-3H-imidazo[4,5-b]pyridine NMR (D$_2$O, δ): 0.68 (3H, t, J=7.5 Hz), 1.40 (2H, m), 2.26 (6H, s), 2.60 (2H, t, J=8 Hz), 2.71 (3H, s), 5.78 (2H, s), 6.44 (1H, s), 6.58 (1H, s), 6.73 (2H, d, J=9 Hz), 6.87 (2H, d, J=9 Hz)

(7) Sodium salt of
3-[4-[1,5-dimethyl-3-(1H-tetrazol-5-yl)-2-pyrrolyl]benzyl]-2-ethyl-5,7-dimethyl-3H-imidazo[4,5-b]pyridine NMR (D$_2$O, δ): 1.08 (3H, t, J=7.5 Hz), 2.07 (3H, s), 2.30 (6H, s), 2.68 (2H, q, J=7.5 Hz), 2.85 (3H, s), 5.28 (2H, s), 6.28 (1H, s), 6.65 (1H, s), 6.80 (2H, d, J=9.0 Hz), 6.88 (2H, d, J=9.0 Hz)

(8) Sodium salt of
3-[4-[1-ethyl-5-methyl-3-(1H-tetrazol-5-yl)-2-pyrrolyl]benzyl]-2-ethyl-5,7-dimethyl-3H-imidazo[4,5-b]pyridine mp: 138.5°–148° C.

NMR (DMSO-d$_6$, δ): 0.97 (3H, t, J=7.5 Hz), 1.23 (3H, t, J=7.5 Hz), 2.24 (3H, s), 2.80 (2H, q, J=7.5 Hz), 3.69 (2H, q, J=7.5 Hz), 5.48 (2H, s), 6.10 (1H, s), 6.95 (1H, s), 7.07 (2H, d, J=9 Hz), 7.31 (2H, d, J=9 Hz)

(9) Sodium salt of
3-[4-[1,5-dimethyl-3-(1H-tetrazol-5-yl)-2-pyrrolyl]benzyl]-7-methyl-2-propyl-3H-imidazo[4,5-b]pyridine NMR (D$_2$O, δ): 0.75 (3H, t, J=7.5 Hz), 1.48 (2H, m), 2.11 (3H, s), 2.42 (3H, s), 2.69 (2H, t, J=7.5 Hz), 2.90 (3H, s), 5.33 (2H, s), 6.30 (1H, s), 6.80 (2H, d, J=9.0 Hz), 6.87 (2H, d, J=9.0 Hz), 6.89 (1H, d, J=5.0 Hz), 7.90 (1H, d, J=5.0 Hz)

(10) Sodium salt of
3-[4-[1-ethyl-5-methyl-3-(1H-tetrazol-5-yl)-2-pyrrolyl]benzyl]-7-methyl-2-propyl-3H-imidazo[4,5-b]pyridine NMR (D$_2$O, δ): 0.60 (3H, t, J=7.5 Hz), 0.64 (3H, t, J=7.0 Hz), 1.26–1.49 (2H, m), 2.10 (3H, s), 2.38 (3H, s), 2.68 (2H, t, J=7.5 Hz), 3.28 (2H, q, J=7.0 Hz), 5.32 (2H, s), 6.30 (1H, s), 6.81 (1H, d, J=5.0 Hz), 6.85 (2H, d, J=9.0 Hz), 6.94 (2H, d, J=9.0 Hz), 7.90 (1H, d, J=5.0 Hz)

(11) Sodium salt of
3-[4-[1,5-dimethyl-3-(1H-tetrazol-5-yl)-2-pyrrolyl]benzyl]-5,7-dimethyl-2-propyl-3H-imidazo[4,5-b]pyridine mp: 112°–113° C.

NMR (DMSO-d$_6$, δ): 0.93 (3H, t, J=7.5 Hz), 1.60–1.84 (2H, m), 2.23 (3H, s), 2.79 (2H, t, J=7.5 Hz), 3.28 (3H, s), 5.46 (2H, s), 6.11 (1H, s), 6.95 (1H, s), 7.06 (2H, d, J=9 Hz), 7.48 (2H, d, J=9 Hz)

(12) Sodium salt of
3-[4-[1-ethyl-5-methyl-3-(1H-tetrazol-5-yl)-2-pyrrolyl]benzyl]-5,7-dimethyl-2-propyl-3H-imidazo[4,5-b]pyridine mp: 165°–173° C.

NMR (DMSO-d$_6$, δ): 0.90 (3H, t, J=7 Hz), 0.98 (3H, t, J=7 Hz), 1.68 (2H, m), 2.25 (3H, s), 2.52 (6H, s), 2.77 (2H, t, J=7 Hz), 3.69 (2H, q, J=7 Hz), 5.49 (2H, s), 6.11 (1H, s), 6.95 (1H, s), 7.07 (2H, d, J=9 Hz), 7.31 (2H, d, J=9 Hz)

(13) Sodium salt of
3-[4-[2-bromo-1-methyl-4-(1H-tetrazol-5-yl)-3-pyrrolyl]benzyl]-2-ethyl-5,7-dimethyl-3H-imidazo[4,5-b]pyridine mp: 188°–190° C.

NMR (DMSO-d$_6$, δ): 1.27 (3H, t, J=7.5 Hz), 2.82 (2H, q, J=7.5 Hz), 3.63 (3H, s), 5.43 (2H, s), 6.94 (1H, s), 7.00 (2H, d, J=9 Hz), 7.20 (1H, s), 7.31 (2H, d, J=9 Hz)

(14) Sodium salt of
3-[4-[2-bromo-1-methyl-4-(1H-tetrazol-5-yl)-3-pyrrolyl]benzyl]-5,7-dimethyl-2-propyl-3H-imidazo[4,5-b]pyridine mp: 171°–173° C.

NMR (DMSO-d$_6$, δ): 0.93 (3H, t, J=7.5 Hz), 1.62–1.84 (2H, m), 2.78 (2H, t, J=7.5 Hz), 3.63 (3H, s), 5.43 (2H, s), 6.94 (1H, s), 6.99 (2H, d, J=9 Hz), 7.19 (1H, s), 7.30 (2H, d, J=9 Hz)

EXAMPLE 43

The following compounds were obtained according to similar manners to those of Examples 28 and 29 successively.

(1)
3-[4-[4-Chloro-2-(1H-tetrazol-5-yl)-1-pyrrolyl]benzyl]-7-methyl-2-propyl-3H-imidazo[4,5-b]pyridine mp: 225°–227° C.

NMR (DMSO-d$_6$, δ): 0.95 (3H, t, J=7.5 Hz), 1.62–1.86 (2H, m), 2.57 (3H, s), 2.84 (2H, t, J=7.5 Hz), 5.58 (2H, s), 6.92 (1H, d, J=1 Hz), 7.10 (1H, d, J=5 Hz), 7.14–7.35 (4H, m), 7.49 (1H, d, J=1 Hz), 8.18 (1H, d, J=5 Hz)

(2)

7-Methyl-3-[4-[2-methyl-5-(1H-tetrazol-5-yl)-1-pyrrolyl]benzyl]-2-propyl-3H-imidazo[4,5-b]pyridine mp: 184°-186° C.

NMR (DMSO-d6, δ): 0.90 (3H, t, J=7.5 Hz), 1.57-1.79 (2H, m), 1.99 (3H, s), 2.57 (3H, s), 2.82 (2H, t, J=7.5 Hz), 5.60 (2H, s), 6.18 (1H, d, J=4.5 Hz), 6.80 (1H, d, J=4.5 Hz), 7.10 (1H, d, J=5.0 Hz), 7.22 (4H, s), 8.19 (1H, d, J=5.0 Hz)

Preparation 149

The following compound was obtained according to a similar manner to that of Preparation 9.

3-[4-(2-Chloro-4-cyano-1-methyl-3-pyrrolyl)benzyl]-5,7-dimethyl-2-propyl-3H-imidazo[4,5-b]pyridine mp: 150°-152° C.

NMR (CDCl3, δ): 0.99 (3H, t, J=7.5 Hz), 1.66-1.90 (2H, m), 2.61 (3H, s), 2.65 (3H, s), 2.80 (2H, m), 3.67 (3H, s), 5.50 (2H, s), 6.92 (1H, s), 7.11-7.23 (3H, m), 7.50 (2H, d, J=9 Hz)

EXAMPLE 44

The following compound was obtained according to a similar manner to that of Example 1.

3-[4-[2-Chloro-1-methyl-4-(1H-tetrazol-5-yl)-3-pyrrolyl]benzyl]-5,7-dimethyl-2-propyl-3H-imidazo[4,5-b]pyridine mp: 147°-150° C.

NMR (DMSO-d6, δ): 0.91 (3H, t, J=7.5 Hz), 1.60-1.81 (2H, m), 2.51 (6H, s), 2.77 (2H, t, J=7.5 Hz), 3.70 (3H, s), 5.48 (2H, s), 6.96 (1H, s), 7.10 (2H, d, J=9 Hz), 7.21 (2H, d, J=9 Hz), 7.51 (1H, s)

EXAMPLE 45

The following compound was obtained according to a similar manner to that of Example 3.

Sodium salt of 3-[4-[2-chloro-1-methyl-4-(1H-tetrazol-5-yl)-3-pyrrolyl]benzyl]-5,7-dimethyl-2-propyl-3H-imidazo[4,5-b]pyridine NMR (D2O, δ): 0.68 (3H, t, J=7.5 Hz), 1.32-1.55 (2H, m), 2.29 (3H, s), 2.35 (3H, s), 2.58 (2H, t, J=7.5 Hz), 3.31 (3H, s), 5.28 (2H, s), 6.63 (1H, s), 6.77-6.90 (4H, m), 7.04 (1H, s)

What we claim is:

1. A compound of the formula:

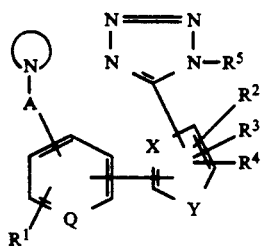

wherein $R^1$ is hydrogen, halogen, nitro, lower alkyl, lower alkoxy, amino or acylamino, lower alkoxy, amino or acylamino, $R^2$, $R^3$ and $R^4$ are each hydrogen, halogen, nitro, cyano, lower alkyl, lower alkenyl, lower alkylthio, mono or di or trihalo(lower)alkyl, oxo(lower)alkyl, hydroxy(lower)alkyl, or optionally esterified carboxy; or $R^2$ and $R^3$ are linked together to form 1,3-butadienylene, $R^5$ is hydrogen or an imino-protective group, A is lower alkylene, Q is CH or N, X is N or CH, Y is NH, O or S, and

is imidazolyl which is condensed at the 4,5-positions with a heterocyclic ring, which may have substituents selected from the group consisting of lower alkyl, halogen, lower alkoxy, hydroxy(lower)alkyl and optionally esterified carboxy, provided that Y=NH when X=CH, and a pharmaceutically acceptable salt thereof.

2. A compound of claim 1, wherein

is 1H-imidazol-1-yl is condensed with pyrrole, imidazole, pyrazole, pyridine, pyrimidine, furan or thiophene, which may have lower alkyl, halogen, lower alkoxy, hydroxy(lower)alkyl, carboxy or lower alkoxycarbonyl substituents.

3. A compound of claim 2, wherein $R^1$ is hydrogen, halogen, nitro, lower alkyl, lower alkoxy, amino or lower alkanoylamino, $R^2$, $R^3$ and $R^4$ are each hydrogen, halogen, nitro, cyano, lower alkyl, lower alkenyl, lower alkylthio, mono- or di- or trihalo(lower)alkyl, oxo(lower)alkyl, hydroxy(lower)alkyl, carboxy or lower alkoxycarbonyl, $R^5$ is hydrogen or mono- or di- or triphenyl(lower)alkyl, and

is 3H-imidazo[4,5-b]pyridin-3-yl, 3H-imidazo[4,5-d]pyramidin-3-yl, 1H-theino[3,4-d]imidazol-1-yl, each of which may have lower alkyl, halogen, lower alkoxy, hydroxy(lower)alkyl or lower alkoxycarbonyl substituents.

4. A compound of claim 3, wherein $R^1$ and $R^4$ are each hydrogen,

Q and X are each CH and Y is NH.

5. A compound of claim 6, which is represented by the formula:

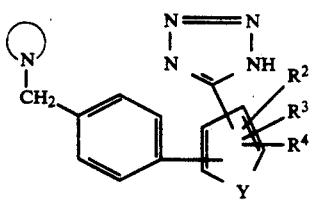

6. A compound of claim 5, wherein

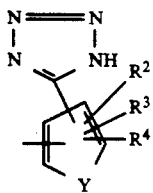

is 2-lower alkyl-3H-imidazo[4,5-b]pyridin-3-yl, 2,7-di(-lower)alkyl-3H-imidazo[4,5-b]pyridin-3-yl, 2,5,7-tri(-lower)alkyl-3H-imidazo[4,5-b]pyridin3-yl, 5-halo-2-lower alkyl-3H-imidazo[4,5-b]pyridin-3-yl, 5-lower alkoxy-2-lower alkyl-3H-imidazo[4,5-b]pyridin-3-yl, 2-lower alkyl-3H-imidazo[4,5-d]pyridin-3-yl, 2-lower alkyl-1H-thieno[3,4-d]imidazol-1-yl, and

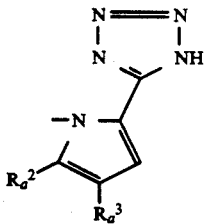

is a group of the formula:

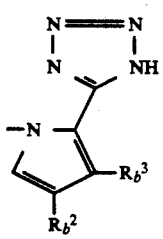

wherein $R_a{}^2$ is hydrogen, halogen, cyano, lower alkyl or lower alkylthio, and $R_a{}^3$ is hydrogen, halogen, nitro, lower alkyl, lower alkenyl, trihalo(lower)alkyl, oxo(-lower)alkyl, hydroxy(lower)alkyl or lower alkoxycarbonyl;

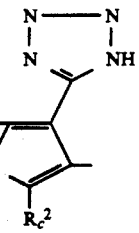

wherein $R_b{}^2$ and $R_b{}^3$ are each halogen;

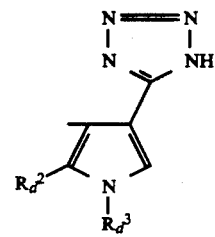

wherein $R_c{}^2$ is hydrogen, halogen or lower alkyl, $R_3{}^3$ is lower alkyl, and $R_c{}^4$ is hydrogen or halogen;

wherein $R_d{}^2$ is hydrogen, halogen or lower alkyl, and $R_d{}^3$ is lower alkyl.

7. A compound of claim 6, which is selected from the group consisting of:
(1) 3-[4-[4-bromo-2-(1H-tetrazol-5-yl)-1-pyrrolyl]-benzyl]-2-butyl-7-methyl-3H-imidazo[4,5-b]pyridine,
(2) 2-butyl-3-[4-[3,4-dichloro-2-(1H-tetrazol-5-yl)-1-pyrrolyl]benzoyl]-7-methyl-3H-imidazo[4,5-b]pyridine,
(3) 3-[4-[2-bromo-5-(1H-tetrazol-5-yl)-1-pyrrolyl]benzyl]-2-butyl-7-methyl-3H-imidazo[4,5-b]pyridine,
(4) 3-[4-[4-bromo-2-(1H-tetrazol-5-yl)-1-pyrrolyl]benzyl]-7-methyl-2-propyl-3H-imidazo[4,5-b]pyridine,
(5) 2-butyl-3-[4-[4-chloro-2-(1H-tetrazol-5-yl)-1-pyrrolyl]benzyl]-7-methyl-3H-imidazo[4,5-b]pyridine,
(6) 3-[4-[4-chloro-2-(1H-tetrazol-5-yl)-1-pyrrolyl]benzyl]-7-methyl-2-propyl-3H-imidazo[4,5-b]pyridine,
(7) 7-methyl-3-[4-[4-methyl-2-(1H-tetrazol-5-yl)-1-pyrrolyl]benzyl]-2-propyl-3H-imidazo[4,5-b]pyridine,
(8) 7-methyl-3-[4-[2-methyl-5-(1H-tetrazol-5-yl)-1-pyrrolyl]benzyl]-2-propyl-3H-imidazo[4,5-b]pyridine,
(9) 3-[4-[3-chloro-2-methyl-5-(1H-tetrazol-5-yl)-1-pyrrolyl]benzyl]-7-methyl-2-propyl-3H-imidazo[4,5-b]pyridine,
(10) 3-[4-[4-chloro-2-(1H-tetrazol-5-yl)-1-pyrrolyl]benzyl]-2-ethyl-5,7-dimethyl-3H-imidazo[4,5-b]pyridine,
(11) 5,7-dimethyl-3-[4-[2-methyl-5-(1H-tetrazol-5-yl)-1-pyrrolyl]benzyl]-2-propyl-3H-imidazo[4,5-b]pyridine,
(12) 3-[4-[2,3-dimethyl-5-(1H-tetrazol-5-yl)-1-pyrrolyl]benzyl]-7-methyl-2-propyl-3H-imidazo[4,5-b]pyridine,
(13) 3-[4-[2-chloro-3-methyl-5-(1H-tetrazol-5-yl)-1-pyrrolyl]benzyl]-7-methyl-2-propyl-3H-imidazo[4,5-b]pyridine,
(14) 2-ethyl-5,7-dimethyl-3-[4-[2-methyl-5-(1H-tetrazol-5-yl)-1-pyrrolyl]benzyl]-3H-imidazo[4,5-b]pyridine,
(15) 3-[4-[4-chloro-2-(1H-tetrazol-5-yl)-1-pyrrolyl]benzyl]-2-ethyl-7-methyl-3H-imidazo[4,5-b]pyridine,
(16) 3-[4-[4-chloro-2-(1H-tetrazol-5-yl)-1-pyrrolyl]benzyl]-5,7-dimethyl-2-propyl-3H-imidazo[4,5-b]pyridine

(17) 3-[4-[2-chloro-1-methyl-4-(1H-tetrazol-5-yl)-3-pyrrolyl]benzyl]-7-methyl-2-propyl-3H-imidazo[4,5-b]pyridine

(18) 3-[4-[5-bromo-1-ethyl-3-(1H-tetrazol-5-yl)-2-pyrrolyl]benzyl]-7-methyl-2-propyl-3H-imidazo[4,5-b]pyridine

(19) 3-[4-[1-ethyl-3-(1H-tetrazol-5-yl)-2-pyrrolyl]benzyl]-7-methyl-2-propyl-3H-imidazo[4,5-b]pyridine,

(20) 3-[4-[2-chloro-1-methyl-4-(1H-tetrazol-5-yl)-3-pyrrolyl]benzyl]-5,7-dimethyl-2-ethyl-3H-imidazo[4,5-b]pyridine,

(21) 5,7-dimethyl-2-ethyl-3-[4-[1-ethyl-3-(1H-tetrazol-5-yl)-2-pyrrolyl]benzyl]imidazo[4,5-b]pyridine,

(22) 5,7-dimethyl-3-[4-[1-ethyl-3-(1H-tetrazol-5-yl)-2-pyrrolyl]benzyl]-2-propyl-3H-imidazo[4,5-b]pyridine, and

(23) 3-[4-[2-chloro-1-methyl-4-(1H-tetrazol-5-yl)-3-pyrrolyl]benzyl]-5,7-dimethyl-2-propyl-3H-imidazo[4,5-b]pyridine, or their sodium salt or hydrochloride.

8. A pharmaceutical composition comprising a compound of claim 1 or pharmaceutically acceptable salt thereof in association with a pharmaceutically acceptable, substantially non-toxic carrier or excipient.

9. A method for treating or preventing angiotensin II mediated diseases, which comprises administering a compound of claim 1 or pharmaceutically acceptable salt thereof to human being or animals.

10. A method for treating or preventing hypertension or heart failure, which comprises administering a compound of claim 1 or pharmaceutically acceptable salt thereof to human being or animals.

* * * * *

UNITED STATES PATENT AND TRADEMARK OFFICE
CERTIFICATE OF CORRECTION

PATENT NO. : 5,215,994
DATED : June 1, 1993
INVENTOR(S) : Teruo Oku et al.

It is certified that error appears in the above-indentified patent and that said Letters Patent is hereby corrected as shown below:

On the title page, Item [75],

The inventor's information is incorrect, should read:

--Teruo Oku; Hiroyuki Setoi; Hiroshi Kayakiri; Shigeki Satoh; Takayuki Inoue; Yuki Saitoh; Akio Kuroda, all of Tsukuba; Hirokazu Tanaka, Tsuchiura, all of Japan--

Signed and Sealed this

Ninth Day of August, 1994

Attest:

BRUCE LEHMAN

*Attesting Officer*   *Commissioner of Patents and Trademarks*